(12) United States Patent
Tassone et al.

(10) Patent No.: US 9,404,091 B2
(45) Date of Patent: *Aug. 2, 2016

(54) DEHYDROGENASE VARIANTS AND POLYNUCLEOTIDES ENCODING SAME

(71) Applicants: Novozymes, Inc., Davis, CA (US); Novozymes A/S, Bagsvaerd (DK)

(72) Inventors: Monica Tassone, Davis, CA (US); Leonardo De Maria, Bagsvaerd (DK)

(73) Assignees: Novozymes, Inc., Davis, CA (US); Novozymes A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 14/875,452

(22) Filed: Oct. 5, 2015

(65) Prior Publication Data

US 2016/0017296 A1      Jan. 21, 2016

Related U.S. Application Data

(63) Continuation of application No. 14/242,721, filed on Apr. 1, 2014, now Pat. No. 9,163,220, which is a continuation of application No. 13/825,515, filed as application No. PCT/US2012/057134 on Sep. 25, 2012, now Pat. No. 8,728,788.

(60) Provisional application No. 61/541,363, filed on Sep. 30, 2011.

(51) Int. Cl.
| | |
|---|---|
| *C12N 9/04* | (2006.01) |
| *C12P 7/42* | (2006.01) |
| *C12P 7/52* | (2006.01) |

(52) U.S. Cl.
CPC ............... *C12N 9/0006* (2013.01); *C12P 7/42* (2013.01); *C12P 7/52* (2013.01); *C12Y 101/01059* (2013.01); *C12Y 101/01276* (2013.01); *C12Y 101/01298* (2013.01); *Y02P 20/52* (2015.11)

(58) Field of Classification Search
None
See application file for complete search history.

(56) References Cited

U.S. PATENT DOCUMENTS

| | | | |
|---|---|---|---|
| 8,728,788 B1 * | 5/2014 | Tassone | ........ C12Y 101/01276 435/183 |
| 2009/0325248 A1 | 12/2009 | Marx et al. | |
| 2010/0021978 A1 | 1/2010 | Burk et al. | |
| 2011/0201073 A1 | 8/2011 | Buelter et al. | |

FOREIGN PATENT DOCUMENTS

| | | |
|---|---|---|
| WO | 0242418 A2 | 5/2002 |
| WO | 03062173 A2 | 7/2003 |
| WO | 03082795 A2 | 10/2003 |
| WO | 2005118719 A2 | 12/2005 |
| WO | 2006022664 A2 | 3/2006 |
| WO | 2006047589 A2 | 5/2006 |
| WO | 2008027742 A1 | 3/2008 |
| WO | 2008089102 A2 | 7/2008 |
| WO | 2008091627 A2 | 7/2008 |
| WO | 2009089457 A1 | 7/2009 |
| WO | 2010077874 A2 | 1/2010 |
| WO | 2010031083 A2 | 3/2010 |
| WO | 0116346 A1 | 3/2011 |
| WO | 2012074818 A2 | 6/2012 |
| WO | 2013043758 A2 | 3/2013 |

OTHER PUBLICATIONS

Dujon et al, 2004—Uniprot Access No. Q6CVY7.
Fookes et al 2011, Uniprot Access No. F8VES4.
Henry et al, 2010, Biotechnol Bioeng 106(3), 462-47.
Khoury et al, 2009, Protein Science 18, 2125-2138.
Ravin et al, 2011—Uniprot Access No. E7R2D7.
Richter et al, 2011, Eng Life Sci 11(1), 26-36.
Straathof et al, 2005, Appl Microbiol Biotechnol 67, 727-734.
Sutton et al, 2008, Uniprot Access No. B1ELX0.
Yamazawa et al, 2011, J Biochem 149(6), 701-712.
Fujisawa et al, 2003, Biochemica et Biophysica Acta 1645, 89-94.
Jiang et al, 2009, Appl Microbiol Biotechnol 82, 995-1003.
Dohr et al, 2001, Proc Natl Acad Sci USA 98(1), 81-86.
Eppink et al, 1999, J Mol Biol 292, 87-96.
Hall et al, 2000, Microbiology 146, 1399-1406.
US 2011-0201073 Uniport Access No. AZM00759.
Chica et al, 2005, Curr Op Biotechnol 16(4), 378-384.
Sen et al, 2007, Appl Biochem Biotechnol 143(3), 212-223.

* cited by examiner

*Primary Examiner* — Christian Fronda
(74) *Attorney, Agent, or Firm* — Eric Fechter

(57) ABSTRACT

The present invention relates to 3-hydroxypropionate dehydrogenase variants. The present invention also relates to polynucleotides encoding the variants; nucleic acid constructs, vectors, and host cells comprising the polynucleotides; and methods of using the variants.

20 Claims, 13 Drawing Sheets

| | | |
|---|---|---|
| E. coli | 1 | ----------------MIVLVTGATAGFGECITRRFIQQG---HKVIATGRRQERLQELKDEL |
| I. orientalis | 1 | MFG--NISQRLAGKNILITGASTGIGYHTAKYFAEAANGDLKLVLAARRKEKLEALKADL |
| S. cerevisiae | 1 | MSQGRKAAERLAKKTVLITGASAGIGKATALEYLEASNGDMKLILAARRLEKLEELKKTI |
| E. coli | 45 | GDN-----LYIAQLDVRNRAAIEEMLASLPAEWCNIDILVNNAGLALGMEPAHKASVEDW |
| I. orientalis | 59 | LAKYPSIKVHIESLDVSKTETIAPFLKGLPEEFSIVDVLVNNAGKALGLDPIGSVDPKDV |
| S. cerevisiae | 61 | DQEFPNAKVHVAQLDITQAEKIKPFIENLPQEFKDIDILVNNAGKALGSDRVGQIATEDI |
| E. coli | 100 | ETMIDTNNKGLVYMTRAVLPGMVERNHGHIINIGSTAGSWPYAGGNVYGATKAFVRQFSL |
| I. orientalis | 119 | DEMFQTNVLGMIQLTQLVVQQMKERNSGDIVQLGSVAGRNPYPGGGIYCASKAALRSFTH |
| S. cerevisiae | 121 | QDVFDTNVTALININITQAVLPIFQAKNSGDIVNLGSIAGRDAYPTGSIYCASKFAVGAFTD |
| E. coli | 160 | NLRTDLHGTAVRVTDIEPGIVGGTEFSNVRFKGDDGKAEKTYQNTVALTPEDVSEAVWWV |
| I. orientalis | 179 | VLREELINTKIRVIEIEPGNVATEEFSLTRFKGDKSKAEKVYEGTEPLYGTDIAELILFA |
| S. cerevisiae | 181 | SLRKELINTKIRVLIAPG-LVETEFSLVRYRGNEEQAKNVYKDTTPLMADDVADLIVYA |
| E. coli | 220 | STLPAHVNINTLEMPVTQSYAGLNVHRQ---- |
| I. orientalis | 239 | VSRPQNTVIAETLVFASNQASA-YHIFRGSLDK |
| S. cerevisiae | 240 | TSRKQNTVIADTLIFPTNQASP-HHIFRG---- |

Fig. 2

```
E. coli (wt):   MIVLVTGATAGFGECITRRFIQQG----HKVIATGRRQERLQELKDEL...
    mut1:       MIVLVTGAG*GFGECITRRFIQQG----HKVIATDLNPAALQELKDEL...
    mut2:       MIVLVTGAGAGFGECITRRFIQQG----HKVIATELNPAALQELKDEL...
    mut3:       MIVLVTGAG*GFGECITRRFIQQG----HKVIATELNPAALQELKDEL...
    mut4:       MIVLVTGAGAGFGECITRRFIQQG----HKVIATDLSADALQELKDEL...
    mut5:       MIVLVTGAG*GFGECITRRFIQQG----HKVIATDLSADALQELKDEL...
    mut6:       MIVLVTGAGAGFGECITRRFIQQG----HKVIATDLNPAALQELKDEL...
    mut7:       MIVLVTGAG*GFGECITRRFIQQG----HKVIATELSADALQELKDEL...
    mut8:       MIVLVTGAGAGFGECITRRFIQQG----HKVIATELSADALQELKDEL...
    mut9:       MIVLVTGATAGFGECITRRFIQQG----HKVIATDLNPAALQELKDEL...
    mut10:      MIVLVTGAGAGFGECITRRFIQQG----HKVIATGLNPAALQELKDEL...
    mut11:      MIVLVTGAGAGFGECITRRFIQQG----HKVIATDRNPAALQELKDEL...
    mut12:      MIVLVTGAGAGFGECITRRFIQQG----HKVIATDLRPAALQELKDEL...
    mut13:      MIVLVTGAGAGFGECITRRFIQQG----HKVIATDLNQAALQELKDEL...
    mut14:      MIVLVTGAGAGFGECITRRFIQQG----HKVIATDLNPEALQELKDEL...
    mut15:      MIVLVTGAGAGFGECITRRFIQQG----HKVIATDLNPARLQELKDEL...
    mut16:      MIVLVTGAGAGFGECITRRFIQQG----HKVIATDLRQEALQELKDEL...
    mut17:      MIVLVTGAGAGFGECITRRFIQQG----HKVIATDLRQAALQELKDEL...
    mut18:      MIVLVTGAGAGFGECITRRFIQQG----HKVIATDLRPEALQELKDEL...
    mut19:      MIVLVTGAGAGFGECITRRFIQQG----HKVIATDLNQEALQELKDEL...
    mut20:      MIVLVTGAGAGFGECITRRFIQQG----HKVIATDRRQERLQELKDEL...
    mut21:      MIVLVTGAGAGFGECITRRFIQQG----HKVIATDRRQEALQELKDEL...
    mut22:      MIVLVTGAGAGFGECITRRFIQQG----HKVIATDLRQERLQELKDEL...
    mut23:      MIVLVTGATAGFGECITRRFIQQG----HKVIATGRRQERLQELKDEL...
    mut24:      MIVLVTGAGAGFGECITRRFIQQG----HKVIATDRRQERLQELKDEL...
    mut25:      MIVLVTGATAGFGECITRRFIQQG----HKVIATDLRQERLQELKDEL...
I_o (wt):       MFG--NISQRLAGKNILITGASTGIGYHTAKYFAEAANGDLKIVLAARKEKLEALKADL...
    mut26:      MFG--NISQRLAGKNILITGASTGIGYHTAKYFAEAANGDLKIVLADLRKEKLEALKADL...
    mut27:      MFG--NISQRLAGKNILITGAGTGIGYHTAKYFAEAANGDLKIVLADLRKEKLEALKADL...
```

DEHYDROGENASE VARIANTS AND POLYNUCLEOTIDES ENCODING SAME

CROSS-REFERENCE TO RELATED APPLICATIONS

This application is a continuation of U.S. patent application Ser. No. 14/242,721, filed Apr. 1, 2014, now U.S. Pat. No. 9,163,220, which is a continuation of U.S. patent application Ser. No. 13/825,515, now U.S. Pat. No. 8,728,788, which is a 35 U.S.C. §371 national application of PCT/US2012/057134, filed Sep. 25, 2012, which claims priority to U.S. Provisional Application No. 61/541,363, filed Sep. 30, 2011. The contents of these applications are hereby incorporated by reference in their entireties.

REFERENCE TO A SEQUENCE LISTING

This application contains a Sequence Listing in computer readable form, which is incorporated herein by reference.

BACKGROUND 3-hydroxypropionic acid (3-HP) is a three carbon carboxylic acid identified by the U.S. Department of Energy as one of the top 12 high-potential building block chemicals that can be made by fermentation. Alternative names for 3-HP, which is an isomer of lactic (2-hydroxypropionic) acid, include ethylene lactic acid and 3-hydroxypropionate. 3-HP is an attractive renewable platform chemical, with 100% theoretical yield from glucose, multiple functional groups that allow it to participate in a variety of chemical reactions, and low toxicity. 3-HP can be used as a substrate to form several commodity chemicals, such as 1,3-propanediol, malonic acid, acrylamide, and acrylic acid. Acrylic acid is a large-volume chemical (>7 billion lbs/year) used to make acrylate esters and superabsorbent polymers, and is currently derived from catalytic oxidation of propylene. Fermentative production of 3-HP would provide a sustainable alternative to petrochemicals as the feedstock for these commercially-significant chemicals, thus reducing energy consumption, dependence on foreign oil supplies, and the production of greenhouse gases.

3-hydroxypropionate dehydrogenase (3-HPDH) is an enzyme that converts malonate semialdehyde to 3-HP (FIG. 1). Certain 3-HPDH enzymes utilize the cofactor NADP(H) (EC 1.1.1.298). However, it may be desirable with some engineered metabolic pathways for 3-HPDH to utilize the cofactor NAD(H) rather than NADP(H) (e.g., to improve redox balance). Accordingly, there is a need in the art to develop dehydrogenase variants that have increased specificity for the cofactor NAD(H) compared to NADP(H). Described herein are dehydrogenase variants that meet this need.

SUMMARY

Described herein are 3-hydroxypropionate dehydrogenase variants comprising a substitution at one or more (e.g., two, several) positions corresponding to positions 9, 31, 32, 33, 34, 35 and 36 of SEQ ID NO: 2, wherein the variants have 3-hydroxypropionate dehydrogenase activity. In some aspects, the variants comprise a deletion at a position corresponding to position 10 of SEQ ID NO: 2. In some aspects, the variants have increased specificity for the cofactor NAD(H) compared to NADP(H).

Also described are isolated polynucleotides encoding the variants; nucleic acid constructs, vectors, and host cells comprising the polynucleotides; methods of producing 3-hydroxypropionic acid (3-HP) using the host cells comprising the polynucleotides; and methods of producing the variants.

BRIEF DESCRIPTION OF THE FIGURES

FIG. 2 shows an alignment of native dehydrogenase sequences for E. coli ydfG, I. orientalis YMR226c, and S. cerevisiae YMR226c (SEQ ID NOs: 2, 4, and 6, respectively). Residues involved in cofactor binding are underlined. Residues involved in catalysis are boldfaced.
FIG. 3 shows a partial sequence alignment for the N-terminal region of variant dehydrogenases mut1-mut25 (SEQ ID NOs: 7, 8, 9, 10, 11, 12, 13, 14, 17, 18, 19, 20, 21, 22, 23, 24, 25, 26, 27, 28, 29, 30, 31, 32, and 33, respectively) compared to the native E. coli dehydrogenase (SEQ ID NO: 2); and for the N-terminal region of variant dehydrogenases mut26 and mut27 (SEQ ID NOs: 80 and 81, respectively) compared to the native I. orientalis dehydrogenase (SEQ ID NO: 4).

DEFINITIONS 3-hydroxypropionate dehydrogenase: The term "3-hydroxypropionate dehydrogenase" (3-HPDH) means an enzyme that catalyzes the interconversion of malonate semialdehyde to 3-hydroxypropionate (3-HP) in the presence of a NAD(H) or NADP(H) cofactor. Enzymes having 3-HP dehydrogenase activity are classified as EC 1.1.1.59 if they utilize an NAD(H) cofactor, and as EC 1.1.1.298 if they utilize an NADP(H) cofactor. Enzymes classified as EC 1.1.1.298 are alternatively referred to as malonate semialdehyde reductases. One skilled in the art will recognize that 3-hydroxypropionate dehydrogenases may have specificity for more than one substrate. For example, the E. coli 3-hydroxypropionate dehydrogenase of SEQ ID NO: 2 may catalyze both the interconversion of serine to 2-aminomalonate semialdehyde (i.e. a "serine dehydrogenase") and the interconversion of 3-HP to malonate semialdehyde (i.e., a 3-HPDH).

3-hydroxypropionate dehydrogenase activity can be determined according to malonate semi-aldehyde reductase assay described in the Examples. In one aspect, the variants of the present invention have at least 20%, e.g., at least 40%, at least 50%, at least 60%, at least 70%, at least 80%, at least 90%, at least 95%, or at least 100% of the 3-hydroxypropionate dehydrogenase of SEQ ID NO: 2, 4, or 6.

Figure 1:
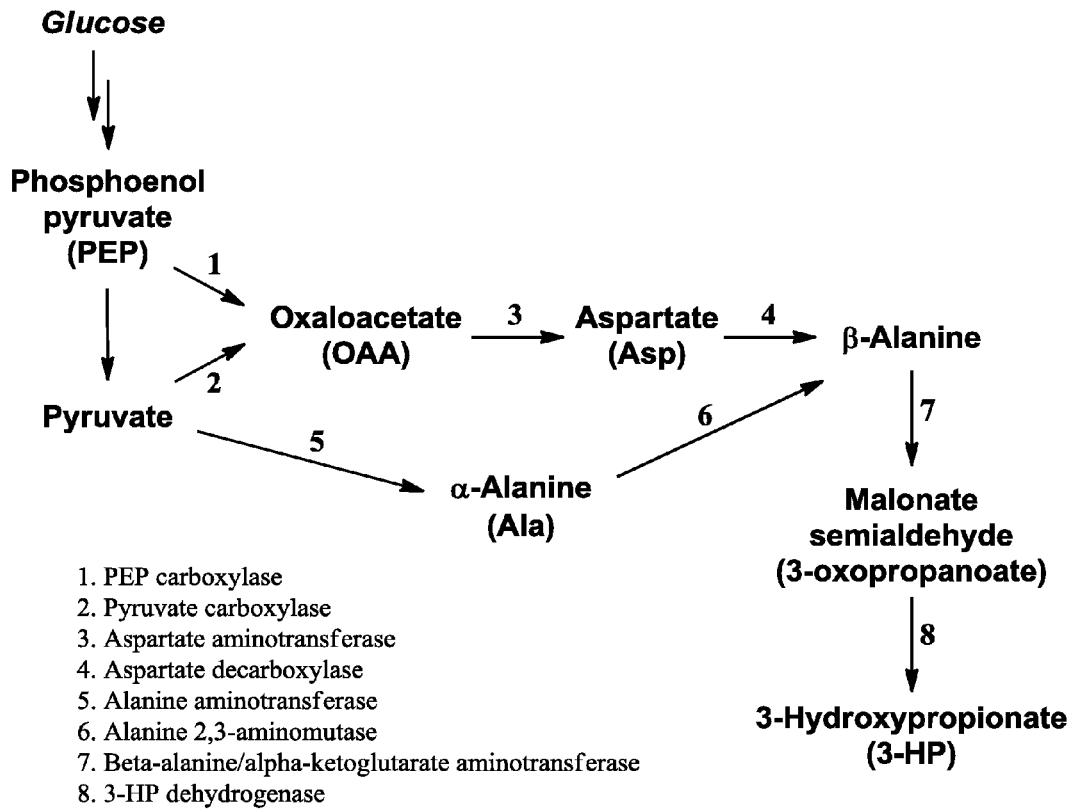
FIG. 1 shows a pathway for generating 3-HP.

Active 3-HP pathway: As used herein, a host cell having an "active 3-HP pathway" produces active enzymes necessary to catalyze each reaction in a metabolic pathway from a fermentable sugar to 3-HP, and therefore is capable of producing 3-HP in measurable yields when cultivated under fermentation conditions in the presence of at least one fermentable sugar. A host cell having an active 3-HP pathway comprises one or more 3-HP pathway genes. A "3-HP pathway gene" as used herein refers to a gene that encodes an enzyme involved in an active 3-HP pathway. One example of an active 3-HP pathway and corresponding enzymes involved in the active 3-HP pathway is shown in FIG. 1.

The active enzymes necessary to catalyze each reaction in active 3-HP pathway may result from activities of endogenous gene expression, activities of heterologous gene expression, or from a combination of activities of endogenous and heterologous gene expression.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Coding sequence: The term "coding sequence" means a polynucleotide sequence, which specifies the amino acid sequence of a polypeptide. The boundaries of the coding sequence are generally determined by an open reading frame, which usually begins with the ATG start codon or alternative start codons such as GTG and TTG and ends with a stop codon such as TAA, TAG, and TGA. The coding sequence may be a sequence of genomic DNA, cDNA, a synthetic polynucleotide, and/or a recombinant polynucleotide.

Control sequence: The term "control sequence" means a nucleic acid sequence necessary for polypeptide expression. Control sequences may be native or foreign to the polynucleotide encoding the polypeptide, and native or foreign to each other. Such control sequences include, but are not limited to, a leader sequence, polyadenylation sequence, propeptide sequence, promoter sequence, signal peptide sequence, and transcription terminator sequence. The control sequences may be provided with linkers for the purpose of introducing specific restriction sites facilitating ligation of the control sequences with the coding region of the polynucleotide encoding a polypeptide.

Expression: The term "expression" includes any step involved in the production of the polypeptide including, but not limited to, transcription, post-transcriptional modification, translation, post-translational modification, and secretion. Expression can be measured—for example, to detect increased expression—by techniques known in the art, such as measuring levels of mRNA and/or translated polypeptide.

Expression vector: The term "expression vector" means a linear or circular DNA molecule that comprises a polynucleotide encoding a polypeptide and is operably linked to control sequences, wherein the control sequences provide for expression of the polynucleotide encoding the polypeptide. At a minimum, the expression vector comprises a promoter sequence, and transcriptional and translational stop signal sequences.

Fermentable medium: The term "fermentable medium" refers to a medium comprising one or more (e.g., two, several) sugars, such as glucose, fructose, sucrose, cellobiose, xylose, xylulose, arabinose, mannose, galactose, and/or soluble oligosaccharides, wherein the medium is capable, in part, of being converted (fermented) into 3-HP by a host cell having an active 3-HP pathway. In some instances, the fermentation medium is derived from a natural source, such as sugar cane, starch, or cellulose, and may be the result of pretreating the source by enzymatic hydrolysis (saccharification).

Fragment: The term "fragment" means a polypeptide having one or more (e.g., two, several) amino acids deleted from the amino and/or carboxyl terminus of a referenced polypeptide sequence. In one aspect, the fragment has 3-HPDH activity. In another aspect, the number of amino acid residues in the fragment is at least 75%, e.g., at least 80%, 85%, 90%, or 95% of any 3-HPDH herein, e.g., at least 75%, e.g., at least 80%, 85%, 90%, or 95% of the number of amino acid residues in SEQ ID NOs: 2, 4, or 6.

Heterologous polynucleotide: The term "heterologous polynucleotide" is defined herein as a polynucleotide that is not native to the host cell; a native polynucleotide in which one or more (e.g., two, several) structural modifications have been made to the coding region; a native polynucleotide whose expression is quantitatively altered as a result of manipulation of the DNA by recombinant DNA techniques, e.g., a different (foreign) promoter linked to the polynucleotide; or a native polynucleotide whose expression is quantitatively altered by the introduction of one or more extra copies of the polynucleotide into the host cell.

Host cell: The term "host cell" means any cell type that is susceptible to transformation, transfection, transduction, and the like with a nucleic acid construct or expression vector comprising a polynucleotide described herein (e.g., a polynucleotide encoding a 3-HPDH). The term "host cell" encompasses any progeny of a parent cell that is not identical to the parent cell due to mutations that occur during replication.

Increased specificity: The term "increased specificity for NAD(H) compared to NADP(H)" means the referenced polypeptide has greater 3-HPDH activity in the presence of NAD(H) compared to NADP(H) in otherwise identical conditions. In some aspects, the referenced variant has more than 2-fold, e.g., more than 5-fold, 10-fold, 20-fold, 50-fold, 100-fold, 200-fold, 500-fold, or 1000-fold specificity for NAD(H) compared to NADP(H).

Isolated: The term "isolated" means a substance in a form or environment which does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Mutant: The term "mutant" means a polynucleotide encoding a variant.

Nucleic acid construct: The term "nucleic acid construct" means a polynucleotide that comprises one or more (e.g., two, several) control sequences. The polynucleotide may be single-stranded or double-stranded, and may be isolated from a naturally occurring gene, modified to contain segments of nucleic acids in a manner that would not otherwise exist in nature, or synthetic.

Operably linked: The term "operably linked" means a configuration in which a control sequence is placed at an appropriate position relative to the coding sequence of a polynucleotide such that the control sequence directs the expression of the coding sequence.

Parent or parent 3-HPDH: The term "parent" or "parent 3-HPDH" means a 3-HPDH to which an alteration is made to produce the enzyme variants of the present invention. The parent may be a naturally occurring (wild-type) polypeptide or a variant or fragment thereof.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix.

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix.

Stringency conditions: Stringency conditions are used herein to provide hybridization conditions when comparing two DNA sequences.

The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Subsequence: The term "subsequence" means a polynucleotide having one or more (e.g., two, several) nucleotides deleted from the 5' and/or 3' end of the referenced nucleotide sequence. In one aspect, the subsequence encodes a fragment having 3-HPDH activity. In another aspect, the number of nucleotides residues in the subsequence is at least 75%, e.g., at least 80%, 85%, 90%, or 95% of the number of nucleotide residues in any sequence encoding a 3-HPDH described herein, e.g., at least 75%, e.g., at least 80%, 85%, 90%, or 95% of the number of nucleotide residues in SEQ ID NOs: 1, 3, or 5.

Variant: The term "variant" means a 3-HPDH comprising an alteration, i.e., a substitution, insertion, and/or deletion, at one or more (e.g., two, several) positions relative to a parent 3-HPDH. A substitution means replacement of the amino acid occupying a position with a different amino acid; a deletion means removal of the amino acid occupying a position; and an insertion means adding an amino acid adjacent to and immediately following the amino acid occupying a position.

Wild-type: The term "wild-type" 3-HPDH or "native" 3-HPDH means a 3-HPDH expressed by a naturally occurring microorganism, such as a bacterium, yeast, or filamentous fungus found in nature.

Conventions for Designation of Variants

For purposes described herein, SEQ ID NO: 2 is used to determine amino acid numbering in other 3-HPDH enzymes. The amino acid sequence of another 3-HPDH is aligned with SEQ ID NO: 2, and based on the alignment, the amino acid position number corresponding to any amino acid residue in the polypeptide disclosed in SEQ ID NO: 2 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another 3-HPDH can be determined by an alignment of multiple polypeptide sequences using several computer programs including, but not limited to, MUSCLE (multiple sequence comparison by log-expectation; version 3.5 or later; Edgar, 2004, *Nucleic Acids Research* 32: 1792-1797), MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537:_39-64; Katoh and Toh, 2010, *Bioinformatics* 26:_1899-1900), and EMBOSS EMMA employing ClustalW (1.83 or later; Thompson et al., 1994, *Nucleic Acids Research* 22: 4673-4680), using their respective default parameters.

When the other enzyme sequence has diverged from the SEQ ID NO: 2 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementation of these algorithms can additionally be utilized to query structure databases with a structure of interest in order to discover possible structural homologs (e.g., Holm and Park, 2000, *Bioinformatics* 16: 566-567).

In describing the variants described herein, the nomenclature described below is adapted for ease of reference. The accepted IUPAC single letter or three letter amino acid abbreviation is employed.

Substitutions.

For an amino acid substitution, the following nomenclature is used: Original amino acid, position, substituted amino acid. Accordingly, the substitution of threonine at position 226 with alanine is designated as "Thr226Ala" or "T226A". Alternative substitutions at the same position are separated by a slant. For example, the substitution of threonine at position 226 with alanine or valine is designated as "Thr226Ala/Val" or "T226A/V", representing a T226A or T226V substitution. Multiple mutations are separated by addition marks ("+"), e.g., "Gly205Arg+Ser411Phe/Tyr" or "G205R+S411F/Y", representing substitutions at positions 205 and 411 of glycine (G) with arginine (R) and serine (S) with phenylalanine (F) or tyrosine (Y), respectively.

Deletions.

For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions.

For an amino acid insertion, the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---|---|
| 195 | 195 195a 195b |
| G | G - K - A |

Reference to "about" a value or parameter herein includes aspects that are directed to that value or parameter per se. For example, description referring to "about X" includes the aspect "X". When used in combination with measured values, "about" includes a range that encompasses at least the uncertainty associated with the method of measuring the particular value, and can include a range of plus or minus two standard deviations around the stated value.

As used herein and in the appended claims, the singular forms "a," "or," and "the" include plural referents unless the context clearly dictates otherwise. It is understood that the aspects described herein include "consisting" and/or "consisting essentially of" aspects.

Unless defined otherwise or clearly indicated by context, all technical and scientific terms used herein have the same meaning as commonly understood by one of ordinary skill in the art.

DETAILED DESCRIPTION

Described herein, inter alia, are polypeptides having 3-HPDH activity. In some aspects, the polypeptides are variants comprising a substitution at one or more (e.g., two, several) positions corresponding to positions 9, 31, 32, 33, 34, 35 and 36 of SEQ ID NO: 2. In some aspects the variants further comprise a deletion at a position corresponding to position 10 of SEQ ID NO: 2. In some aspects, the polypeptides having increased specificity for NAD(H) compared to NADP(H).

Polypeptides Having 3-HPDH Activity

In one aspect is a polypeptide having 3-HPDH activity, wherein the polypeptide is:

a) a polypeptide having at least 60%, e.g., at least 65%, at least 70%, at least 75%, at least 80%, at least 85%, at least 90%, at least 95%, at least 96%, at least 97%, at least 98%, or at least 99%, sequence identity to SEQ ID NO: 2, 4, or 6;

b) a polypeptide encoded by a polynucleotide that hybridizes under low stringency conditions, e.g., medium stringency conditions, medium-high stringency conditions, high stringency conditions, or very high stringency conditions with the full-length complementary strand of SEQ ID NO: 1, 3, or 5; or c) a polypeptide encoded by a polynucleotide having at least 60%, e.g., at least 65%, at least 70%, at least 75%, at least 80%, at least 85%, at least 90%, at least 95%, at least 96%, at least 97%, at least 98%, or at least 99%, sequence identity to SEQ ID NO: 1, 3, or 5;

wherein the polypeptide has increased specificity for NAD (H) compared to NADP(H) (e.g., greater than 2-fold, 5-fold, 10-fold, 20-fold, 50-fold, 100-fold, 200-fold, 500-fold, or 1000-fold specificity for NAD(H) compared to NADP(H)).

In one aspect, the polypeptide a) has at least 60%, e.g., at least 65%, at least 70%, at least 75%, at least 80%, at least 85%, at least 90%, at least 95%, at least 96%, at least 97%, at least 98%, at least 99% or 100% sequence identity to SEQ ID NO: 2; b) is encoded by a polynucleotide that hybridizes under at least low stringency conditions, e.g., medium stringency conditions, medium-high stringency conditions, high stringency conditions, or very high stringency conditions with the full-length complementary strand of SEQ ID NO: 1; and/or c) is encoded by a polynucleotide having at least 60%, e.g., at least 65%, at least 70%, at least 75%, at least 80%, at least 85%, at least 90%, at least 95%, at least 96%, at least 97%, at least 98%, at least 99%, or 100% sequence identity to SEQ ID NO: 1.

In some of these aspects related to SEQ ID NO: 2, at least one of positions 9, 31, 32, 33, 34, 35 and 36 corresponding to SEQ ID NO: 2 differs from SEQ ID NO: 2. In one embodiment, at least two of positions 9, 31, 32, 33, 34, 35 and 36 corresponding to SEQ ID NO: 2 differ from SEQ ID NO: 2. In another embodiment, at least three of positions 9, 31, 32, 33, 34, 35 and 36 corresponding to SEQ ID NO: 2 differ from SEQ ID NO: 2. In another embodiment, at least four of positions 9, 31, 32, 33, 34, 35 and 36 corresponding to SEQ ID NO: 2 differ from SEQ ID NO: 2. In another embodiment, at least five of positions 9, 31, 32, 33, 34, 35 and 36 corresponding to SEQ ID NO: 2 differ from SEQ ID NO: 2. In another embodiment, at least six of positions 9, 31, 32, 33, 34, 35 and 36 corresponding to SEQ ID NO: 2 differ from SEQ ID NO: 2. In another embodiment, all of positions 9, 31, 32, 33, 34, 35 and 36 corresponding to SEQ ID NO: 2 differ from SEQ ID NO: 2.

In another aspect, the polypeptide a) has at least 60%, e.g., at least 65%, at least 70%, at least 75%, at least 80%, at least 85%, at least 90%, at least 95%, at least 96%, at least 97%, at least 98%, at least 99% or 100% sequence identity to SEQ ID NO: 4; b) is encoded by a polynucleotide that hybridizes under at least low stringency conditions, e.g., medium stringency conditions, medium-high stringency conditions, high stringency conditions, or very high stringency conditions with the full-length complementary strand of SEQ ID NO: 3; and/or c) is encoded by a polynucleotide having at least 60%, e.g., at least 65%, at least 70%, at least 75%, at least 80%, at least 85%, at least 90%, at least 95%, at least 96%, at least 97%, at least 98%, at least 99%, or 100% sequence identity to SEQ ID NO: 3.

In some of these aspects related to SEQ ID NO: 4, at least one of positions 9, 31, 32, 33, 34, 35 and 36 corresponding to SEQ ID NO: 2 differs from SEQ ID NO: 4. In one embodiment, at least two of positions 9, 31, 32, 33, 34, 35 and 36 corresponding to SEQ ID NO: 2 differ from SEQ ID NO: 4. In another embodiment, at least three of positions 9, 31, 32, 33, 34, 35 and 36 corresponding to SEQ ID NO: 2 differ from SEQ ID NO: 4. In another embodiment, at least four of positions 9, 31, 32, 33, 34, 35 and 36 corresponding to SEQ ID NO: 2 differ from SEQ ID NO: 4. In another embodiment, at least five of positions 9, 31, 32, 33, 34, 35 and 36 corresponding to SEQ ID NO: 2 differ from SEQ ID NO: 4. In another embodiment, at least six of positions 9, 31, 32, 33, 34, 35 and 36 corresponding to SEQ ID NO: 2 differ from SEQ ID NO: 4. In another embodiment, all of positions 9, 31, 32, 33, 34, 35 and 36 corresponding to SEQ ID NO: 2 differ from SEQ ID NO: 4.

In another aspect, the polypeptide a) at least 60%, e.g., at least 65%, at least 70%, at least 75%, at least 80%, at least 85%, at least 90%, at least 95%, at least 96%, at least 97%, at least 98%, at least 99% or 100% sequence identity to SEQ ID NO: 6; b) is encoded by a polynucleotide that hybridizes under at least low stringency conditions, e.g., medium stringency conditions, medium-high stringency conditions, high stringency conditions, or very high stringency conditions with the full-length complementary strand of SEQ ID NO: 5; and/or is encoded by a polynucleotide having at least 60%, e.g., at least 65%, at least 70%, at least 75%, at least 80%, at least 85%, at least 90%, at least 95%, at least 96%, at least 97%, at least 98%, at least 99%, or 100% sequence identity to SEQ ID NO: 5.

In some of these aspects related to SEQ ID NO: 6, at least one of positions 9, 31, 32, 33, 34, 35 and 36 corresponding to SEQ ID NO: 2 differs from SEQ ID NO: 6. In one embodiment, at least two of positions 9, 31, 32, 33, 34, 35 and 36 corresponding to SEQ ID NO: 2 differ from SEQ ID NO: 6. In another embodiment, at least three of positions 9, 31, 32, 33, 34, 35 and 36 corresponding to SEQ ID NO: 2 differ from SEQ ID NO: 6. In another embodiment, at least four of positions 9, 31, 32, 33, 34, 35 and 36 corresponding to SEQ ID NO: 2 differ from SEQ ID NO: 6. In another embodiment, at least five of positions 9, 31, 32, 33, 34, 35 and 36 corresponding to SEQ ID NO: 2 differ from SEQ ID NO: 6. In another embodiment, at least six of positions 9, 31, 32, 33, 34, 35 and 36 corresponding to SEQ ID NO: 2 differ from SEQ ID NO: 6. In another embodiment, all of positions 9, 31, 32, 33, 34, 35 and 36 corresponding to SEQ ID NO: 2 differ from SEQ ID NO: 6.

In one aspect, the polypeptide may comprise an Ala, Arg, Asn, Asp, Cys, Gln, Glu, Gly, His, Ile, Leu, Lys, Met, Phe, Pro, Ser, Thr, Trp, Tyr, or Val at a position corresponding to position 9 of SEQ ID NO: 2. In some embodiments, the amino acid corresponding to position 9 is Gly. In some embodiments, the polypeptide comprises a deletion at a position corresponding to position 10.

In another aspect, the polypeptide may comprise an Ala, Arg, Asn, Asp, Cys, Gln, Glu, Gly, His, Ile, Leu, Lys, Met, Phe, Pro, Ser, Thr, Trp, Tyr, or Val at a position corresponding to position 31 of SEQ ID NO: 2. In some embodiments, the amino acid corresponding to position 31 is Asp or Glu. In some embodiments, the polypeptide comprises a deletion at a position corresponding to position 10.

In another aspect, the polypeptide may comprise an Ala, Arg, Asn, Asp, Cys, Gln, Glu, Gly, His, Ile, Leu, Lys, Met, Phe, Pro, Ser, Thr, Trp, Tyr, or Val at a position corresponding to position 32 of SEQ ID NO: 2. In some embodiments, the amino acid corresponding to position 32 is Leu. In some embodiments, the polypeptide comprises a deletion at a position corresponding to position 10.

In another aspect, the polypeptide may comprise an Ala, Arg, Asn, Asp, Cys, Gln, Glu, Gly, His, Ile, Leu, Lys, Met, Phe, Pro, Ser, Thr, Trp, Tyr, or Val at a position corresponding to position 33 of SEQ ID NO: 2. In some embodiments, the amino acid corresponding to position 33 is Ser or Asn. In some embodiments, the polypeptide comprises a deletion at a position corresponding to position 10.

In another aspect, the polypeptide may comprise an Ala, Arg, Asn, Asp, Cys, Gln, Glu, Gly, His, Ile, Leu, Lys, Met, Phe, Pro, Ser, Thr, Trp, Tyr, or Val at a position corresponding to position 34 of SEQ ID NO: 2. In some embodiments, the amino acid corresponding to position 34 is Ala or Pro. In some embodiments, the polypeptide comprises a deletion at a position corresponding to position 10.

In another aspect, the polypeptide may comprise an Ala, Arg, Asn, Asp, Cys, Gln, Glu, Gly, His, Ile, Leu, Lys, Met, Phe, Pro, Ser, Thr, Trp, Tyr, or Val at a position corresponding to position 35 of SEQ ID NO: 2. In some embodiments, the amino acid corresponding to position 35 is Ala or Asp. In some embodiments, the polypeptide comprises a deletion at a position corresponding to position 10.

In another aspect, the polypeptide may comprise an Ala, Arg, Asn, Asp, Cys, Gin, Glu, Gly, His, Ile, Leu, Lys, Met, Phe, Pro, Ser, Thr, Trp, Tyr, or Val at a position corresponding to position 36 of SEQ ID NO: 2. In some embodiments, the amino acid corresponding to position 36 is Ala. In some embodiments, the polypeptide comprises a deletion at a position corresponding to position 10.

In one aspect of the polypeptide, the position corresponding to 9 is Gly and 31 is Asp or Glu; 9 is Gly and 32 is Leu; 9 is Gly and 33 is Ser or Asn; 9 is Gly and 34 is Ala or Pro; 9 is Gly and 35 is Ala or Asp; 9 is Gly and 36 is Ala; 31 is Asp or Glu and 32 is Leu; 31 is Asp or Glu and 33 is Ser or Asn; 31 is Asp or Glu and 34 is Ala or Pro; 31 is Asp or Glu and 35 is Ala or Asp; 31 is Asp or Glu and 36 is Ala; 32 is Leu and 33 is Ser or Asn; 32 is Leu and 34 is Ala or Pro; 32 is Leu and 35 is Ala or Asp; 32 is Leu and 36 is Ala; 33 is Ser or Asn and 34 is Ala or Pro; 33 is Ser or Asn and 35 is Ala or Asp; 33 is Ser or Asn and 36 is Ala; 34 is Ala or Pro and 35 is Ala or Asp; 34 is Ala or Pro and 36 is Ala; or 35 is Ala or Asp and 36 is Ala. In some embodiments, the polypeptide comprises a deletion at a position corresponding to position 10.

In another aspect of the polypeptide, the position corresponding to 9 is Gly, 31 is Asp or Glu, and 32 is Leu; 9 is Gly, 31 is Asp or Glu, and 33 is Ser or Asn; 9 is Gly, 31 is Asp or Glu, and 34 is Ala or Pro; 9 is Gly, 31 is Asp or Glu, and 35 is Ala or Asp; 9 is Gly, 31 is Asp or Glu, and 36 is Ala; 9 is Gly, 32 is Leu, and 33 is Ser or Asn; 9 is Gly, 32 is Leu, and 34 is Ala or Pro; 9 is Gly, 32 is Leu, and 35 is Ala or Asp; 9 is Gly, 32 is Leu, and 36 is Ala; 9 is Gly, 33 is Ser or Asn, and 34 is Ala or Pro; 9 is Gly, 33 is Ser or Asn, and 35 is Ala or Asp; 9 is Gly, 33 is Ser or Asn, and 36 is Ala; 9 is Gly, 34 is Ala or Pro, and 35 is Ala or Asp; 9 is Gly, 34 is Ala or Pro, and 36 is Ala; 9 is Gly, 35 is Ala or Asp, and 36 is Ala; 31 is Asp or Glu, 32 is Leu, and 33 is Ser or Asn; 31 is Asp or Glu, 32 is Leu, and 34 is Ala or Pro; 31 is Asp or Glu, 32 is Leu, and 35 is Ala or Asp; 31 is Asp or Glu, 32 is Leu, and 36 is Ala; 31 is Asp or Glu, 33 is Ser or Asn, and 34 is Ala or Pro; 31 is Asp or Glu, 33 is Ser or Asn, and 35 is Ala or Asp; 31 is Asp or Glu, 33 is Ser or Asn, and 36 is Ala; 31 is Asp or Glu, 34 is Ala or Pro, and 35 is Ala or Asp; 31 is Asp or Glu, 34 is Ala or Pro, and 36 is Ala; 31 is Asp or Glu, 35 is Ala or Asp, and 36 is Ala; 32 is Leu, 33 is Ser or Asn, and 34 is Ala or Pro; 32 is Leu, 33 is Ser or Asn, and 35 is Ala or Asp; 32 is Leu, 33 is Ser or Asn, and 36 is Ala; 32 is Leu, 34 is Ala or Pro, and 35 is Ala or Asp; 32 is Leu, 34 is Ala or Pro, and 36 is Ala; 32 is Leu, 35 is Ala or Asp, and 36 is Ala; 33 is Ser or Asn, 34 is Ala or Pro, and 35 is Ala or Asp; 33 is Ser or Asn, 34 is Ala or Pro, and 36 is Ala; 33 is Ser or Asn, 35 is Ala or Asp, and 36 is Ala; or 34 is Ala or Pro, 35 is Ala or Asp, and 36 is Ala. In some embodiments, the polypeptide comprises a deletion at a position corresponding to position 10.

In another aspect of the polypeptide, the position corresponding to 9 is Gly, 31 is Asp or Glu, 32 is Leu, and 33 is Ser or Asn; 9 is Gly, 31 is Asp or Glu, 32 is Leu, and 34 is Ala or Pro; 9 is Gly, 31 is Asp or Glu, 32 is Leu, and 35 is Ala or Asp; 9 is Gly, 31 is Asp or Glu, 32 is Leu, and 36 is Ala; 9 is Gly, 31 is Asp or Glu, 33 is Ser or Asn, and 34 is Ala or Pro; 9 is Gly, 31 is Asp or Glu, 33 is Ser or Asn, and 35 is Ala or Asp; 9 is Gly, 31 is Asp or Glu, 33 is Ser or Asn, and 36 is Ala; 9 is Gly, 31 is Asp or Glu, 34 is Ala or Pro, and 35 is Ala or Asp; 9 is Gly, 31 is Asp or Glu, 34 is Ala or Pro, and 36 is Ala; 9 is Gly, 31 is Asp or Glu, 35 is Ala or Asp, and 36 is Ala; 9 is Gly, 32 is Leu, 33 is Ser or Asn, and 34 is Ala or Pro; 9 is Gly, 32 is Leu, 33 is Ser or Asn, and 35 is Ala or Asp; 9 is Gly, 32 is Leu, 33 is Ser or Asn, and 36 is Ala; 9 is Gly, 32 is Leu, 34 is Ala or Pro, and 35 is Ala or Asp; 9 is Gly, 32 is Leu, 34 is Ala or Pro, and 36 is Ala; 9 is Gly, 32 is Leu, 35 is Ala or Asp, and 36 is Ala; 9 is Gly, 33 is Ser or Asn, 34 is Ala or Pro, and 35 is Ala or Asp; 9 is Gly, 33 is Ser or Asn, 34 is Ala or Pro, and 36 is Ala; 9 is Gly, 33 is Ser or Asn, 35 is Ala or Asp, and 36 is Ala; 9 is Gly, 34 is Ala or Pro, 35 is Ala or Asp, and 36 is Ala; 31 is Asp or Glu, 32 is Leu, 33 is Ser or Asn, and 34 is Ala or Pro; 31 is Asp or Glu, 32 is Leu, 33 is Ser or Asn, and 35 is Ala or Asp; 31 is Asp or Glu, 32 is Leu, 33 is Ser or Asn, and 36 is Ala; 31 is Asp or Glu, 32 is Leu, 34 is Ala or Pro, and 35 is Ala or Asp; 31 is Asp or Glu, 32 is Leu, 34 is Ala or Pro, and 36 is Ala; 31 is Asp or Glu, 32 is Leu, 35 is Ala or Asp, and 36 is Ala; 31 is Asp or Glu, 33 is Ser or Asn, 34 is Ala or Pro, and 35 is Ala or Asp; 31 is Asp or Glu, 33 is Ser or Asn, 34 is Ala or Pro, and 36 is Ala; 31 is Asp or Glu, 33 is Ser or Asn, 35 is Ala or Asp, and 36 is Ala; 31 is Asp or Glu, 34 is Ala or Pro, 35 is Ala or Asp, and 36 is Ala; 32 is Leu, 33 is Ser or Asn, 34 is Ala or Pro, and 35 is Ala or Asp; 32 is Leu, 33 is Ser or Asn, 34 is Ala or Pro, and 36 is Ala; 32 is Leu, 33 is Ser or Asn, 35 is Ala or Asp, and 36 is Ala; 32 is Leu, 34 is Ala or Pro, 35 is Ala or Asp, and 36 is Ala; or 33 is Ser or Asn, 34 is Ala or Pro, 35 is Ala or Asp, and 36 is Ala. In some embodiments, the polypeptide comprises a deletion at a position corresponding to position 10.

In another aspect of the polypeptide, the position corresponding to 9 is Gly, 31 is Asp or Glu, 32 is Leu, 33 is Ser or Asn, and 34 is Ala or Pro; 9 is Gly, 31 is Asp or Glu, 32 is Leu, 33 is Ser or Asn, and 35 is Ala or Asp; 9 is Gly, 31 is Asp or Glu, 32 is Leu, 33 is Ser or Asn, and 36 is Ala; 9 is Gly, 31 is Asp or Glu, 32 is Leu, 34 is Ala or Pro, and 35 is Ala or Asp; 9 is Gly, 31 is Asp or Glu, 32 is Leu, 34 is Ala or Pro, and 36 is Ala; 9 is Gly, 31 is Asp or Glu, 32 is Leu, 35 is Ala or Asp, and 36 is Ala; 9 is Gly, 31 is Asp or Glu, 33 is Ser or Asn, 34 is Ala or Pro, and 35 is Ala or Asp; 9 is Gly, 31 is Asp or Glu, 33 is Ser or Asn, 34 is Ala or Pro, and 36 is Ala; 9 is Gly, 31 is Asp or Glu, 33 is Ser or Asn, 35 is Ala or Asp, and 36 is Ala; 9 is Gly, 31 is Asp or Glu, 34 is Ala or Pro, 35 is Ala or Asp, and 36 is Ala; 9 is Gly, 32 is Leu, 33 is Ser or Asn, 34 is Ala or Pro, and 35 is Ala or Asp; 9 is Gly, 32 is Leu, 33 is Ser or Asn, 34 is Ala or Pro, and 36 is Ala; 9 is Gly, 32 is Leu, 33 is Ser or Asn, 35 is Ala or Asp, and 36 is Ala; 9 is Gly, 32 is Leu, 34 is Ala or Pro, 35 is Ala or Asp, and 36 is Ala; 9 is Gly, 33 is Ser or Asn, 34 is Ala or Pro, 35 is Ala or Asp, and 36 is Ala; 31 is Asp or Glu, 32 is Leu, 33 is Ser or Asn, 34 is Ala or Pro, and 35 is Ala or Asp; 31 is Asp or Glu, 32 is Leu, 33 is Ser or Asn, 34 is Ala or Pro, and 36 is Ala; 31 is Asp or Glu, 32 is Leu, 33 is Ser or Asn, 35 is Ala or Asp, and 36 is Ala; 31 is Asp or Glu, 32 is Leu, 34 is Ala or Pro, 35 is Ala or Asp, and 36 is Ala; 31 is Asp or Glu, 33 is Ser or Asn, 34 is Ala or Pro, 35 is Ala or Asp, and 36 is Ala; or 32 is Leu, 33 is Ser or Asn, 34 is Ala or Pro, 35 is Ala or Asp, and 36 is Ala. In some embodiments, the polypeptide comprises a deletion at a position corresponding to position 10.

In another aspect of the polypeptide, the position corresponding to 9 is Gly, 31 is Asp or Glu, 32 is Leu, 33 is Ser or Asn, 34 is Ala or Pro, and 35 is Ala or Asp; 9 is Gly, 31 is Asp or Glu, 32 is Leu, 33 is Ser or Asn, 34 is Ala or Pro, and 36 is Ala; 9 is Gly, 31 is Asp or Glu, 32 is Leu, 33 is Ser or Asn, 35 is Ala or Asp, and 36 is Ala; 9 is Gly, 31 is Asp or Glu, 32 is Leu, 34 is Ala or Pro, 35 is Ala or Asp, and 36 is Ala; 9 is Gly, 31 is Asp or Glu, 33 is Ser or Asn, 34 is Ala or Pro, 35 is Ala or Asp, and 36 is Ala; 9 is Gly, 32 is Leu, 33 is Ser or Asn, 34 is Ala or Pro, 35 is Ala or Asp, and 36 is Ala; or 31 is Asp or Glu, 32 is Leu, 33 is Ser or Asn, 34 is Ala or Pro, 35 is Ala or Asp, and 36 is Ala. In some embodiments, the polypeptide comprises a deletion at a position corresponding to position 10.

In another aspect of the polypeptide, the position corresponding to 9 is Gly, 31 is Asp or Glu, 32 is Leu, 33 is Ser or Asn, 34 is Ala or Pro, 35 is Ala or Asp and 36 is Ala of SEQ ID NO: 2. In some embodiments, the polypeptide comprises a deletion at a position corresponding to position 10.

In any of these aspects, the polypeptide may have increased specificity for NAD(H) compared to NADP(H). In some embodiments, the polypeptide has more than 2-fold, e.g., more than 5-fold, 10-fold, 20-fold, 50-fold, 100-fold, 200-fold, 500-fold, or 1000-fold specificity for NAD(H) compared to NADP(H).

Variants

In some aspects, the polypeptides are described as 3-HPDH variants of a parent 3-HPDH, comprising substitutions at one or more (e.g., two, several) positions corresponding to any of positions 9, 31, 32, 33, 34, 35 and 36 of SEQ ID NO: 2, wherein the variants have 3-HPDH activity. For example, the variants may comprise one or more (e.g., two, several) of the substitutions T/S9G, G/A31D/E, R32L, R33S/N, L/K/Q34A/P, E35D/A, and K/R36A. In some aspects, the variants further comprise a deletion at a position corresponding to position 10. In some aspects, the variants are isolated.

In one embodiment, the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%, but less than 100%, to sequence identity to a parent 3-HPDH.

In one embodiment, the variant has at least 60%, e.g., at least 65%, at least 70%, at least 75%, at least 80%, at least 85%, at least 90%, at least 95%, at least 96%, at least 97%, at least 98%, or at least 99% sequence identity to SEQ ID NO: 2.

In another embodiment, the variant has at least 60%, e.g., at least 65%, at least 70%, at least 75%, at least 80%, at least 85%, at least 90%, at least 95%, at least 96%, at least 97%, at least 98%, or at least 99% sequence identity to SEQ ID NO: 4.

In another embodiment, the variant has at least 60%, e.g., at least 65%, at least 70%, at least 75%, at least 80%, at least 85%, at least 90%, at least 95%, at least 96%, at least 97%, at least 98%, or at least 99% sequence identity to SEQ ID NO: 6.

In one aspect, the number of alterations (substitutions, deletions, and/or insertions) in the variants of the described herein is 1-20, e.g., 1-10 and 1-5, such as 1, 2, 3, 4, 5, 6, 7, 8, 9 or 10 alterations.

In one aspect, the variant comprises or consists of a substitution at a position corresponding to position 9 of SEQ ID NO: 2. For example, the amino acid corresponding to position 9 may be substituted with Ala, Arg, Asn, Asp, Cys, Gln, Glu, Gly, His, Ile, Leu, Lys, Met, Phe, Pro, Ser, Thr, Trp, Tyr, or Val. In one aspect, the amino acid corresponding to position 9 is Gly. In another aspect, the variant comprises or consists of the substitution T/S9G, such as the substitution T9G of a parent comprising SEQ ID NO: 2, or S9G of a parent comprising SEQ ID NO: 4 or 6.

In one aspect, the variant comprises or consists of a substitution at a position corresponding to position 31 of SEQ ID NO: 2. For example, the amino acid corresponding to position 31 may be substituted with Ala, Arg, Asn, Asp, Cys, Gln, Glu, Gly, His, Ile, Leu, Lys, Met, Phe, Pro, Ser, Thr, Trp, Tyr, or Val. In one aspect, the amino acid corresponding to position 31 is Asp or Glu. In another aspect, the variant comprises or consists of the substitution G/A31 D/E, such as the substitution G31 D/E of a parent comprising SEQ ID NO: 2, or A31 D/E of a parent comprising SEQ ID NO: 4 or 6.

In one aspect, the variant comprises or consists of a substitution at a position corresponding to position 32 of SEQ ID NO: 2. For example, the amino acid corresponding to position 32 may be substituted with Ala, Arg, Asn, Asp, Cys, Gln, Glu, Gly, His, Ile, Leu, Lys, Met, Phe, Pro, Ser, Thr, Trp, Tyr, or Val. In one aspect, the amino acid corresponding to position 32 is Leu. In another aspect, the variant comprises or consists of the substitution R32L, such as the substitution R32L of a parent comprising SEQ ID NO: 2, 4, or 6.

In one aspect, the variant comprises or consists of a substitution at a position corresponding to position 33 of SEQ ID NO: 2. For example, the amino acid corresponding to position 33 may be substituted with Ala, Arg, Asn, Asp, Cys, Gln, Glu, Gly, His, Ile, Leu, Lys, Met, Phe, Pro, Ser, Thr, Trp, Tyr, or Val. In one aspect, the amino acid corresponding to position 33 is Ser or Asn. In another aspect, the variant comprises or consists of the substitution R33S/N, such as the substitution R33S/N of a parent comprising SEQ ID NO: 2, 4, or 6.

In one aspect, the variant comprises or consists of a substitution at a position corresponding to position 34 of SEQ ID NO: 2. For example, the amino acid corresponding to position 34 may be substituted with Ala, Arg, Asn, Asp, Cys, Gln, Glu, Gly, His, Ile, Leu, Lys, Met, Phe, Pro, Ser, Thr, Trp, Tyr, or Val. In one aspect, the amino acid corresponding to position 34 is Ala or Pro. In another aspect, the variant comprises or consists of the substitution L/K/Q34A/P, such as the substitution Q34A/P of a parent comprising SEQ ID NO: 2, KQ34A/P of a parent comprising SEQ ID NO: 2, or L34A/P of a parent comprising SEQ ID NO: 6.

In one aspect, the variant comprises or consists of a substitution at a position corresponding to position 35 of SEQ ID NO: 2. For example, the amino acid corresponding to position 35 may be substituted with Ala, Arg, Asn, Asp, Cys, Gln, Glu, Gly, His, Ile, Leu, Lys, Met, Phe, Pro, Ser, Thr, Trp, Tyr, or Val. In one aspect, the amino acid corresponding to position 35 is Ala or Asp. In another aspect, the variant comprises or consists of the substitution E35D/A, such as the substitution E35D/A of a parent comprising SEQ ID NO: 2, 4, or 6.

In one aspect, the variant comprises or consists of a substitution at a position corresponding to position 36 of SEQ ID NO: 2. For example, the amino acid corresponding to position 36 may be substituted with Ala, Arg, Asn, Asp, Cys, Gln, Glu, Gly, His, Ile, Leu, Lys, Met, Phe, Pro, Ser, Thr, Trp, Tyr, or Val. In one aspect, the amino acid corresponding to position 36 is Ala. In another aspect, the variant comprises or consists of the substitution K/R36A, such as the substitution R36A of a parent comprising SEQ ID NO: 2, or K36A of a parent comprising SEQ ID NO: 4 or 6.

In another aspect, the variant comprises or consists of substitutions at any two positions corresponding to positions 9, 31, 32, 33, 34, 35 and 36 of SEQ ID NO: 2. For example, the variant may comprise or consist of two substitutions corresponding to positions 9 and 31; 9 and 32; 9 and 33; 9 and 34; 9 and 35; 9 and 36; 31 and 32; 31 and 33; 31 and 34; 31 and 35; 31 and 36; 32 and 33; 32 and 34; 32 and 35; 32 and 36; 33 and 34; 33 and 35; 33 and 36; 34 and 35; 34 and 36; or 35 and 36, such as those described above. In one aspect, the variant comprises or consists of the substitutions T/S9G and G/A31 D/E; T/S9G and R32L; T/S9G and R33S/N; T/S9G and L/K/Q34A/P; T/S9G and E35D/A; T/S9G and K/R36A; G/A31D/E and R32L; G/A31D/E and R33S/N; G/A31D/E and L/K/Q34A/P; G/A31D/E and E35D/A; G/A31D/E and K/R36A; R32L and R33S/N; R32L and L/K/Q34A/P; R32L and E35D/A; R32L and K/R36A; R33S/N and L/K/Q34A/P; R33S/N and E35D/A; R33S/N and K/R36A; L/K/Q34A/P and E35D/A; L/K/Q34A/P and K/R36A; or E35D/A and K/R36A. In any of these aspects, the variant may further comprise a deletion at a position corresponding to position 10 of SEQ ID NO: 2.

In another aspect, the variant comprises or consists of substitutions at any three positions corresponding to positions 9, 31, 32, 33, 34, 35 and 36 of SEQ ID NO: 2. For example, the variant may comprise or consist of three substitutions corresponding to positions 9, 31, and 32; 9, 31, and 33; 9, 31, and 34; 9, 31, and 35; 9, 31, and 36; 9, 32, and 33; 9, 32, and 34; 9, 32, and 35; 9, 32, and 36; 9, 33, and 34; 9, 33, and 35; 9, 33, and 36; 9, 34, and 35; 9, 34, and 36; 9, 35, and 36; 31, 32, and 33; 31, 32, and 34; 31, 32, and 35; 31, 32, and 36; 31, 33, and 34; 31, 33, and 35; 31, 33, and 36; 31, 34, and 35; 31, 34, and 36; 31, 35, and 36; 32, 33, and 34; 32, 33, and 35; 32, 33, and 36; 32, 34, and 35; 32, 34, and 36; 32, 35, and 36; 33, 34, and 35; 33, 34, and 36; 33, 35, and 36; or 34, 35, and 36, such as those described above. In one aspect, the variant comprises or consists of the substitutions T/S9G, G/A31D/E, and R32L; T/S9G, G/A31D/E, and R33S/N; T/S9G, G/A31D/E, and L/K/Q34A/P; T/S9G, G/A31D/E, and E35D/A; T/S9G, G/A31D/E, and K/R36A; T/S9G, R32L, and R33S/N; T/S9G, R32L, and L/K/Q34A/P; T/S9G, R32L, and E35D/A; T/S9G, R32L, and K/R36A; T/S9G, R33S/N, and L/K/Q34A/P; T/S9G, R33S/N, and E35D/A; T/S9G, R33S/N, and K/R36A; T/S9G, L/K/Q34A/P, and E35D/A; T/S9G, L/K/Q34A/P, and K/R36A; T/S9G, E35D/A, and K/R36A; G/A31 D/E, R32L, and R33S/N; G/A31D/E, R32L, and L/K/Q34A/P; G/A31D/E, R32L, and E35D/A; G/A31D/E, R32L, and K/R36A; G/A31D/E, R33S/N, and L/K/Q34A/P; G/A31D/E, R33S/N, and E35D/A; G/A31D/E, R33S/N, and K/R36A; G/A31D/E, L/K/Q34A/P, and E35D/A; G/A31D/E, L/K/Q34A/P, and K/R36A; G/A31D/E, E35D/A, and K/R36A; R32L, R33S/N, and L/K/Q34A/P; R32L, R33S/N, and E35D/A; R32L, R33S/N, and K/R36A; R32L, L/K/Q34A/P, and E35D/A; R32L, L/K/Q34A/P, and K/R36A; R32L, E35D/A, and K/R36A; R33S/N, L/K/Q34A/P, and E35D/A; R33S/N, L/K/Q34A/P, and K/R36A; R33S/N, E35D/A, and K/R36A; or L/K/Q34A/P, E35D/A, and K/R36A. In any of these aspects, the variant may further comprise a deletion at a position corresponding to position 10 of SEQ ID NO: 2.

In another aspect, the variant comprises or consists of substitutions at any four positions corresponding to positions 9, 31, 32, 33, 34, 35 and 36 of SEQ ID NO: 2. For example, the variant may comprise or consist of four substitutions corresponding to positions 9, 31, 32, and 33; 9, 31, 32, and 34; 9, 31, 32, and 35; 9, 31, 32, and 36; 9, 31, 33, and 34; 9, 31, 33, and 35; 9, 31, 33, and 36; 9, 31, 34, and 35; 9, 31, 34, and 36; 9, 31, 35, and 36; 9, 32, 33, and 34; 9, 32, 33, and 35; 9, 32, 33, and 36; 9, 32, 34, and 35; 9, 32, 34, and 36; 9, 32, 35, and 36; 9, 33, 34, and 35; 9, 33, 34, and 36; 9, 33, 35, and 36; 9, 34, 35, and 36; 31, 32, 33, and 34; 31, 32, 33, and 35; 31, 32, 33, and 36; 31, 32, 34, and 35; 31, 32, 34, and 36; 31, 32, 35, and 36; 31, 33, 34, and 35; 31, 33, 34, and 36; 31, 33, 35, and 36; 31, 34, 35, and 36; 32, 33, 34, and 35; 32, 33, 34, and 36; 32, 33, 35, and 36; 32, 34, 35, and 36; or 33, 34, 35, and 36, such as those described above. In one aspect, the variant comprises or consists of the substitutions T/S9G, G/A31D/E, R32L, and R33S/N; T/S9G, G/A31D/E, R32L, and L/K/Q34A/P; T/S9G, G/A31D/E, R32L, and E35D/A; T/S9G, G/A31D/E, R32L, and K/R36A; T/S9G, G/A31D/E, R33S/N, and L/K/Q34A/P; T/S9G, G/A31D/E, R33S/N, and E35D/A; T/S9G, G/A31D/E, R33S/N, and K/R36A; T/S9G, G/A31D/E, L/K/Q34A/P, and E35D/A; T/S9G, G/A31D/E, L/K/Q34A/P, and K/R36A; T/S9G, G/A31D/E, E35D/A, and K/R36A; T/S9G, R32L, R33S/N, and L/K/Q34A/P; T/S9G, R32L, R33S/N, and E35D/A; T/S9G, R32L, R33S/N, and K/R36A; T/S9G, R32L, L/K/Q34A/P, and E35D/A; T/S9G, R32L, L/K/Q34A/P, and E35D/A; T/S9G, R32L, E35D/A, and K/R36A; T/S9G, R33S/N, L/K/Q34A/P, and E35D/A; T/S9G, R33S/N, L/K/Q34A/P, and K/R36A; T/S9G, R33S/N, E35D/A, and K/R36A; T/S9G, L/K/Q34A/P, E35D/A, and K/R36A; G/A31D/E, R32L, R33S/N, and L/K/Q34A/P; G/A31D/E, R32L, R33S/N, and E35D/A; G/A31D/E, R32L, R33S/N, and K/R36A; G/A31D/E, R32L, L/K/Q34A/P, and E35D/A; G/A31D/E, R32L, L/K/Q34A/P, and K/R36A; G/A31D/E, R32L, E35D/A, and K/R36A; G/A31D/E, R33S/N, L/K/Q34A/P, and E35D/A; G/A31 D/E, R33S/N, L/K/Q34A/P, and K/R36A; G/A31 D/E, R33S/N, E35D/A, and K/R36A; G/A31D/E, L/K/Q34A/P, E35D/A, and K/R36A; R32L, R33S/N, L/K/Q34A/P, and E35D/A; R32L, R33S/N, L/K/Q34A/P, and K/R36A; R32L, R33S/N, E35D/A, and K/R36A; R32L, L/K/Q34A/P, E35D/A, and K/R36A; or R33S/N, L/K/Q34A/P, E35D/A, and K/R36A. In any of these aspects, the variant may further comprise a deletion at a position corresponding to position 10 of SEQ ID NO: 2.

In another aspect, the variant comprises or consists of substitutions at any five positions corresponding to positions 9, 31, 32, 33, 34, 35 and 36 of SEQ ID NO: 2. For example, the variant may comprise or consist of five substitutions corresponding to positions 9, 31, 32, 33, and 34; 9, 31, 32, 33, and 35; 9, 31, 32, 33, and 36; 9, 31, 32, 34, and 35; 9, 31, 32, 34, and 36; 9, 31, 32, 35, and 36; 9, 31, 33, 34, and 35; 9, 31, 33, 34, and 36; 9, 31, 33, 35, and 36; 9, 31, 34, 35, and 36; 9, 32, 33, 34, and 35; 9, 32, 33, 34, and 36; 9, 32, 33, 35, and 36; 9, 32, 34, 35, and 36; 9, 33, 34, 35, and 36; 31, 32, 33, 34, and 35; 31, 32, 33, 34, and 36; 31, 32, 33, 35, and 36; 31, 32, 34, 35, and 36; 31, 33, 34, 35, and 36; or 32, 33, 34, 35, and 36, such as those described above. In one aspect, the variant comprises or consists of the substitutions T/S9G, G/A31D/E, R32L, R33S/N, and L/K/Q34A/P; T/S9G, G/A31D/E, R32L, R33S/N, and E35D/A; T/S9G, G/A31D/E, R32L, R33S/N, and K/R36A; T/S9G, G/A31D/E, R32L, L/K/Q34A/P, and E35D/A; T/S9G, G/A31 D/E, R32L, L/K/Q34A/P, and K/R36A; T/S9G, G/A31 D/E, R32L, E35D/A, and K/R36A; T/S9G, G/A31D/E, R33S/N, L/K/Q34A/P, and E35D/A; T/S9G, G/A31D/E, R33S/N, L/K/Q34A/P, and K/R36A; T/S9G, G/A31D/E, R33S/N, E35D/A, and K/R36A; T/S9G, G/A31D/E, L/K/Q34A/P, E35D/A, and K/R36A; T/S9G, R32L, R33S/N, L/K/Q34A/P, and E35D/A; T/S9G, R32L, R33S/N, L/K/Q34A/P, and K/R36A; T/S9G, R32L, R33S/N, E35D/A, and K/R36A; T/S9G, R32L, L/K/Q34A/P, E35D/A, and K/R36A; T/S9G, R33S/N, L/K/Q34A/P, E35D/A, and K/R36A; G/A31D/E, R32L, R33S/N, L/K/Q34A/P, and E35D/A; G/A31D/E, R32L, R33S/N, L/K/Q34A/P, and K/R36A; G/A31D/E, R32L, R33S/N, E35D/A, and K/R36A; G/A31 D/E, R32L, L/K/Q34A/P, E35D/A, and K/R36A; G/A31 D/E, R33S/N, L/K/Q34A/P, E35D/A, and K/R36A; or R32L, R33S/N, L/K/Q34A/P, E35D/A, and K/R36A. In any of these aspects, the variant may further comprise a deletion at a position corresponding to position 10 of SEQ ID NO: 2.

In another aspect, the variant comprises or consists of substitutions at any six positions corresponding to positions 9, 31, 32, 33, 34, 35 and 36 of SEQ ID NO: 2. For example, the variant may comprise or consist of six substitutions corresponding to positions 9, 31, 32, 33, 34, and 35; 9, 31, 32, 33, 34, and 36; 9, 31, 32, 33, 35, and 36; 9, 31, 32, 34, 35, and 36; 9, 31, 33, 34, 35, and 36; 9, 32, 33, 34, 35, and 36; or 31, 32, 33, 34, 35, and 36, such as those described above. In one aspect, the variant comprises or consists of the substitutions T/S9G, G/A31 D/E, R32L, R33S/N, L/K/Q34A/P, and E35D/A; T/S9G, G/A31D/E, R32L, R33S/N, L/K/Q34A/P, and K/R36A; T/S9G, G/A31D/E, R32L, R33S/N, E35D/A, and K/R36A; T/S9G, G/A31D/E, R32L, L/K/Q34A/P, E35D/A, and K/R36A; T/S9G, G/A31 D/E, R33S/N, L/K/Q34A/P, E35D/A, and K/R36A; T/S9G, R32L, R33S/N, L/K/Q34A/P, E35D/A, and K/R36A; or G/A31D/E, R32L, R33S/N, L/K/Q34A/P, E35D/A, and K/R36A. In any of these aspects, the variant may further comprise a deletion at a position corresponding to position 10 of SEQ ID NO: 2.

In another aspect, the variant comprises or consists of substitutions at all seven positions corresponding to positions 9, 31, 32, 33, 34, 35 and 36 of SEQ ID NO: 2, such as those described above. In one aspect, the variant comprises or consists of the substitutions T/S9G, G/A31 D/E, R32L, R33S/N, L/K/Q34A/P, E35D/A and K/R36A. In either of these aspects, the variant may further comprise a deletion at a position corresponding to position 10 of SEQ ID NO: 2.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a polyhistidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, as described herein, certain amino acid changes are of such a nature that the physico-chemical properties of the polypeptides are altered. For example, the amino acid changes to positions corresponding to any of the positions 9, 31, 32, 33, 34, 35 and 36 of SEQ ID NO: 2 (and an optional deletion at position 10), may alter cofactor specificity, such as increasing the specificity for NAD(H) compared to NADP(H).

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for 3-HPDH activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

For example, essential amino acids of SEQ ID NO: 2 can be identified by analysis of crystallography data described in Yamazawa et al., 2011, *J. Biochem.* 149(6): 701-712 (see Worldwide Protein Data Bank; http://www.wwpdb.org; PDB codes: 3ASU and 3ASV), wherein the active site structure is identified, including the catalytic tetrad at positions 106, 134, 147, and 151. Additional amino acid residues important for enzyme activity are identified therein based on site-directed mutagenesis studies. Similarly, essential amino acids of SEQ ID NO: 6 can be identified by analysis of available crystallography data (see Worldwide Protein Data Bank; http://www.wwpdb.org; PDB code: 3RKU). The identity of corresponding essential amino acids for SEQ ID NO: 4 can be inferred from an alignment with SEQ ID NO: 2 and SEQ ID NO: 6, as shown in FIG. 2.

In some aspects, the variants consist of at least 185 amino acids, e.g., at least 200, 210, 220, 230, or 240 amino acids.

In some embodiments, the variant has increased specificity for NAD(H) compared to NADP(H). In some embodiments, the variant has more than 2-fold, e.g., more than 5-fold, 10-fold, 20-fold, 50-fold, 100-fold, 200-fold, 500-fold, or 1000-fold specificity for NAD(H) compared to NADP(H)

In some embodiments, the variant has one or more improved properties compared to the parent, such as improved catalytic efficiency, improved catalytic rate, improved chemical stability, improved oxidation stability, improved pH activity, improved pH stability, improved specific activity, improved stability under storage conditions, improved substrate binding, improved substrate cleavage, improved substrate specificity, improved substrate stability, improved surface properties, improved thermal activity, and/or improved thermostability.

Parent 3-Hydroxypropionate Dehydrogenases

The parent 3-HPDH may be (a) a polypeptide having at least 60% sequence identity to SEQ ID NO: 2, 4, or 6; (b) a polypeptide encoded by a polynucleotide that hybridizes under low stringency conditions with the full-length complementary strand of SEQ ID NO: 1, 3, or 5; or (c) a polypeptide encoded by a polynucleotide having at least 60% sequence identity to SEQ ID NO: 1, 3, or 5.

In one aspect, the parent 3-HPDH has at least 60%, e.g., at least 65%, at least 70%, at least 75%, at least 80%, at least 85%, at least 90%, at least 95%, at least 96%, at least 97%, at least 98%, at least 99% or 100% sequence identity to SEQ ID NO: 2. In one aspect, the amino acid sequence of the parent differs by up to 10 amino acids, e.g., 1, 2, 3, 4, 5, 6, 7, 8, 9, or 10, from SEQ ID NO: 2. In another aspect, the parent comprises or consists of the amino acid sequence of SEQ ID NO: 2. In another embodiment, the parent is an allelic variant of SEQ ID NO: 2. In another aspect, the parent is a fragment of SEQ ID NO: 2.

In another aspect, the parent 3-HPDH has at least 60%, e.g., at least 65%, at least 70%, at least 75%, at least 80%, at least 85%, at least 90%, at least 95%, at least 96%, at least 97%, at least 98%, at least 99% or 100% sequence identity to SEQ ID NO: 4. In one aspect, the amino acid sequence of the parent differs by up to 10 amino acids, e.g., 1, 2, 3, 4, 5, 6, 7, 8, 9, or 10, from SEQ ID NO: 4. In another aspect, the parent comprises or consists of the amino acid sequence of SEQ ID NO: 4. In another embodiment, the parent is an allelic variant of SEQ ID NO: 4. In another aspect, the parent is a fragment of SEQ ID NO: 4.

In another aspect, the parent 3-HPDH has at least 60%, e.g., at least 65%, at least 70%, at least 75%, at least 80%, at least 85%, at least 90%, at least 95%, at least 96%, at least 97%, at least 98%, at least 99% or 100% sequence identity to SEQ ID NO: 6. In one aspect, the amino acid sequence of the parent differs by up to 10 amino acids, e.g., 1, 2, 3, 4, 5, 6, 7, 8, 9, or 10, from SEQ ID NO: 6. In another aspect, the parent comprises or consists of the amino acid sequence of SEQ ID NO: 6. In another embodiment, the parent is an allelic variant of SEQ ID NO: 6. In another aspect, the parent is a fragment of SEQ ID NO: 6.

In another aspect, the parent is encoded by a polynucleotide that hybridizes under at least low stringency conditions, e.g., medium stringency conditions, medium-high stringency conditions, high stringency conditions, or very high stringency conditions with the full-length complementary strand of SEQ ID NO: 1. (Sambrook et al., 1989, *Molecular Cloning, A Laboratory Manual*, 2d edition, Cold Spring Harbor, N.Y.). In another aspect, the parent is encoded by a polynucleotide that hybridizes under at least low stringency conditions, e.g., medium stringency conditions, medium-high stringency conditions, high stringency conditions, or very high stringency conditions with the full-length complementary strand of SEQ ID NO: 3. In another aspect, the parent is encoded by a polynucleotide that hybridizes under at least low stringency conditions, e.g., medium stringency conditions, medium-high stringency conditions, high stringency conditions, or very high stringency conditions with the full-length complementary strand of SEQ ID NO: 5.

The polynucleotide of SEQ ID NO: 1, 3, 5, or a subsequence thereof, as well as the polypeptide of SEQ ID NO: 2, 4, 6, or a fragment thereof, may be used to design nucleic acid probes to identify and clone DNA encoding a parent from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin).

A genomic DNA or cDNA library prepared from such other strains may be screened for DNA that hybridizes with the probes described above and encodes a parent. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1, 3, 5, or a subsequence thereof, the carrier material is used in a Southern blot.

In one aspect, the nucleic acid probe is a polynucleotide having SEQ ID NO: 1, 3, or 5. In another aspect, the nucleic acid probe is a polynucleotide that encodes the polypeptide of SEQ ID NO: 2, 4, 6; or a fragment thereof.

In another embodiment, the parent is encoded by a polynucleotide having at least 60%, e.g., at least 65%, at least 70%, at least 75%, at least 80%, at least 85%, at least 90%, at least 95%, at least 96%, at least 97%, at least 98%, at least 99%, or 100% sequence identity to SEQ ID NO: 1. In another embodiment, the parent is encoded by a polynucleotide having at least 60%, e.g., at least 65%, at least 70%, at least 75%, at least 80%, at least 85%, at least 90%, at least 95%, at least 96%, at least 97%, at least 98%, at least 99%, or 100% sequence identity to SEQ ID NO: 3. In another embodiment, the parent is encoded by a polynucleotide having at least 60%, e.g., at least 65%, at least 70%, at least 75%, at least 80%, at least 85%, at least 90%, at least 95%, at least 96%, at least 97%, at least 98%, at least 99%, or 100% sequence identity to SEQ ID NO: 5.

The polypeptide may be a hybrid polypeptide in which a region of one polypeptide is fused at the N-terminus or the C-terminus of a region of another polypeptide.

The parent may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

The parent may be obtained from microorganisms of any genus. For purposes of the present invention, the term "obtained from" as used herein in connection with a given source shall mean that the parent encoded by a polynucleotide is produced by the source or by a strain in which the polynucleotide from the source has been inserted. In one aspect, the parent is secreted extracellularly.

The parent may be a bacterial 3-HPDH. For example, the parent may be a Gram-positive bacterial polypeptide such as a *Bacillus*, *Clostridium*, *Enterococcus*, *Geobacillus*, *Lactobacillus*, *Lactococcus*, *Oceanobacillus*, *Staphylococcus*, *Streptococcus*, or *Streptomyces* 3-HPDH, or a Gram-negative bacterial polypeptide such as a *Campylobacter*, *E. coli*, *Flavobacterium*, *Fusobacterium*, *Helicobacter*, *Ilyobacter*, *Neisseria*, *Pseudomonas*, *Salmonella*, or *Ureaplasma* 3-HPDH.

In one aspect, the parent is a *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, or *Bacillus thuringiensis* 3-HPDH.

In another aspect, the parent is a *Streptococcus equisimilis*, *Streptococcus pyogenes*, *Streptococcus uberis*, or *Streptococcus equi* subsp. *Zooepidemicus* 3-HPDH.

In another aspect, the parent is a *Streptomyces achromogenes*, *Streptomyces avermitilis*, *Streptomyces coelicolor*, *Streptomyces griseus*, or *Streptomyces lividans* 3-HPDH.

The parent may be a fungal 3-HPDH. For example, the parent may be a yeast 3-HPDH such as a *Candida*, *Kluyveromyces*, *Pichia*, *Saccharomyces*, *Schizosaccharomyces*, *Yarrowia* or *Issatchenkia* 3-HPDH; or a filamentous fungal 3-HPDH such as an *Acremonium*, *Agaricus*, *Alternaria*, *Aspergillus*, *Aureobasidium*, *Botryosphaeria*, *Ceriporiopsis*,

*Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella,* or *Xylaria* 3-HPDH.

In another aspect, the parent is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* 3-HPDH.

In another aspect, the parent is an *Acremonium cellulolyticus, Aspergillus aculeatus, Aspergillus awamori, Aspergillus foetidus, Aspergillus fumigatus, Aspergillus japonicus, Aspergillus nidulans, Aspergillus niger, Aspergillus oryzae, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia setosa, Thielavia spededonium, Thielavia subthermophila, Thielavia terrestris, Trichoderma harzianum, Trichoderma koningii, Trichoderma longibrachiatum, Trichoderma reese,* or *Trichoderma viride* 3-HPDH.

In one aspect, the parent 3-HPDH is from *E. coli*, such as the *E. coli* 3-HPDH of SEQ ID NO: 2. In another aspect, the parent 3-HPDH is from *Issatchenkia*, such as the *Issatchenkia orientalis* 3-HPDH of SEQ ID NO: 4. In another aspect, the parent 3-HPDH is from *Saccharomyces*, such as the *Saccharomyces cerevisiae* 3-HPDH of SEQ ID NO: 6.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The parent may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding a parent may then be obtained by similarly screening a genomic DNA or cDNA library of another microorganism or mixed DNA sample. Once a polynucleotide encoding a parent has been detected with the probe(s), the polynucleotide can be isolated or cloned by utilizing techniques that are known to those of ordinary skill in the art (see, e.g., Sambrook et al., 1989, supra).

Preparation of Variants

Also described are methods for obtaining a variant having 3-HPDH activity, comprising: (a) introducing into a parent 3-HPDH a substitution at one or more (e.g., two, several) positions corresponding to positions 9, 31, 32, 33, 34, 35, and 36 of SEQ ID NO: 2; and (b) recovering the variant.

The variants can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (e.g., several) mutations are introduced at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., U.S. Patent Application Publication No. 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Any site-directed mutagenesis procedure can be used to prepare the variants described herein. For example, there are many commercial kits available that can be used.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-

896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Polynucleotides, Nucleic Acid Constructs, and Expression Vectors

In one aspect are polynucleotides (e.g., isolated polynucleotides) encoding the polypeptides and variants described herein, as well as nucleic acid constructs and expression vectors comprising the polynucleotides.

The nucleic acid constructs comprise a polynucleotide encoding a polypeptide or variant described herein operably linked to one or more control sequences that direct the expression of the coding sequence in a suitable host cell under conditions compatible with the control sequences.

The polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide which is recognized by a host cell for expression of the polynucleotide. The promoter contains transcriptional control sequences that mediate the expression of the variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol 3-hydroxypropionate dehydrogenase/ glyceraldehyde-3-phosphate 3-hydroxypropionate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator sequence is operably linked to the 3'-terminus of the polynucleotide encoding the variant. Any terminator that is functional in the host cell may be used.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate 3-hydroxypropionate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader sequence is operably linked to the 5'-terminus of the polynucleotide encoding the variant. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol 3-hydroxypropionate dehydrogenase/glyceraldehyde-3-phosphate 3-hydroxypropionate dehydrogenase (ADH2/GAP).

The control sequence may also be a polyadenylation sequence, a sequence operably linked to the 3'-terminus of the variant-encoding sequence and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a variant and directs the variant into the cell's secretory pathway. The 5'-end of the coding sequence of the polynucleotide may inherently contain a signal peptide coding sequence naturally linked in translation reading frame with the segment of the coding sequence that encodes the variant. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the variant. However, any signal peptide coding sequence that directs the expressed variant into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a variant. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of the variant and the signal peptide sequence is positioned next to the N-terminus of the propeptide sequence.

It may also be desirable to add regulatory sequences that regulate expression of the variant relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the variant would be operably linked with the regulatory sequence.

Recombinant expression vectors comprise a polynucleotide encoding a polypeptide or variant described herein, a promoter, and transcriptional and translational stop signals. The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

The vector preferably contains an element(s) that permits integration of the vector into the host cell's genome or autonomous replication of the vector in the cell independent of the genome.

For integration into the host cell genome, the vector may rely on the polynucleotide's sequence encoding the variant or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMR1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells comprising a polynucleotide encoding a polypeptide or variant described herein operably linked to one or more control sequences that direct production, e.g., for use in an active 3-HP pathway. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication.

In some aspects, a host cell may be selected for the recombinant production and recovery of the polypeptide or variant described herein. In other aspects, the host cell comprises an active 3-HP pathway and is chosen to express the polypeptide or variant described herein as a 3-HP pathway gene in the recombinant production of 3-HP by the cell (e.g., as described in WO2012/074818, the content of which is hereby incorporated by reference). Such cells can produce 3-HP from a fermentable sugar or a malonyl semialdehyde precursor.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell, including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacte-* riol. 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397), or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804) or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., *In, Ainsworth and Bisby's Dictionary of The Fungi*, 8th edition, 1995, CAB International, University Press, Cambridge, UK). The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, *Soc. App. Bacteriol. Symposium Series No.* 9, 1980).

The yeast host cell may be a *Candida, Hansenula, Kluyveromyces, Pichia, Saccharomyces, Schizosaccharomyces,* or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis,* or *Yarrowia lipolytica* cell.

In some aspects, the host cell is selected from *Issatchenkia, Candida, Kluyveromyces, Pichia, Schizosaccharomyces, Torulaspora, Zygosaccharomyces*, and *Saccharomyces*. In some aspects, the host cell is a *I. orientalis, C. lambica,* or *S. bulderi* host cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

In some aspects, the host cell comprises an active 3-HP pathway which includes a polynucleotide that encodes a polypeptide or variant described herein and is capable of producing 3-HP from a fermentable sugar (e.g., glucose) or pyruvate. Active 3-HP pathways such as the pathway shown in FIG. 1 are known in the art (see, for example, WO2012/074818, the content of which is hereby incorporated by reference). The host cell may comprises PEP carboxylase activity or pyruvate carboxylase activity; aspartate aminotransferase activity; aspartate decarboxylase activity; and beta-alanine/alpha-ketoglutarate aminotransferase (BAAT) activity. (see, for example, WO02/42418 and WO2008/027742, the content of which is hereby incorporated by reference). Such enzyme activities may result from endogenous gene expression, expression of heterologous polynucleotides encoding the enzymes in the metabolic pathway, or from a combination of endogenous gene expression supplemented with expression of one or more (e.g., two, several) heterologous polynucleotides. In some embodiments, the host cell comprises a heterologous polynucleotide that encodes a PEP carboxylase, a heterologous polynucleotide that encodes a pyruvate carboxylase, a heterologous polynucleotide that encodes a aspartate aminotransferase, a heterologous polynucleotide that encodes a aspartate decarboxylase, and/or a heterologous polynucleotide that encodes a BAAT.

In some aspects, the host cell is a 3-HP resistant host cell. A "3-HP-resistant host cell" as used herein refers to a host cell that exhibits an average glycolytic rate of at least 2.5 g/L/hr in media containing 75 g/L or greater 3-HP at a pH of less than 4.0. Such rates and conditions represent an economic process for producing 3-HP. In certain of these embodiments, the host cells may exhibit 3-HP resistance in their native form. In other embodiments, the cells may have undergone mutation and/or selection before, during, or after introduction of genetic modifications related to an active 3-HP fermentation pathway, such that the mutated and/or selected cells possess a higher degree of resistant to 3-HP than wild-type cells of the same species. In certain embodiments, mutation and/or selection may be carried out on cells that exhibit 3-HP resistance in their native form. Cells that have undergone mutation and/or selection may be tested for sugar consumption and other characteristics in the presence of varying levels of 3-HP in order to determine their potential as industrial hosts for 3-HP production. In addition to 3-HP resistance, the host cells provided herein may have undergone mutation and/or selection for resistance to one or more additional organic acids or to other fermentation products, byproducts, or media components.

Selection for resistance to 3-HP or to other compounds may be accomplished using methods well known in the art. For example, selection may be carried out using a chemostat. A chemostat is a device that allows for a continuous culture of microorganisms (e.g., yeast) wherein the specific growth rate and cell number can be controlled independently. A continuous culture is essentially a flow system of constant volume to which medium is added continuously and from which continuous removal of any overflow can occur. Once such a system is in equilibrium, cell number and nutrient status remain constant, and the system is in a steady state. A chemostat allows control of both the population density and the specific growth rate of a culture through dilution rate and alteration of the concentration of a limiting nutrient, such as a carbon or nitrogen source. By altering the conditions as a culture is grown (e.g., decreasing the concentration of a secondary carbon source necessary to the growth of the inoculum strain, among others), microorganisms in the population that are capable of growing faster at the altered conditions will be selected and will outgrow microorganisms that do not function as well under the new conditions. Typically such selection requires the progressive increase or decrease of at least one culture component over the course of growth of the chemostat culture. The operation of chemostats and their use in the directed evolution of microorganisms is well known in the art (see, e.g., Novick Proc Natl Acad Sci USA 36:708-719 (1950), Harder J Appl Bacteriol 43:1-24 (1977).

In some aspects, the host cell secretes (and/or is capable of secreting) an increased level of 3-HP compared to the host cell without the polynucleotide that encodes the polypeptide or variant described herein when cultivated under the same conditions. In some embodiments, the host cell secretes and/or is capable of secreting an increased level of 3-HP of at least 5%, e.g., at least 10%, at least 15%, at least 20%, at least 25%, at least 50%, at least 100%, at least 150%, at least 200%, at least 300%, or at 500% compared to the host cell without the polynucleotide that encodes the polypeptide or variant described herein, when cultivated under the same conditions. Examples of suitable cultivation conditions are described below and will be readily apparent to one of skill in the art based on the teachings herein. In some embodiments, the host cell produces (and/or is capable of producing) 3-HP at a yield of at least than 10%, e.g., at least than 20%, at least than 30%, at least than 40%, at least than 50%, at least than 60%, at least than 70%, at least than 80%, or at least than 90%, of theoretical. In some embodiments, the host cell has a 3-HP volumetric productivity greater than about 0.1 g/L per hour, e.g., greater than about 0.2 g/L per hour, 0.5 g/L per hour, 0.6 g/L per hour, 0.7 g/L per hour, 0.8 g/L per hour, 0.9 g/L per hour, 1.0 g/L per hour, 1.1 g/L per hour, 1.2 g/L per hour, 1.3 g/L per hour, 1.5 g/L per hour, 1.75 g/L per hour, 2.0 g/L per hour, 2.25 g/L per hour, 2.5 g/L per hour, or 3.0 g/L per hour; or between about 0.1 g/L per hour and about 2.0 g/L per hour, e.g., between about 0.3 g/L per hour and about 1.7 g/L per hour, about 0.5 g/L per hour and about 1.5 g/L per hour, about 0.7 g/L per hour and about 1.3 g/L per hour, about 0.8 g/L per hour and about 1.2 g/L per hour, or about 0.9 g/L per hour and about 1.1 g/L per hour.

The host cells may be cultivated in a nutrient medium suitable for production of the polypeptides and variants described herein using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the desired polypeptide to be expressed and/or isolated. The cultivation takes place in a suitable nutrient medium comprising carbon and nitrogen sources and inorganic salts, as described herein, using procedures known in the art. Suitable media are available from commercial suppliers, may be prepared according to published compositions (e.g., in catalogues of the American Type Culture Collection), or may be prepared from commercially available ingredients.

As described supra, enzyme activities of the enzymes described herein can be detected using methods known in the art. These detection methods may include use of specific antibodies, formation of an enzyme product, or disappearance of an enzyme substrate. See, for example, Sambrook et al., *Molecular Cloning: A Laboratory Manual*, Third Ed., Cold Spring Harbor Laboratory, New York (2001); Ausubel et al., *Current Protocols in Molecular Biology*, John Wiley and Sons, Baltimore, Md. (1999); and Hanai et al., *Appl. Environ. Microbiol.* 73:7814-7818 (2007)).

Methods of Production

The present invention also relates to methods of producing a polypeptide or variant described herein, comprising: (a) cultivating a host cell comprising a polynucleotide encoding the polypeptide or variant under conditions suitable for expression; and (b) recovering the polypeptide or variant.

The host cells are cultivated in a nutrient medium suitable for production of the polypeptide or variant described herein using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variant may be detected using methods known in the art that are specific for the variants. These detection methods include, but are not limited to, use of specific antibodies, formation of an enzyme product, or disappearance of an enzyme substrate. For example, an enzyme assay, such as the assays described in the Examples section, may be used to determine the enzymatic activity.

The polypeptide or variant may be recovered using methods known in the art. For example, the variant may be recovered from the nutrient medium by conventional procedures including, but not limited to, collection, centrifugation, filtration, extraction, spray-drying, evaporation, or precipitation.

The polypeptide or variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure variants.

In an alternative aspect, the polypeptide or variant is not recovered, but rather a host cell expressing the polypeptide is used as part of a metabolic pathway, as described herein for the production of 3-HP.

Methods of Producing 3-HP

The host cells described herein may be used for the production of 3-HP. In one aspect is a method of producing 3-HP from a fermentable sugar (e.g., glucose) or pyruvate, comprising: (a) cultivating any one of the host cells described herein (e.g., a host cell that comprises an active 3-HP pathway and a polynucleotide that encodes a 3-HPDH described herein) in a medium under suitable conditions to produce the 3-HP; and (b) recovering the 3-HP. In some embodiments of the method, the host cell further comprises PEP carboxylase activity or pyruvate carboxylase activity; aspartate aminotransferase activity; aspartate decarboxylase activity; and beta-alanine/alpha-ketoglutarate aminotransferase (BAAT) activity. In some embodiments, the host cell comprises a heterologous polynucleotide that encodes a PEP carboxylase, a heterologous polynucleotide that encodes a pyruvate carboxylase, a heterologous polynucleotide that encodes an aspartate aminotransferase, a heterologous polynucleotide that encodes a aspartate decarboxylase, and/or a heterologous polynucleotide that encodes a BAAT. In some embodiments of the methods, the host cells are 3-HP resistant host cells, as described supra.

In one aspect is a method of producing 3-HP from a fermentable sugar (e.g., glucose) or pyruvate, comprising: (a) cultivating any one of the host cells described herein (e.g., a host cell that comprises an active 3-HP pathway and a polynucleotide that encodes a 3-HPDH variant of SEQ ID NO: 2, 4, or 6 described herein) in a medium under suitable conditions to produce the 3-HP; and (b) recovering the 3-HP. In some embodiments of the method, the 3-HPDH variant has at least 60%, e.g., at least 65%, at least 70%, at least 75%, at least 80%, at least 85%, at least 90%, at least 95%, at least 96%, at least 97%, at least 98%, at least 99% or 100% sequence identity to SEQ ID NO: 2, 4, or 6. In some embodiments, the host cell further comprises PEP carboxylase activity or pyruvate carboxylase activity; aspartate aminotransferase activity; aspartate decarboxylase activity; and beta-alanine/alpha-ketoglutarate aminotransferase (BAAT) activity. In some embodiments, the host cell comprises a heterologous polynucleotide that encodes a PEP carboxylase, a heterologous polynucleotide that encodes a pyruvate carboxylase, a heterologous polynucleotide that encodes a aspartate aminotransferase, a heterologous polynucleotide that encodes a aspartate decarboxylase, and/or a heterologous polynucleotide that encodes a BAAT. In some embodiments of the methods, the host cells are 3-HP resistant host cells, as described supra.

In one aspect is a method of producing 3-HP from a fermentable sugar (e.g., glucose) or pyruvate, comprising: (a) cultivating any one of the host cells described herein (e.g., a host cell that comprises an active 3-HP pathway and a polynucleotide that encodes a 3-HPDH related to SEQ ID NO: 82) in a medium under suitable conditions to produce the 3-HP; and (b) recovering the 3-HP. In some embodiments of the method, the 3-HPDH has at least 60%, e.g., at least 65%, at least 70%, at least 75%, at least 80%, at least 85%, at least 90%, at least 95%, at least 96%, at least 97%, at least 98%, at least 99% or 100% sequence identity to the *P. putida* 3-HPDH of SEQ ID NO: 82. In some embodiments, the host cell further comprises PEP carboxylase activity or pyruvate carboxylase activity; aspartate aminotransferase activity; aspartate decarboxylase activity; and beta-alanine/alpha-ketoglutarate aminotransferase (BAAT) activity. In some embodiments, the host cell comprises a heterologous polynucleotide that encodes a PEP carboxylase, a heterologous polynucleotide that encodes a pyruvate carboxylase, a heterologous polynucleotide that encodes an aspartate aminotransferase, a heterologous polynucleotide that encodes a aspartate decarboxylase, and/or a heterologous polynucleotide that encodes a BAAT. In some embodiments of the methods, the host cells are 3-HP resistant host cells, as described supra.

Methods for the production of 3-HP may be performed in a fermentable medium comprising any one or more (e.g., two, several) sugars, such as glucose, fructose, sucrose, cellobiose, xylose, xylulose, arabinose, mannose, galactose, and/or soluble oligosaccharides. In some instances, the fermentation medium is derived from a natural source, such as sugar cane, starch, or cellulose, and may be the result of pretreating the source by enzymatic hydrolysis (saccharification).

In addition to the appropriate carbon sources from one or more (e.g., two, several) sugar(s), the fermentable medium may contain other nutrients or stimulators known to those skilled in the art, such as macronutrients (e.g., nitrogen sources) and micronutrients (e.g., vitamins, mineral salts, and metallic cofactors). In some aspects, the carbon source can be preferentially supplied with at least one nitrogen source, such as yeast extract, $N_2$, peptone (e.g., Bacto™ Peptone), or soytone (e.g., Bacto™ Soytone). Nonlimiting examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. Examples of mineral salts and metallic cofactors include, but are not limited to Na, P, K, Mg, S, Ca, Fe, Zn, Mn, and Cu.

Suitable conditions used for the methods of 3-HP production may be determined by one skilled in the art in light of the teachings herein. In some aspects of the methods, the host cells are cultivated for about 12 hours to about 216 hours, such as about 24 hours to about 144 hours, or about 36 hours to about 96 hours. The temperature is typically between about 26° C. to about 60° C., e.g., about 34° C. to about 50° C., and at a pH of about 3.0 to about 8.0, such as about 3.0 to about 7.0, about 3.0 to about 6.0, about 3.0 to about 5.0, about 3.5 to about 4.5, about 4.0 to about 8.0, about 4.0 to about 7.0, about 4.0 to about 6.0, about 4.0 to about 5.0, about 5.0 to about 8.0, about 5.0 to about 7.0, or about 5.0 to about 6.0. In some aspects of the methods, the resulting intracellular pH of the host cell is about 3.0 to about 8.0, such as about 3.0 to about 7.0, about 3.0 to about 6.0, about 3.0 to about 5.0, about 3.5 to about 4.5, about 4.0 to about 8.0, about 4.0 to about 7.0, about 4.0 to about 6.0, about 4.0 to about 5.0, about 5.0 to about 8.0, about 5.0 to about 7.0, or about 5.0 to about 6.0. Cultivation may be performed under anaerobic, microaerobic, or aerobic conditions, as appropriate. In some aspects, the cultivation is performed under anaerobic conditions. Suitable buffering agents are known in the art.

Cultivation may be performed under anaerobic, substantially anaerobic (microaerobic), or aerobic conditions, as appropriate. Briefly, anaerobic refers to an environment devoid of oxygen, substantially anaerobic (microaerobic) refers to an environment in which the concentration of oxygen is less than air, and aerobic refers to an environment wherein the oxygen concentration is approximately equal to or greater than that of the air. Substantially anaerobic conditions include, for example, a culture, batch fermentation or continuous fermentation such that the dissolved oxygen concentration in the medium remains less than 10% of saturation. Substantially anaerobic conditions also includes growing or resting cells in liquid medium or on solid agar inside a sealed chamber maintained with an atmosphere of less than 1% oxygen. The percent of oxygen can be maintained by, for example, sparging the culture with an $N_2/CO_2$ mixture or other suitable non-oxygen gas or gases. In some embodiments, the cultivation is performed under anaerobic conditions or substantially anaerobic conditions.

The methods of described herein can employ any suitable fermentation operation mode. For example, a batch mode fermentation may be used with a close system where culture media and host microorganism, set at the beginning of fermentation, have no additional input except for the reagents certain reagents, e.g., for pH control, foam control or others required for process sustenance. The process described herein can also be employed in Fed-batch or continuous mode.

The methods described herein may be practiced in several bioreactor configurations, such as stirred tank, bubble column, airlift reactor and others known to those skilled in the art.

The methods may be performed in free cell culture or in immobilized cell culture as appropriate. Any material support for immobilized cell culture may be used, such as alginates, fibrous bed, or argyle materials such as chrysotile, montmorillonite KSF and montmorillonite K-10.

In one aspect of the methods, the 3-HP is produced at a titer greater than about 10 g/L, e.g., greater than about 25 g/L, 50 g/L, 75 g/L, 100 g/L, 125 g/L, 150 g/L, 160 g/L, 170 g/L, 180 g/L, 190 g/L, 200 g/L, 210 g/L, 225 g/L, 250 g/L, 275 g/L, 300 g/L, 325 g/L, 350 g/L, 400 g/L, or 500 g/L; or between about 10 g/L and about 500 g/L, e.g., between about 50 g/L and about 350 g/L, about 100 g/L and about 300 g/L, about 150 g/L and about 250 g/L, about 175 g/L and about 225 g/L, or about 190 g/L and about 210 g/L. In one aspect of the methods, the 3-HP is produced at a titer greater than about 0.01 gram per gram of carbohydrate, e.g., greater than about 0.02, 0.05, 0.75, 0.1, 0.2, 0.3, 0.4, 0.5, 0.6, 0.7, 0.8, 0.9, or 1.0 gram per gram of carbohydrate.

In one aspect of the methods, the amount of produced 3-HP is at least 5%, e.g., at least 10%, at least 15%, at least 20%, at least 25%, at least 30%, at least 50%, or at least 100% greater compared to cultivating the host cell without the polynucleotide that encodes a 3-HPDH under the same conditions.

The recombinant 3-HP can be optionally recovered and purified from the fermentation medium using any procedure known in the art including, but not limited to, chromatography (e.g., size exclusion chromatography, adsorption chromatography, ion exchange chromatography), electrophoretic procedures, differential solubility, distillation, extraction (e.g., liquid-liquid extraction), pervaporation, extractive filtration, membrane filtration, membrane separation, reverse osmosis, ultrafiltration, or crystallization.

In some aspects of the methods, the recombinant 3-HP before and/or after being optionally purified is substantially pure. With respect to the methods of producing 3-HP, "substantially pure" intends a recovered preparation of 3-HP that contains no more than 15% impurity, wherein impurity intends compounds other than 3-HP. In one variation, a preparation of substantially pure 3-HP is provided wherein the preparation contains no more than 25% impurity, or no more than 20% impurity, or no more than 10% impurity, or no more than 5% impurity, or no more than 3% impurity, or no more than 1% impurity, or no more than 0.5% impurity.

Suitable assays to test for the production of 3-HP for the methods of production and host cells described herein can be performed using methods known in the art. For example, the final 3-HP (and other organic compounds) can be analyzed by methods such as HPLC (High Performance Liquid Chromatography), GC-MS (Gas Chromatography Mass Spectroscopy) and LC-MS (Liquid Chromatography-Mass Spectroscopy) or other suitable analytical methods using routine procedures well known in the art. The release of 3-HP in the fermentation broth can also be tested with the culture supernatant. Byproducts and residual sugar in the fermentation medium (e.g., glucose) can be quantified by HPLC using, for example, a refractive index detector for glucose and alcohols, and a UV detector for organic acids (Lin et al., *Biotechnol. Bioeng.* 90:775-779 (2005)), or using other suitable assay and detection methods well known in the art.

Plants

Also described are plants, e.g., transgenic plants, plant parts, or plant cells, comprising a polynucleotide described herein so as to express and produce the polypeptides and variants described herein in recoverable quantities.

The transgenic plant can be dicotyledonous (a dicot) or monocotyledonous (a monocot). Examples of monocot plants are grasses, such as meadow grass (blue grass, Poa), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

The transgenic plant or plant cell expressing a variant may be constructed in accordance with methods known in the art. In short, the plant or plant cell is constructed by incorporating one or more expression constructs encoding a variant into the plant host genome or chloroplast genome and propagating the resulting modified plant or plant cell into a transgenic plant or plant cell.

The expression construct is conveniently a nucleic acid construct that comprises a polynucleotide encoding a variant operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the variant is desired to be expressed. For instance, the expression of the gene encoding a variant may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, or the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the chlorella virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may be induced by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a variant in the plant. For instance, the promoter enhancer element may be an intron that is placed between the promoter and the polynucleotide encoding a variant. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

*Agrobacterium tumefaciens*-mediated gene transfer is a method for generating transgenic dicots (for a review, see Hooykas and Schilperoort, 1992, *Plant Mol. Biol.* 19: 15-38) and for transforming monocots, although other transformation methods may be used for these plants. A method for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct of the present invention, transgenic plants may be made by crossing a plant having the construct to a second plant lacking the construct. For example, a construct encoding a variant can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention. Crossing results in the introduction of a transgene into a plant line by cross pollinating a starting line with a donor plant line. Non-limiting examples of such steps are described in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

In one aspect is a method of producing a polypeptide or variant described herein comprising: (a) cultivating a transgenic plant or a plant cell comprising a polynucleotide encoding the polypeptide or variant under conditions conducive for production; and (b) recovering the polypeptide or variant.

The present invention is further described by the following examples that should not be construed as limiting the scope of the invention.

EXAMPLES

Chemicals used as buffers and substrates were commercial products of at least reagent grade.

Strains

The *E. coli* strain MG1655 (NN059268) was used as the source of DNA encoding the ydfG 3-HPDH gene. Strains MG1655, SoloPack Gold (Agilent Technologies, Inc., Santa Clara, Calif., USA), and SURE cells (Agilent Technologies, Inc.) were used to express the ydfG plasmids.

The *I. orientalis* strain MBin500 was used as the source of DNA encoding the *I. orientalis* YMR226c 3-HPDH gene, as described in WO2012/074818. *I. orientalis* strain McTs259 (WO2012/074818) was used to express the described 3-HPDH genes for 3-HP production.

Media

LB medium was composed of 10 g of tryptone, 5 g of yeast extract, 5 g of sodium chloride, and deionized water to 1 liter.

2XYT plates were composed of 16 g of tryptone, 10 g of yeast extract, 5 g of NaCl, 15 g of Bacto agar, and deionized water to 1 liter.

TABLE 0

Primer Sequences

| Identifier | SEQ ID | Sequence (5'-3') |
|---|---|---|
| 000001 | 15 | CGGAATTCATGATCGTTTTAGTAACTGGAGC |
| 000002 | 16 | CGGGATCCTTACTGACGGTGGACATTCAG |
| 614464 | 34 | TCGCCACTGATCTGAACCCGGAAGCGTTGCAGGAGTTAAAAGA |
| 614465 | 35 | TCTTTTAACTCCTGCAACGCTTCCGGGTTCAGATCAGTGGCGA |
| 614466 | 36 | CCACTGATCTGAACCCGGCCCGGTTGCAGGAGTTAAAAGACGA |
| 614467 | 37 | TCGTCTTTTAACTCCTGCAACCGGGCCGGGTTCAGATCAGTGG |
| 614468 | 38 | GGCATAAAGTTATCGCCACTGGCCTGAACCCGGCCGCGTTGCA |
| 614469 | 39 | TGCAACGCGGCCGGGTTCAGGCCAGTGGCGATAACTTTATGCC |
| 614470 | 40 | TCGTTTTAGTAACTGGAGCAACGGCAGGTTTTGGTGAATGCATT |
| 614471 | 41 | AATGCATTCACCAAAACCTGCCGTTGCTCCAGTTACTAAAACGA |
| 614472 | 42 | ATAAAGTTATCGCCACTGATCGTAACCCGGCCGCGTTGCAGGA |
| 614473 | 43 | TCCTGCAACGCGGCCGGGTTACGATCAGTGGCGATAACTTTAT |
| 614476 | 44 | AACTCCTGCAACGCGGCCGGGCGCAGATCAGTGGCGATAACTT |
| 614477 | 45 | AAGTTATCGCCACTGATCTGCGCCCGGCCGCGTTGCAGGAGTT |
| 614479 | 46 | TTATCGCCACTGATCTGAACCAGGCCGCGTTGCAGGAGTTAAA |
| 614480 | 47 | TTTAACTCCTGCAACGCGGCCTGGTTCAGATCAGTGGCGATAA |
| 614546 | 48 | TAAAGTTATCGCCACTGATCTGCGCCCGGAAGCGTTGCAGGAGTTAAAAGACG |
| 614547 | 49 | CGTCTTTTAACTCCTGCAACGCTTCCGGGCGCAGATCAGTGGCGATAACTTTA |
| 614548 | 50 | AGTTATCGCCACTGATCTGCGCCAGGCCGCGTTGCAGGAGTTAAAAGACGAAC |
| 614549 | 51 | GTTCGTCTTTTAACTCCTGCAACGCGGCCTGGCGCAGATCAGTGGCGATAACT |
| 614550 | 52 | GCATAAAGTTATCGCCACTGATCTGCGCCAGGAAGCGTTGCAGGAGTTAAAGACGAAC |
| 614551 | 53 | GTTCGTCTTTTAACTCCTGCAACGCTTCCTGGCGCAGATCAGTGGCGATAACTTTATGC |
| 614552 | 54 | GCATAAAGTTATCGCCACTGATCTGAACCAGGAAGCGTTGCAGGAGTTAAAG |
| 614553 | 55 | CTTTTAACTCCTGCAACGCTTCCTGGTTCAGATCAGTGGCGATAACTTTATGC |
| 614697 | 56 | GTCATCGTAGTCTAGATAAAATGATCGTTTTGGTCACCGG |
| 614698 | 57 | GTGCTCCATTAATTAATTATTGTCTGTG |
| 614967 | 58 | GCGGAATTCATGTTTGGTAATATTTCCCAA |

TABLE 0-continued

Primer Sequences

| Identifier | SEQ ID | Sequence (5'-3') |
|---|---|---|
| 614968 | 59 | GATCCCGGGCTATTTATCTAATGATCCTC |
| 614973 | 60 | GTTTTAGTAACTGGAGCAGGCGCAGGTTTTGGTGAATGC |
| 614974 | 61 | GCATTCACCAAAACCTGCGCCTGCTCCAGTTACTAAAAC |
| 614975 | 62 | CATAAAGTTATCGCCACTGATCGTCGCCAGGAACGGTTG |
| 614976 | 63 | CAACCGTTCCTGGCGACGATCAGTGGCGATAACTTTATG |
| 614977 | 64 | TAAAGTTATCGCCACTGATCGTCGCCAGGAAGCGTTGCAG |
| 614978 | 65 | CTGCAACGCTTCCTGGCGACGATCAGTGGCGATAACTTTA |
| 614979 | 66 | ACTGATCTGCGCCAGGAACGGTTGCAGGAGTTAAAAGAC |
| 614980 | 67 | GTCTTTTAACTCCTGCAACCGTTCCTGGCGCAGATCAGT |
| 615004 | 68 | ATCCTAATTACAGGTGCGGGTACTGGTATCGGATACCAT |
| 615005 | 69 | ATGGTATCCGATACCAGTACCCGCACCTGTAATTAGGAT |
| 615006 | 70 | TTGAAGTTGGTTTTGGCTGATTTAAGAAAGGAGAAGCTGGAG |
| 615007 | 71 | CTCCAGCTTCTCCTTTCTTAAATCAGCCAAAACCAACTTCAA |
| 615428 | 72 | TTGCAGGCAAGAACATCCTAATTACAGGTGC |
| 615429 | 73 | GCACCTGTAATTAGGATGTTCTTGCCTGCAA |
| 615485 | 74 | GTAGCTAGCTAAAATGTTTGGTAATATTTCCCA |
| 615486 | 75 | TGCTTAATTAACTATTTATCTAATGATCCTC |
| 615890 | 76 | TTGGTCACCGGTGCAGGTGCAGGTTTCGGCGAA |
| 615891 | 77 | TTCGCCGAAACCTGCACCTGCACCGGTGACCAA |
| 615892 | 78 | ACAAGGTTATCGCTACCGACTTGAGACAAGAGAGATTGCA |
| 615893 | 79 | TGCAATCTCTCTTGTCTCAAGTCGGTAGCGATAACCTTGT |

Example 1

Construction of an Expression Vector for the E. Coli ydfG 3-HPDH Gene

Figure 4:
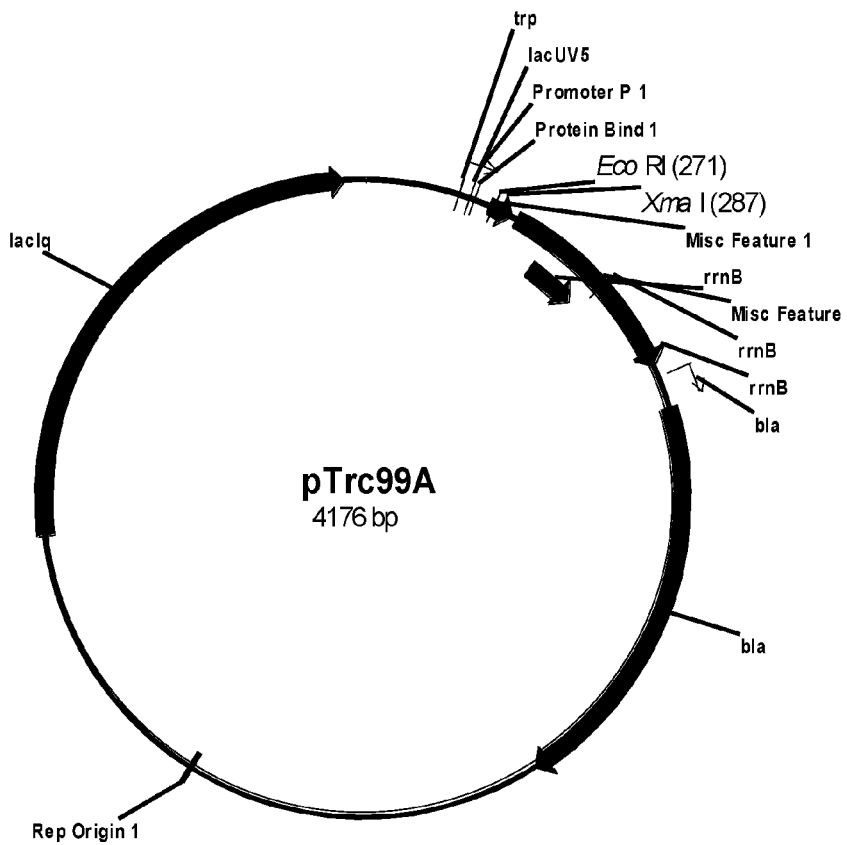
FIG. 4 shows plasmid map for pTrc99A.

The E. coli ydfG 3-HPDH coding sequence was amplified by PCR using two synthetic oligonucleotide primers designed to generate an EcoRI restriction site at the 5' end and a BamHI restriction site at the 3' end for integration into pTrc99A (FIG. 4; see Amann, E., et al. (1988). "Tightly regulated tac promoter vectors useful for the expression of unfused and fused proteins in Escherichia coli." Gene 69(2): 301-315).

E. coli genomic DNA for PCR was obtained by isolating a single colony of E. coli MG1655 from a 2XYT plate and dissolving into 25 µl 1% Triton X-100, 20 mM Tris pH 8.5, 2 mM EDTA (CLS solution), heated at 80° C. for 10 minutes and then cooled on ice. Three microliters of this solution used as a template in a PCR reaction further containing 1× Pfx Amplification buffer, fifty picomoles each of primers 000001 and 000002, 0.2 mM each of dATP, dGTP, dCTP, and dTTP, and 2.5 units Platinum® Pfx DNA Polymerase (Invitrogen, Carlsbad, Calif., USA) in a final volume of 50 µl. The amplification reaction was performed in an EPPENDORF® MASTERCYCLER® 5333 (Eppendorf Scientific, Inc., Westbury, N.Y., USA) programmed for one cycle at 95° C. for 2 minutes; and 25 cycles each at 95° C. for 30 seconds, 55° C. for 30 seconds, and 72° C. for 1 minute. After the 25 cycles, the reaction was incubated at 72° C. for 3 minutes and then cooled at 10° C. until further processed.

Five microliters of the PCR reaction mixture was subjected to 1% TBE-agarose gel electrophoresis with ethidium bromide in TBE buffer to identify the desired 765 bp PCR fragment. The PCR fragment from the remaining 45 µl of the PCR reaction mixture was purified using a QIAquick PCR Purification Kit (Qiagen Inc., Valencia, Calif., USA). The purified fragment was digested with EcoRI and BamHI (New England Biolabs, Ipswich, Mass., USA) and analyzed on a 1% TBE-agarose gel with ethidium bromide.

The plasmid pTrc99A (supra) was digested with EcoRI and BamHI, and the resulting fragments separated by 1% TBE-agarose gel electrophoresis followed by visualization with a DARK READER™ (Clare Chemical Research, Dolores, Colo., USA). The desired 4.1 kb fragment was excised from the gel with a disposable razor blade and purified using a QIAquick Gel Extraction Kit (Qiagen, Inc.).

Cloning of the DNA fragment containing E. coli ydfG into pTrc99A was performed using T4 DNA ligase (New England Biolabs). The reaction mixture contained 1× T4 DNA ligase buffer, 1 µl T4 DNA ligase, 1 µl of the pTrc99A EcoRI/BamHI digested DNA fragment above, and 5 µl of the ydfG EcoRI/BamHI digested PCR product above in total volume of 10 µl. The reaction mixture was incubated at 16° C. overnight and subsequently used to transform SURE competent cells (Agilent Technologies, Inc.) according to manufacturer's instructions. After a recovery period, two 100 µl aliquots from the transformation mixture were plated onto 150 mm 2XYT plates supplemented with 100 µg of ampicillin per ml and incubated overnight at 37° C.

Recombinant colonies of the transformations were each inoculated into 3 ml of LB medium supplemented with ampicillin (100 µg/ml). Plasmid DNA was prepared from these cultures using a BIOROBOT® 9600 workstation (Qiagen, Inc.) and analyzed by 1% TBE-agarose gel electrophoresis following EcoRI/BamHI digestion. The plasmid DNA from one clone designated pMeJi9 and having the correct restriction digest pattern was further subjected to sequence analysis to confirm integration of the correct ydfG coding sequence.

Example 2

Construction of E. coli ydfG 3-HPDH Gene Variants

Synthetic DNA sequences encoding the desired ydfG variants and containing a 5' flanking EcoRI restriction site and 3' NaeI restriction site were provided in plasmid constructs from DNA2.0 (Menlo Park, Calif., USA). Each plasmid was digested with EcoRI and NaeI restriction enzymes, and the resulting fragments separated on a 1% TAE agarose gel followed by visualization with the aid of a DARK READER™ (Clare Chemical Research). The desired DNA band containing the ydfG variant encoding sequence was excised from the gel with a disposable razor blade and purified using NucleoSpin Extract II Kit (Machery-Nagel, Duren, Germany).

Plasmid pMeJi9 (supra) was linearized by digestion with EcoRI and NaeI, followed by incubation with Alkaline Phosphatase, Calf Intestinal (CIP) (New England Biolabs) for removal of the 5' phosphate. The resulting mixture was subjected to gel electrophoresis, visualized, and purified as described above to provide the desired 4657 bp DNA fragment.

Cloning of each ydfG variant encoding sequence into linearized pMeJi9 was performed by incubating 1× T4 DNA ligase buffer, 1 µl T4 DNA ligase (New England Biolabs), 2 µl EcoRI/NaeI linearized pMeJi9, and 15 µl of the selected EcoRI/NaeI ydfG variant encoding sequence (in total volume of 20 µl) for 2 hours at room temperature. A 10 µl sample of the incubation reaction was used to transform SoloPack® Gold chemically competent cells according to according to the manufacturer's instructions. After a recovery period, two 100 µl aliquots from the transformation mixture were plated onto 150 mm 2XYT plates supplemented with 100 µg of ampicillin per ml and incubated overnight at 37° C. Putative recombinant clones were selected from the selection plates and plasmid DNA was prepared from each one using a BIOROBOT® 9600 workstation. Clones were analyzed by sequencing. Those plasmids with the correct sequence are shown in Table 1.

TABLE 1

| Variant Name | SEQ ID | Cloning Plasmid Name | Amino Acid Changes |
| --- | --- | --- | --- |
| Mut1 | 7 | pMcTs68 | T9G/A10*/G31D/R32L/R33N/Q34P/E35A/R36A |
| Mut2 | 8 | pMcTs69 | T9G/G31E/R32L/R33N/Q34P/E35A/R36A |
| Mut3 | 9 | pMcTs70 | T9G/A10*/G31E/R32L/R33N/Q34P/E35A/R36A |
| Mut4 | 10 | pMcTs71 | T9G/G31D/R32L/R33S/Q34A/E35D/R36A |
| Mut5 | 11 | pMcTs72 | T9G/A10*/G31D/R32L/R33S/Q34A/E35D/R36A |
| Mut6 | 12 | pMcTs73 | T9G/G31D/R32L/R33N/Q34P/E35A/R36A |
| Mut7 | 13 | pMcTs74 | T9G/A10*/G31E/R32L/R33S/Q34A/E35D/R36A |
| Mut8 | 14 | pMcTs75 | T9G/G31E/R32L/R33S/Q34A/E35D/R36A |

*represents deletion of the amino acid.

Additional variants shown in Table 2 below were constructed using site-directed mutagenesis and the indicated primers in a PCR reaction using QuikChange II XL Site-Directed Mutagenesis Kit (Agilent Technologies, Inc.). The PCR reaction contained 1× Reaction Buffer, 125 ng of each primer, 30 ng plasmid DNA template, 1× dNTPs, 1× Quick solution, 2.5 U PfuUltra HF DNA polymerase in a final volume of 50 µl. The amplification reaction was performed in an EPPENDORF® MASTERCYCLER® 5333 (Eppendorf Scientific, Inc.) programmed for one cycle at 95° C. for 3 minutes; and 18 cycles each at 95° C. for 50 seconds, 60° C. for 50 seconds, and 68° C. for 6 minutes. After the 18 cycles, the reaction was incubated at 68° C. for 7 minutes and then cooled at 10° C. until further processed. To the each PCR reaction 1 µl of DpnI was added and incubated at 37° C. for 1.5 hours to digest template plasmid DNA.

From each site directed PCR reaction, 2.5 µl of the reaction was transformed into XL10 Gold Super competent cells (Agilent Technologies, Inc.) according to manufacturer's instructions. After a recovery period, two 100 µl aliquots from the transformation mixture were plated onto 150 mm 2XYT plates supplemented with 100 µg of ampicillin per ml and incubated overnight at 37° C.

Recombinant colonies of the transformations were each inoculated into 3 ml of LB medium supplemented with ampicillin (100 µg/ml). Plasmid DNA was prepared from these cultures using a BIOROBOT® 9600 workstation (Qiagen, Inc.) and subjected to sequence analysis to confirm the site directed mutation in the ydfG coding sequence.

TABLE 2

| Variant Name | SEQ ID | Cloning Plasmid Name | Amino Acid Changes | Forward Primer | Reverse Primer | Template |
|---|---|---|---|---|---|---|
| Mut9 | 17 | pMcTs79 | G31D/R32L/R33N/Q34P/E35A/R36A | 614470 | 614471 | pMcTs73 |
| Mut10 | 18 | pMcTs80 | T9G/R32L/R33N/Q34P/E35A/R36A | 614468 | 614469 | pMcTs73 |
| Mut11 | 19 | pMcTs81 | T9G/G31D/R33N/Q34P/E35A/R36A | 614472 | 614473 | pMcTs73 |
| Mut12 | 20 | pMcTs82 | T9G/G31D/R32L/Q34P/E35A/R36A | 614476 | 614477 | pMcTs73 |
| Mut13 | 21 | pMcTs83 | T9G/G31D/R32L/R33N/E35A/R36A | 614479 | 614480 | pMcTs73 |
| Mut14 | 22 | pMcTs84 | T9G/G31D/R32L/R33N/Q34P/R36A | 614464 | 614465 | pMcTs73 |
| Mut15 | 23 | pMcTs85 | T9G/G31D/R32L/R33N/Q34P/E35A | 614466 | 614467 | pMcTs73 |
| Mut16 | 24 | pMcTs89 | T9G/G31D/R32L/R36A | 614550 | 614551 | pMcTs73 |
| Mut17 | 25 | pMcTs86 | T9G/G31D/R32L/E35A/R36A | 614548 | 614549 | pMcTs73 |
| Mut18 | 26 | pMcTs87 | T9G/G31D/R32L/Q34P/R36A | 614546 | 614547 | pMcTs73 |
| Mut19 | 27 | pMcTs88 | T9G/G31D/R32L/R33N/R36A | 614552 | 614553 | pMcTs73 |
| Mut20 | 28 | pMcTs98 | G31D | 614975 | 614976 | pMeJi9 |
| Mut21 | 29 | pMcTs99 | T9G/G31D/R36A | 614977 | 614978 | pMcTs89 |
| Mut22 | 30 | pMcTs100 | T9G/G31D/R32L | 614979 | 614980 | pMcTs89 |
| Mut23 | 31 | pMcTs104 | T9G | 614973 | 614974 | pMeJi9 |
| Mut24 | 32 | pMcTs105 | T9G/G31D | 614973 | 614974 | pMcTs98 |
| Mut25 | 33 | pMcTs114 | G31D/R32L | 614470 | 614471 | pMcTs100 |

Example 3

Expression of E. coli ydfG 3-HPDH Gene Variants in MG1655 Cells

Electrocompetent MG1655 cells were transformed with the resulting cloning plasmids from Example 2 (or controls pMeJi9 or pTrc99A) according to the procedure described in Sheen, J. (1989). "High-Efficiency Transformation by Electroporation." Current Protocols in Molecular Biology. 1.8.4. After a recovery period, two 100 µl aliquots from the transformation reaction were plated onto 150 mm 2XYT plates supplemented with 100 µg of ampicillin per ml and incubated overnight at 37° C. For each transformation, plasmid DNA of a selected recombinant clone was prepared using a BIOROBOT® 9600 workstation and analyzed by sequencing. The selected clone was then inoculated into a culture of 3 ml of LB media supplemented with 100 µg of ampicillin and incubated overnight at 37° C. with shaking. 250 µl of the overnight culture was added to 25 ml of LB media supplemented with 100 µg of ampicillin per ml in a 125 ml baffled shake flask and grown to $OD_{600}$~0.6 before adding 0.5 mM IPTG to induce expression from the plasmid. After 1 hour incubation with IPTG the culture was collected by centrifugation and submitted for enzyme assays, as described below. Samples from the cultures were also collected for SDS-PAGE analysis on an 8-16% Bio-Rad Criterion stain-free Tris-HCl gel (Bio-Rad Laboratories, Inc., Hercules, Calif., USA).

Example 4

Cofactor Specificity of Cells Expressing E. coli ydfG 3-HPDH Gene Variants

Cultures from Example 3 were harvested by centrifugation (15,000×g at 4° C. for 10 min) and stored at −80° C. Cells were thawed on ice and the pellet was resuspended in Phosphate Buffered Saline (PBS; NaCl, 137 mM; KCl, 2.7 mM; $Na_2HPO_4$, 10 mM; $KH_2PO_4$, 1.76 mM) at pH 7.4 containing one tablet of Roche Complete Mini proteases inhibitor cocktail (Roche, Basel) per 10 mL of buffer. Cells were washed three times, and then resuspended in PBS plus protease inhibitor supplemented with lysozyme (Sigma-Aldrich, Saint-Louis, Mo.) at a concentration of 2 mg/mL. Cells were then incubated on ice for 30 minutes to allow release of cytoplasmic content, and membrane debris was collected by centrifugation (15,000×g at 4° C. for 30 min). The supernatant containing the crude extract (CCE) was transferred to a new tube and kept on ice until further use. CCE protein was quantitated using a Pierce BCA protein detection kit (Thermo Fisher scientific, Rockford, Ill., USA) using BSA as a standard by following the manufacturer recommendations. The indicated variants were assayed from the CCE using one or both of the protocols described below.

A reverse serine dehydrogenase activity assay was conducted with either NADP+ or NAD+ cofactor by measuring the appearance over time of the associated reduced cofactor at 340 nm. The assay was performed in a 96 well micro-plate, and the final volume was 300 µL. The reaction was started by adding 30 µL of CCE (supra) into 270 µL of assay buffer (100 mM Tris pH 8.0, 10 mM $NaHCO_3$, 5 mM $MgCl_2$, 400 mM L-serine and 2 mM of either NAD+ or NADP+). Absorbance at 340 nm was followed on a micro-plate reader (Spectra Max 340PC, Molecular Devices LLC, Sunnyvale, Calif., USA) for 10 minutes at room temperature (~25° C.). One unit was defined as the amount of enzyme necessary to produce 1 µmol of either NADH or NADPH in one minute in the presence of L-serine at pH 8.0, 25° C.

The results using the serine dehydrogenase assay (see Table 3) show increased specificity of NAD(H) over to NADP (H) for certain dehydrogenase variants compared to the parent E. coli ydfG gene product (expressed from pMeJi9) and a control lacking a ydfG gene product (blank expression vector pTrc99A).

TABLE 3

| Name | SEQ ID | Cloning Plasmid Name | Serine DeH SA (uts/mg prot) NADP+ | Serine DeH SA (uts/mg prot) NAD+ | NAD+/NADP+ |
|---|---|---|---|---|---|
| Control (ydfG) | 1 | pMeJi9 | 12.74 | 0.35 | 0.03 |
| Control | — | pTrc99A | 0.35 | 1.01 | 2.88 |
| Mut1 | 7 | pMcTs68 | 0.75 | 0.58 | 0.78 |
| Mut2 | 8 | pMcTs69 | 0.98 | 2.69 | 2.76 |
| Mut3 | 9 | pMcTs70 | 0.28 | 0.34 | 1.21 |
| Mut4 | 10 | pMcTs71 | 0.88 | 9.41 | 10.70 |
| Mut5 | 11 | pMcTs72 | 0.74 | 0.49 | 0.66 |
| Mut6 | 12 | pMcTs73 | 0.80 | 17.48 | 21.85 |
| Mut7 | 13 | pMcTs74 | 0.47 | 0.92 | 1.97 |
| Mut8 | 14 | pMcTs75 | 0.97 | 1.18 | 1.22 |

A forward malonate semi-aldehyde reductase assay was conducted by measuring the disappearance of either NADH or NADPH over time at 340 nm. Malonate semi-aldehyde was synthesized in-house according to the protocol developed by Yamada and Jacoby (1960) "Direct conversion of malonic semialdehyde to acetyl-coenzyme A", J. Biol. Chem., 235(3): 589-594. The assay was performed in a 96 well micro-plate, and the final volume was 200 µL. The reaction was started by adding 30 µL of CCE (supra) into 170 µL of assay buffer (2 mM malonate semialdehyde, 100 mM Tris pH 8.0 and 0.5 mM either NADH or NADPH). Absorbance at 340 nm was followed on a micro-plate reader (Spectra Max 340PC, Molecular Devices LLC) for 10 minutes at room temperature (~25° C.). One unit was defined as the amount of enzyme necessary to oxidize 1 µmol of either NADH or NADPH in one minute in the presence of malonate semialdehyde at pH 8.0, 25° C.

The results using the malonate semi-aldehyde reductase assay (see Table 4) show increased specificity of NAD(H) over to NADP(H) for certain 3-HPDH variants compared to the parent *E. coli* ydfG gene product (expressed from pMeJi9) and a control lacking a ydfG gene product (blank expression vector pTrc99A).

TABLE 4

| Name | SEQ ID | Cloning Plasmid Name | Serine DeH SA (uts/mg prot) NADPH | NADH | NADH/NADPH |
|---|---|---|---|---|---|
| Control | — | pTrc99A | 4.30 | 2.75 | 0.64 |
| Control (ydfG) | 1 | pMeJi9 | 5174.76 | 0.00 | 0.00 |
| Mut1 | 7 | pMcTs68 | 2.18 | 0.07 | 0.03 |
| Mut2 | 8 | pMcTs69 | 4.67 | 0.00 | 0.00 |
| Mut3 | 9 | pMcTs70 | 0.00 | 0.00 | 0.00 |
| Mut4 | 10 | pMcTs71 | 2.75 | 2.87 | 1.04 |
| Mut5 | 11 | pMcTs72 | 4.36 | 0.00 | 0.00 |
| Mut6 | 12 | pMcTs73 | 22.26 | 39.25 | 1.76 |
| Mut7 | 13 | pMcTs74 | 0.75 | 0.00 | 0.00 |
| Mut8 | 14 | pMcTs75 | 3.29 | 0.00 | 0.00 |
| Mut9 | 17 | pMcTs79 | 3.29 | 0.00 | 0.00 |
| Mut10 | 18 | pMcTs80 | 2.63 | 0.00 | 0.00 |
| Mut11 | 19 | pMcTs81 | 1.29 | 0.00 | 0.00 |
| Mut12 | 20 | pMcTs82 | 1.40 | 31.98 | 22.84 |
| Mut13 | 21 | pMcTs83 | 2.16 | 14.23 | 6.60 |
| Mut14 | 22 | pMcTs84 | 2.00 | 9.41 | 4.71 |
| Mut15 | 23 | pMcTs85 | 2.30 | 20.66 | 9.00 |
| Mut16 | 24 | pMcTs89 | 0.44 | 24.33 | 54.83 |
| Mut17 | 25 | pMcTs86 | 0.80 | 27.45 | 34.17 |
| Mut18 | 26 | pMcTs87 | 1.04 | 22.34 | 21.47 |
| Mut19 | 27 | pMcTs88 | 2.27 | 15.15 | 6.67 |
| Mut20 | 28 | pMcTs98 | 0.00 | 0.00 | 0.00 |
| Mut21 | 29 | pMcTs99 | 0.41 | 5.05 | 12.45 |
| Mut22 | 30 | pMcTs100 | 1.55 | 71.91 | 46.31 |
| Mut23 | 31 | pMcTs104 | 288.03 | 0.00 | 0.00 |
| Mut24 | 32 | pMcTs105 | 0.00 | 10.56 | — |
| Mut25 | 33 | pMcTs114 | 2.56 | 0.00 | 0.00 |

Example 5

Construction of an Expression Vector for the *I. Orientalis* YMR226c 3-HPDH Gene The plasmid pMBin190 (WO2012/074818) contains the *I. orientalis* YMR226c nucleotide sequence encoding the 3-HPDH of SEQ ID NO: 4 flanked by NheI/PacI sites. The pMBin190 plasmid was digested with NheI and PacI, gel isolated and purified using Qiagen Gel Extraction kit (Qiagen, Inc.) and the 827 bp fragment was ligated into a 7942 bp fragment of pMIBa107 (WO2012/074818) digested with XbaI and PacI that was gel isolated and purified using the Qiagen Gel Extraction kit. Cloning of the DNA fragment containing *I. orientalis* YMR226c polynucleotide into pMIBa107 was performed using T4 DNA ligase (New England Biolabs). The reaction mixture contained 1× T4 DNA ligase buffer, 1 µl T4 DNA ligase, 1 µl of the pMIBa107 XbaI/PacI digested DNA fragment above, and 5 µl of the YMR226c NheI/PacI digested product above in total volume of 10 µl. The reaction mixture was incubated at room temperature for at least 1 hour and subsequently used to transform One Shot TOP10 cells (Invitrogen) according to manufacturer's instructions. After a recovery period, two 100 µl aliquots from the transformation mixture were plated onto 150 mm 2XYT plates supplemented with 100 µg of ampicillin per ml and incubated overnight at 37° C. Recombinant colonies of the transformations were each inoculated into 3 ml of LB medium supplemented with ampicillin (100 µg/ml). Plasmid DNA was prepared from these cultures using a BIOROBOT® 9600 workstation (Qiagen, Inc.) and subjected restriction digest checks. The plasmid DNA from one clone having the correct restriction digest pattern was further subjected to sequence analysis and designated pMBin200.

The *I. orientalis* YMR226c coding sequence was amplified by PCR using two synthetic oligonucleotide primers designed to generate an EcoRI restriction site at the 5' end and a XmaI restriction site at the 3' end for integration into pTrc99A (supra).

Twenty nanograms of pMBin200 plasmid DNA was used as a template in a PCR reaction further containing 1× Phusion HF buffer, fifty picomoles each of primers 614967 and 614968, 0.2 mM each of dATP, dGTP, dCTP, and dTTP, and 2 units Phusion® Hot Start High-Fidelity DNA Polymerase (Finnzymes, Vantaa, Finland) in a final volume of 50 µl. The amplification reaction was performed in an EPPENDORF® MASTERCYCLER® 5333 (Eppendorf Scientific, Inc.) programmed for one cycle at 95° C. for 3 minutes; and 30 cycles each at 95° C. for 30 seconds, 56.5° C. for 30 seconds, and 72° C. for 1 minute. After the 30 cycles, the reaction was incubated at 72° C. for 5 minutes and then cooled at 10° C. until further processed.

The 831 bp PCR fragment from the PCR reaction mixture was subjected to 1% TBE-agarose gel electrophoresis with ethidium bromide in TBE buffer and the PCR product was cut out of the gel and purified using the NucleoSpin Extract II kit (Macherey-Nagel). The purified fragment was digested with EcoRI and XmaI (New England Biolabs) and the plasmid pTrc99A was digested with EcoRI and XmaI, and the resulting fragments separated by 1% TBE-agarose gel electrophoresis followed by visualization with a DARK READER™ (Clare Chemical Research). The desired 4.16 kb fragment of pTrc99A and 819 bp YMR226c fragment was excised from the gel with a disposable razor blade and purified using a NucleoSpin Extract II kit (Macherey-Nagel).

Cloning of the DNA fragment containing *I. orientalis* YMR226c coding sequence into pTrc99A was performed using T4 DNA ligase (New England Biolabs). The reaction mixture contained 1× T4 DNA ligase buffer, 1 µl T4 DNA ligase, 1 µl of the pTrc99A EcoRI/XmaI digested DNA fragment above, and 15 µl of the YMR226c EcoRI/XmaI digested PCR product above in total volume of 20 µl. The reaction mixture was incubated at room temperature for 1 hour and subsequently used to transform Solo Pack Gold supercompetent cells (Agilent Technologies, Inc.) according to manufacturer's instructions. After a recovery period, two 100 µl aliquots from the transformation mixture were plated onto 150 mm 2XYT plates supplemented with 100 µg of ampicillin per ml and incubated overnight at 37° C. Recombinant colonies of the transformations were each inoculated into 3 ml of LB medium supplemented with ampicillin (100 µg/ml).

Plasmid DNA was prepared from these cultures using a BIOROBOT® 9600 workstation (Qiagen, Inc.) and analyzed by 1% TBE-agarose gel electrophoresis following EcoRI/XmaI digestion. The plasmid DNA from one clone designated pMcTs103 and having the correct restriction digest pattern was further subjected to sequence analysis to confirm integration of the correct YMR226c coding sequence. From sequencing it was determined that this YMR226c coding sequence differed from the expected genomic sequence by 1 base pair.

To correct the 1 base pair mutation in pMcTs103 site directed mutagenesis was performed using pMcTs103 as the template DNA in a PCR reaction using QuikChange II XL Site-Directed Mutagenesis Kit (Agilent Technologies, Inc.) as described supra using primers 615428 and 614429.

Recombinant colonies of the transformations were each inoculated into 3 ml of LB medium supplemented with ampicillin (100 μg/ml). Plasmid DNA was prepared from these cultures using a BIOROBOT® 9600 workstation (Qiagen, Inc.) and subjected to sequence analysis to confirm the site directed mutation in the YMR226c coding sequence. A clone with the correct sequence based on sequencing was named pMcTs107.

Example 6

Construction of *I. Orientalis* YMR226c 3-HPDH Gene Variants

Based on the findings of shown in Example 4, additional 3-HPDH gene variants were constructed using the parent *I. orientalis* YMR226c homolog (SEQ ID NO: 4).

Site-directed mutagenesis was performed using pMcTs107 (supra) as the template DNA in a PCR reaction using a QuikChange II XL Site-Directed Mutagenesis Kit (Agilent Technologies, Inc.) as described supra using primers 615006 and 615007, designed to make amino acid substitutions of aspartic acid and leucine at positions 45 and 46 of SEQ ID NO: 4, respectively (corresponding to positions 31 and 32 of SEQ ID NO: 2) resulting in the variant mut26 (SEQ ID NO: 80).

Recombinant colonies of the transformations were subjected to sequence analysis to confirm the site directed substitutions in the YMR226c coding sequence. A clone with the correct sequence encoding the variant mut26 (SEQ ID NO: 80) was named pMcTs110.

Site-directed mutagenesis was performed on pMcTs110 in a PCR reaction using a QuikChange II XL Site-Directed Mutagenesis Kit (Agilent Technologies, Inc.) as described supra using primers 615004 and 615005, designed to introduce an amino acid substitution of glycine at position 20 of SEQ ID NO: 80 (corresponding to position 9 of SEQ ID NO: 2) resulting in the variant mut27 (SEQ ID NO: 81).

Rcombinant colonies of the transformations were subjected to sequence analysis to confirm the site directed substitutions in the YMR226c coding sequence and a clone with the correct sequence encoding the variant mut27 (SEQ ID NO: 81) was named pMcTs112.

Example 7

Cofactor Specificity of Cells Expressing *I. Orientalis* YMR226c 3-HPDH Gene Variants The *I. orientalis* gene variants from Example 6 were expressed in MG1655 cells and the 3-HPDH cofactor specificity was measured using the malonate semi-aldehyde reductase assay described supra. Results are shown below in Table 5. The mut27 *I. orientalis* YMR226c 3-HPDH variant expressed from pMcTs112 (SEQ ID NO: 81) showed increased specificity for NAD(H) over to NADP(H) compared to the parent *I. orientalis* YMR226c gene product expressed from pMcTs107 (SEQ ID NO: 4) and a control lacking a YMR226c gene product (blank expression vector pTrc99A).

TABLE 5

| Name | SEQ ID | Cloning Plasmid Name | Serine DeH SA (uts/mg prot) pH 6 | | Serine DeH SA (uts/mg prot) pH 8 | |
|---|---|---|---|---|---|---|
| | | | NADPH | NADH | NADPH | NADH |
| Control | — | pTrc99A | 53.32 | 8.46 | 7.79 | 6.96 |
| *E. coli* ydfG (wt) | 1 | pMeJi9 | 12137.66 | 10.25 | 737.62 | 8.73 |
| mut22 | 30 | pMcTs100 | 36.08 | 121.98 | 7.37 | 38.01 |
| *I. orientalis* YMR226c (wt) | 4 | pMcTs107 | 399.52 | 8.20 | 131.39 | 5.21 |
| mut27 | 81 | pMcTs112 | 58.02 | 399.06 | 5.38 | 18.76 |

Example 8

Construction of an Expression Vector for Integration of the *I. Orientalis* YMR226c 3-HPDH Gene at the *L. orientalis* adh9091 Locus The *I. orientalis* YMR226 3-HPDH coding sequence was amplified from pMcTs107 (supra) with primers designed to add flanking 5' NheI and 3' PacI restriction sites. Fifty nanograms of pMcTs107 plasmid DNA was used as a template in a PCR reaction further containing 1× Phusion HF buffer, fifty picomoles each of primers 615485 and 615486, 0.2 mM each of dATP, dGTP, dCTP, and dTTP, and 2 units Phusion® Hot Start High-Fidelity DNA Polymerase (Finnzymes) in a final volume of 50 μl. The amplification reaction was performed in an EPPENDORF® MASTERCYCLER® 5333 (Eppendorf Scientific, Inc.) programmed for one cycle at 95° C. for 3 minutes; and 30 cycles each at 95° C. for 30 seconds, 55° C. for 30 seconds, and 72° C. for 1 minute. After the 30 cycles, the reaction was incubated at 72° C. for 5 minutes and then cooled at 10° C. until further processed.

The 837 bp PCR fragment from PCR reaction mixture was subjected to 1% TBE-agarose gel electrophoresis with ethidium bromide in TBE buffer and the PCR product was excised from the gel and purified using the NucleoSpin Extract II kit (Macherey-Nagel). The purified fragment was digested with NheI and PacI (New England Biolabs) and the plasmid pMBin204 (WO2012/074818) was digested with XbaI and PacI, and the resulting fragments separated by 1% TBE-agarose gel electrophoresis followed by visualization with a DARK READER™ (Clare Chemical Research). The desired 8.4 kb fragment of pMBin204 and 827 bp YMR226c fragment was excised from the gel and purified using a NucleoSpin Extract II kit (Macherey-Nagel).

Cloning of the DNA fragment containing the coding sequence of the *I. orientalis* YMR226c 3-HPDH (SEQ ID NO: 4) into pMBin204 was performed using T4 DNA ligase (New England Biolabs). The reaction mixture contained 1× T4 DNA ligase buffer, 1 µl T4 DNA ligase, 1 µl of the pMBin204 XbaI and PacI digested DNA fragment above, and 5 µl of the YMR226c NheI and PacI digested PCR product above in total volume of 20 µl. The reaction mixture was incubated at room temperature for 1 hour and subsequently used to transform One Shot TOP10 cells (Invitrogen) according to manufacturer's instructions. After a recovery period, two 100 µl aliquots from the transformation mixture were plated onto 150 mm 2XYT plates supplemented with 100 µg of ampicillin per ml and incubated overnight at 37° C. Recombinant colonies of the transformations were each inoculated into 3 ml of LB medium supplemented with ampicillin (100 µg/ml).

Figure 5:
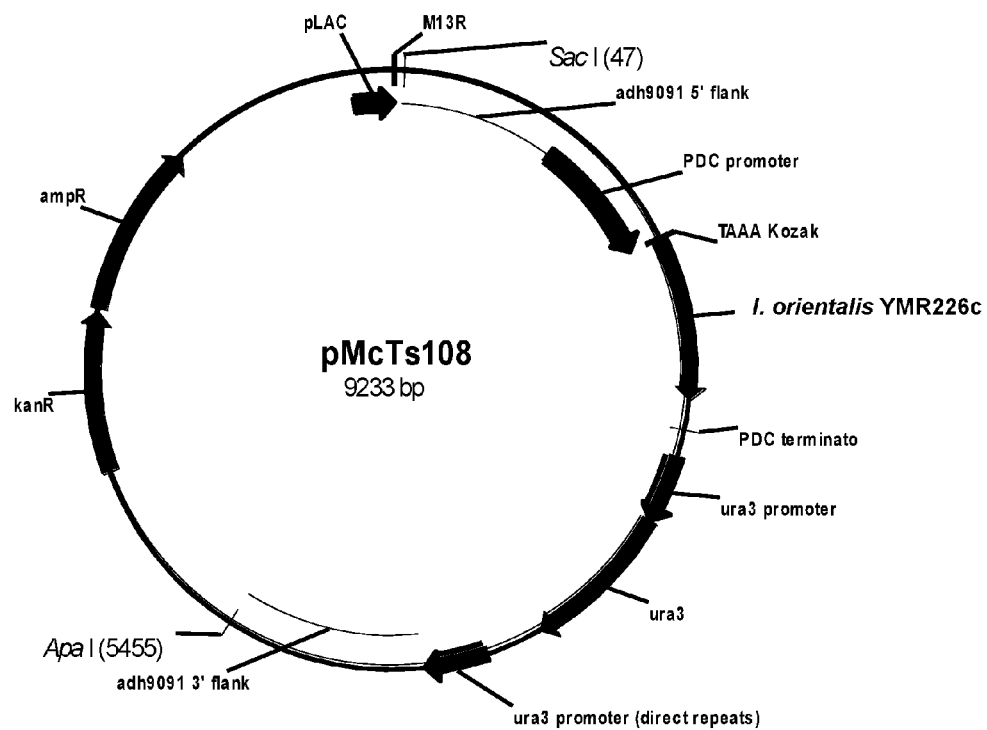
FIG. 5 shows plasmid map for pMcTs108.

Plasmid DNA was prepared from these cultures using a BIOROBOT® 9600 workstation (Qiagen, Inc.) and analyzed by restriction digestion. The plasmid DNA from one clone having the correct restriction digest pattern was further subjected to sequence analysis to confirm the correct YMR226c coding sequence was designated pMcTs108 (FIG. 5).

Example 9

Construction of an Expression Vector for Integration of the *I. Orientalis* YMR226c 3-HPDH Gene Variants at the *L. orientalis* adh9091 Locus The coding sequence for the *I. orientalis* YMR226 variant mut27 (SEQ ID NO: 81) was amplified from pMcTs112 (supra) with primers designed to add flanking 5' NheI and 3' PacI restriction sites. Fifty nanograms of pMcTs112 plasmid DNA was used as a template in a PCR reaction further containing 1× Phusion HF buffer, fifty picomoles each of primers 615485 and 615486, 0.2 mM each of dATP, dGTP, dCTP, and dTTP, and 2 units Phusion® Hot Start High-Fidelity DNA Polymerase (Finnzymes) in a final volume of 50 µl. The amplification reaction was performed in an EPPENDORF® MASTERCYCLER® 5333 (Eppendorf Scientific, Inc.) programmed for one cycle at 95° C. for 3 minutes; and 30 cycles each at 95° C. for 30 seconds, 55° C. for 30 seconds, and 72° C. for 1 minute. After the 30 cycles, the reaction was incubated at 72° C. for 5 minutes and then cooled at 10° C. until further processed.

The 837 bp PCR fragment from PCR reaction mixture was subjected to 1% TBE-agarose gel electrophoresis with ethidium bromide in TBE buffer and the PCR product was cut out of the gel and purified using the NucleoSpin Extract II kit (Macherey-Nagel). The purified fragment was digested with NheI and PacI (New England Biolabs) and the plasmid pMBin204 was digested with XbaI and PacI, and the resulting fragments separated by 1% TBE-agarose gel electrophoresis followed by visualization with a DARK READER™ (Clare Chemical Research). The desired 8.4 kb fragment of pMBin204 and 827 bp YMR226c variant fragment was excised from the gel and purified using a NucleoSpin Extract II kit (Macherey-Nagel).

Cloning of the DNA fragment containing the coding sequence for the *I. orientalis* YMR226c 3-HPDH variant mut27 into pMBin204 was performed using T4 DNA ligase (New England Biolabs). The reaction mixture contained 1× T4 DNA ligase buffer, 1 µl T4 DNA ligase, 1 µl of the pMBin204 XbaI and PacI digested DNA fragment above, and 10 µl of the YMR226c variant NheI and PacI digested PCR product above in total volume of 20 µl. The reaction mixture was incubated at room temperature for 1 hour and subsequently used to transform One Shot TOP10 cells (Invitrogen) according to manufacturer's instructions. After a recovery period, two 100 µl aliquots from the transformation mixture were plated onto 150 mm 2XYT plates supplemented with 100 µg of ampicillin per ml and incubated overnight at 37° C. Recombinant colonies of the transformations were each inoculated into 3 ml of LB medium supplemented with ampicillin (100 µg/ml).

Figure 6:
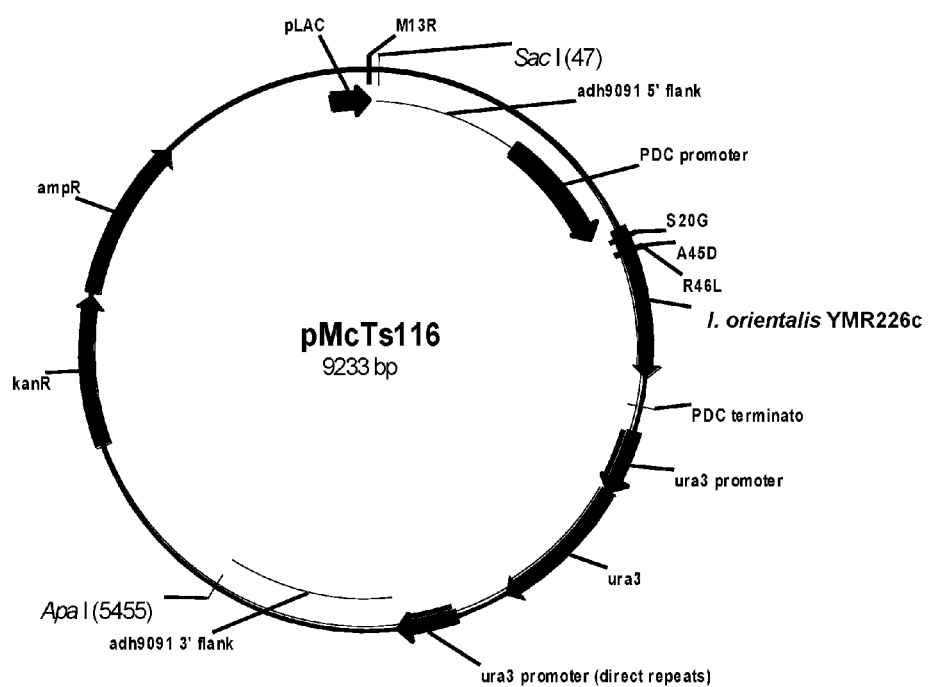
FIG. 6 shows plasmid map for pMcTs116.

Plasmid DNA was prepared from these cultures using a BIOROBOT® 9600 workstation (Qiagen, Inc.) and analyzed by restriction digestion. The plasmid DNA from one clone having the correct restriction digest pattern was further subjected to sequence analysis to confirm the correct YMR226c coding sequence and designated pMcTs116 (FIG. 6).

Example 10

Figure 7:
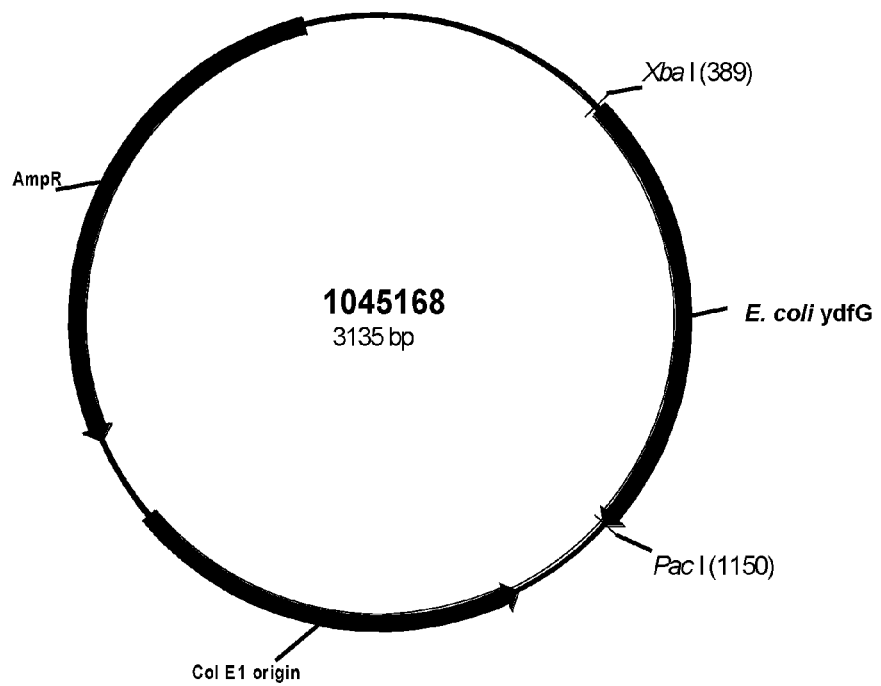
FIG. 7 shows plasmid map for p1045168.

Construction of an Expression Vector for Integration of the *E. coli* ydfG 3-HPDH Gene at the *I. Orientalis* adh9091 Locus The coding sequence for the *E. coli* ydfG 3-HPDH was codon-optimized for *I. orientalis* DNA, flanked by 5' XbaI site and 3' PacI restriction sites, and provided by GeneArt in a plasmid designated p1045168 (FIG. 7). Plasmids p1045168 and pMBin204 (WO2012/074818) were individually digested with XbaI and PacI and the resulting fragments separated by 1% TBE-agarose gel electrophoresis and visualized with a DARK READER™ (Clare Chemical Research). The desired 8.4 kb fragment of pMBin204 and 761 bp *E. coli* ydfG fragment was excised from the gel and purified using a NucleoSpin Extract II kit (Macherey-Nagel).

Cloning of the DNA fragment containing the coding sequence of the *E. coli* ydfG 3-HPDH (SEQ ID NO: 2) into pMBin204 was performed using T4 DNA ligase (New England Biolabs). The reaction mixture contained 1× T4 DNA ligase buffer, 1 µl T4 DNA ligase, 1 µl of the pMBin204 XbaI and PacI digested DNA fragment above, and 10 µl of the *E. coli* ydfG product in total volume of 20 µl. The reaction mixture was incubated at room temperature for 1 hour and subsequently used to transform One Shot TOP10 cells (Invitrogen) according to manufacturer's instructions. After a recovery period, two 100 µl aliquots from the transformation mixture were plated onto 150 mm 2XYT plates supplemented with 100 µg of ampicillin per ml and incubated overnight at 37° C. Recombinant colonies of the transformations were each inoculated into 3 ml of LB medium supplemented with ampicillin (100 µg/ml).

Figure 8:
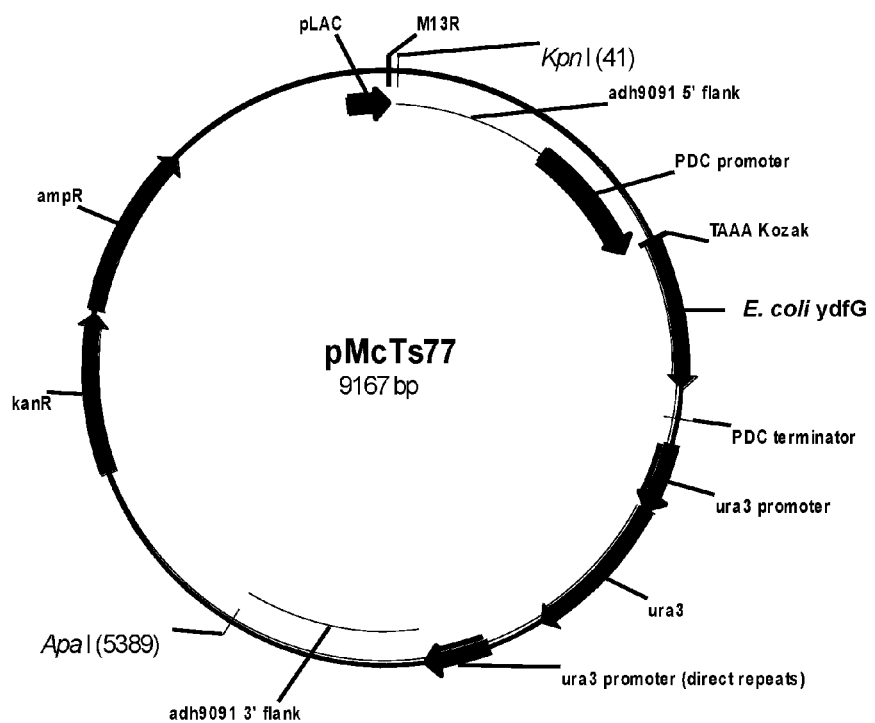
FIG. 8 shows plasmid map for pMcTs77.

Plasmid DNA was prepared from these cultures using a BIOROBOT® 9600 workstation (Qiagen, Inc.) and analyzed by restriction digestion. The plasmid DNA from one clone having the correct restriction digest pattern was designated pMcTs77 (FIG. 8).

Example 11

Figure 9:
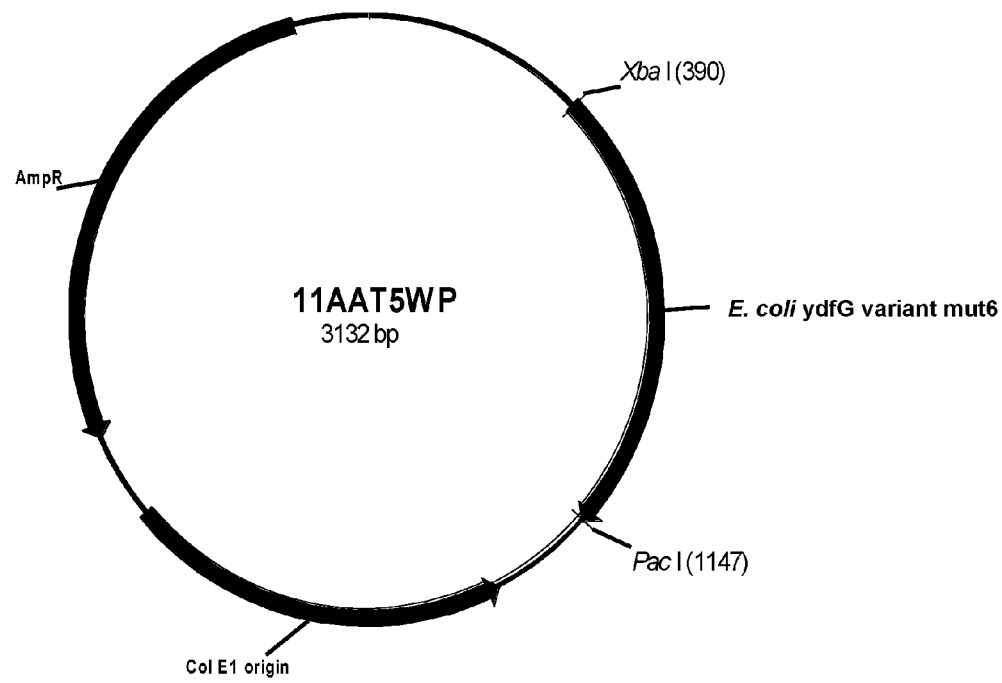
FIG. 9 shows plasmid map for p11AAT5WP.

Construction of an Expression Vectors for Integration of the *E. coli* ydfG 3-HPDH Gene Variants at the *I. Orientalis* adh9091 Locus The coding sequence for the *E. coli* ydfG 3-HPDH variant mut6 (SEQ ID NO: 12) was codon-optimized for *I. orientalis* DNA, flanked by 5' XbaI site and 3' PacI restriction sites, and provided by GeneArt in a plasmid designated p11AAT5WP (FIG. 9). Fifty nanograms of p11AAT5WP DNA was used as a template in a PCR reaction further containing 1× Expand buffer, fifty picomoles each of primers 614697 and 614698, 0.2 mM each of dATP, dGTP, dCTP, and dTTP, and 2.6 units Expand High Fidelity Polymerase (Roche) in a final volume of 50 µl. The amplification reaction was performed in an EPPENDORF® MASTERCYCLER® 5333 (Eppendorf Scientific, Inc.) programmed for one cycle at 95° C. for 2 minutes; and 30 cycles each at 95° C. for 30 seconds, 55° C. for 30 seconds, and 72° C. for 1 minute. After the 30 cycles, the reaction was incubated at 72° C. for 5 minutes and then cooled at 10° C. until further processed.

Figure 10:
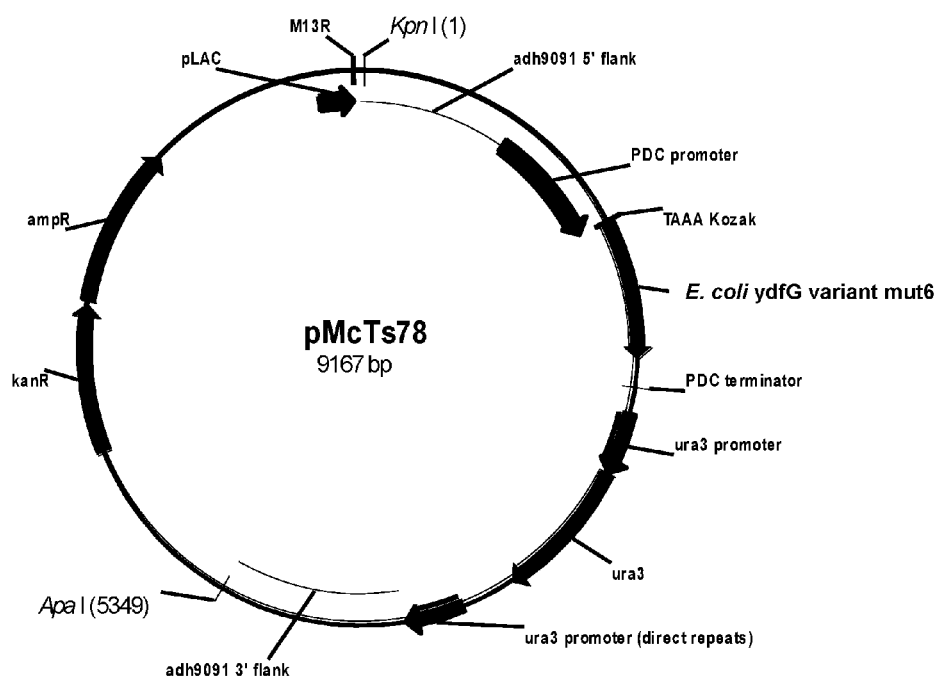
FIG. 10 shows plasmid map for pMcTs78.

The 783 bp PCR fragment was digested with XbaI and PacI and cloned into the 8.4 kb fragment of pMBin204 (supra) also digested with XbaI and PacI. Recombinant clones were screened by restriction digest and sequencing and a clone with the correct sequence was designated pMcTs78 (FIG. 10).

Plasmid p1045168 (supra; see also FIG. 7) was subjected to site directed mutagenesis using primers 615892 and 615893 as described supra to change the coding sequence for the wild-type *E. coli* ydfG 3-HPDH (SEQ ID NO: 2) into the coding sequence for the *E. coli* ydfG 3-HPDH variant mut25 (SEQ ID NO: 33) which contains the substitutions G31D and R32L. Recombinant colonies of the transformations were sequenced and a clone encoding the 3-HPDH with the correct amino acid changes was named pMcTs111.

Plasmid pMcTs111 was subjected to site directed mutagenesis using primers 615890 and 615891 as described supra to change the coding sequence for the *E. coli* ydfG 3-HPDH variant mut25 (SEQ ID NO: 33) into the coding sequence for the *E. coli* ydfG 3-HPDH variant mut22 (SEQ ID NO: 30) which contains the an additional T9G substitution. Recombinant colonies of the transformations were sequenced and a clone encoding the 3-HPDH with the correct amino acid changes was named pMcTs111. Recombinant colonies of the transformations were sequenced and a clone encoding the 3-HPDH with the correct amino acid changes was named pMcTs113.

Figure 11:
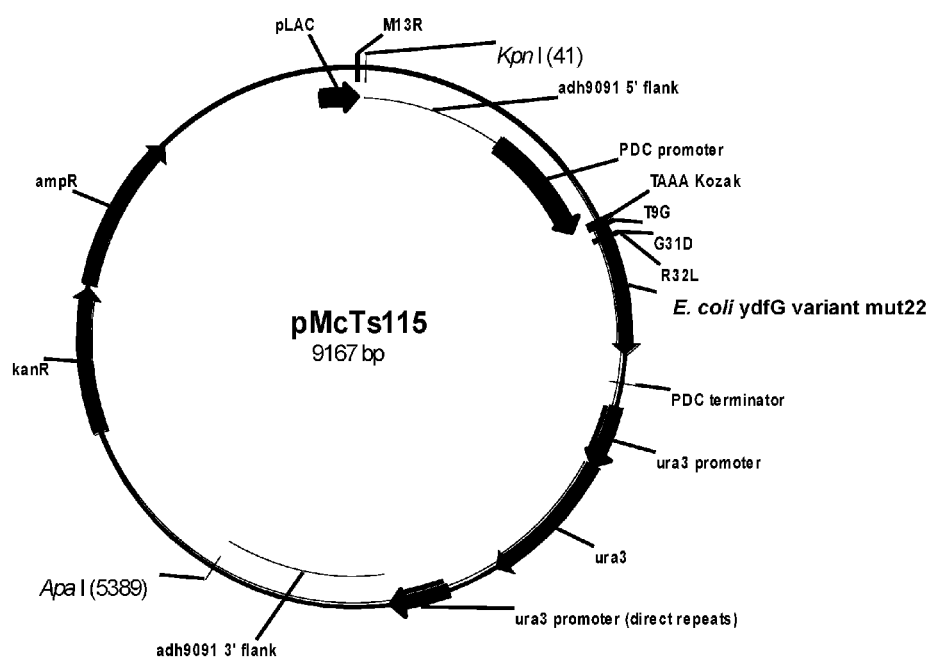
FIG. 11 shows plasmid map for pMcTs115.

The coding sequence for the *E. coli* ydfG 3-HPDH variant mut22 (SEQ ID NO: 30) was cloned into pMBin204 by digesting pMcTs113 with XbaI and PacI and ligating the resulting 761 bp fragment of pMcTs113 into the resulting 8.4 kbp fragment of pMBin204 also digested with XbaI and PacI as described supra. Recombinant clones were screened by restriction digest and sequencing, and a clone with the correct sequence was designated pMcTs115 (FIG. 11).

Example 12

Figure 12:
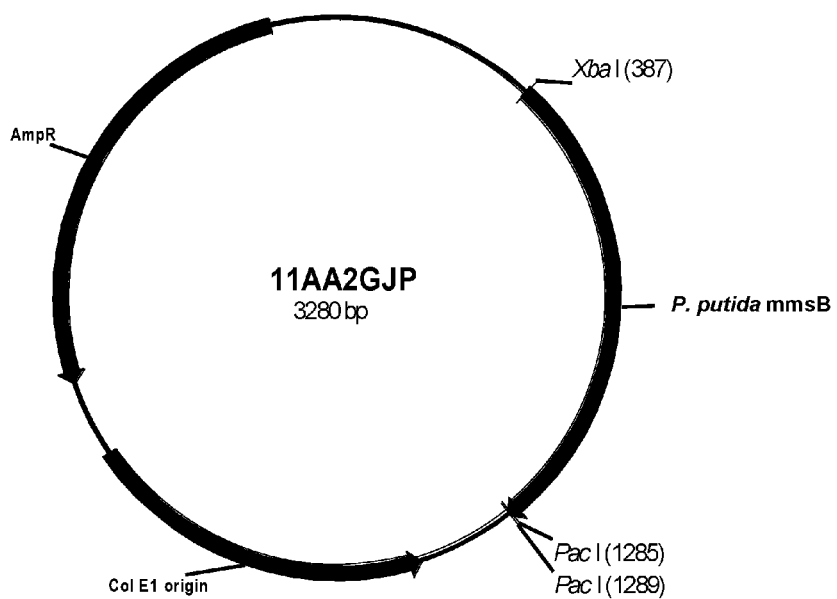
FIG. 12 shows plasmid map for p11AA2GJP.
Figure 13:
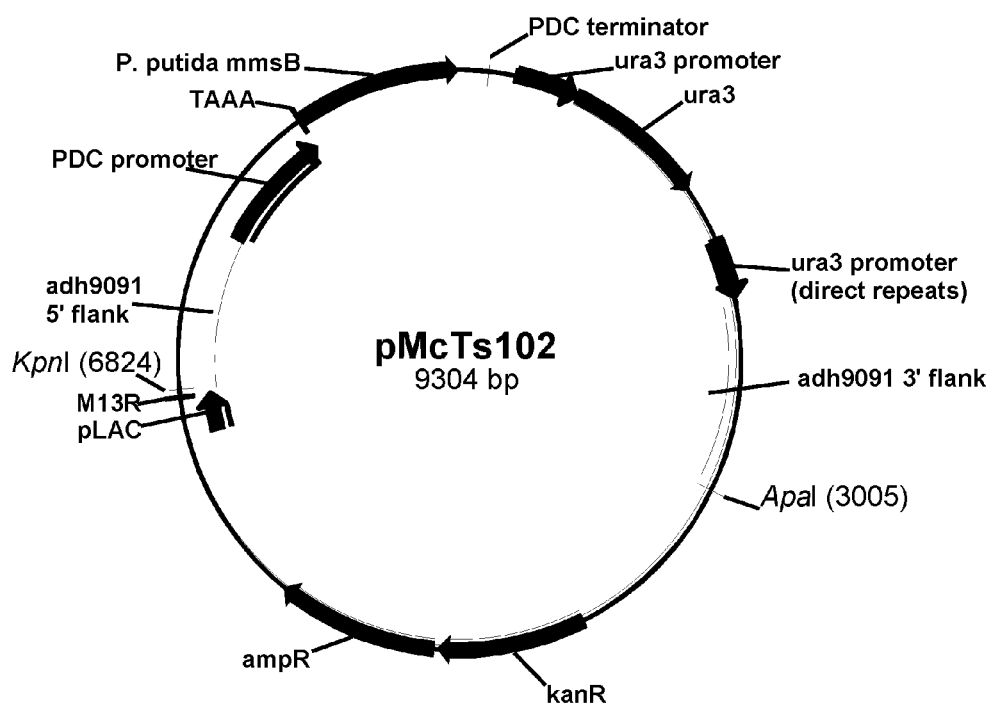
FIG. 13 shows plasmid map for pMcTs102.

Construction of an Expression Vectors for Integration of the *P. putida* mmsB 3-HPDH at the *I. Orientalis* adh9091 Locus The coding sequence for the *P. putida* mmsB 3-HPDH (SEQ ID NO: 82) was codon-optimized for *I. orientalis* DNA, flanked by 5' XbaI site and 3' PacI restriction sites, and provided by GeneArt in a plasmid designated p11AA2GJP (FIG. 12). Plasmid p11AA2GJP was digested with XbaI and PacI and the 898 bp fragment was cloned into the 8.4 kb fragment of pMBin204 also digested with XbaI and PacI as described supra. Several recombinant clones were screened by restriction digest and sequenced. One clone with the correct sequence was designated pMcTs102 (FIG. 13).

Example 13

Construction of Host Strains Containing an Active 3-HP Pathway and Expressing 3-HPDH at the *I. Orientalis* adh9091 Locus Approximately 10 µg each of each integration construct pMcTs77, pMcTs78, pMcTs102, pMcTs115 supra was individually digested with ApaI and KpnI and separated by gel electrophoresis on a 1% agarose gel using 89 mM Tris base-89 mM Boric Acid-2 mM disodium EDTA (TBE) buffer. Approximately 10 µg each of integration constructs pMcTs108 and pMcTs116 was digested with ApaI and SacI and separated by gel electrophoresis on a 1% agarose gel using TBE buffer. Fragments of approximately 5348 bp for pMcTs77, pMcTs78, and pMcTs115; 5485 bp for pMcTs102; and 5408 bp for pMcTs108 and pMcTs116 were excised and extracted using the QIAquick gel extraction kit (Qiagen, Inc.) according to the manufacturer's instructions. The linear constructs from plasmids pMcTs77, pMcTs78, pMcTs102, pMcTs115, pMcTs116, pMcTs108 were transformed into strain McTs259 (containing an active 3-HP pathway but having a deletion to the native *I. orientalis* YMR226c 3-HPDH gene; see WO2012/074818). Several single isolates from each transformation were screened for the site of integration as well as confirming that the other loci were still modified. The integration at adh9091 was confirmed by PCR using Phire® Plant Direct PCR kit (Finnzymes) according to the manufacturer's instructions with primers 614627+612909 and 612908+614626. The PCR product using primers 612908+614626 was approximately 1.97 kb for pMcTs77, pMcTs78, pMcTs102, pMcTs115, pMcTs116, and pMcTs108 integrants. The PCR product using primers 614627+612909 was approximately 3.4 kb for pMcTs102 integrants and approximately 3.3 kb for pMcTs77, pMcTs78, pMcTs102, pMcTs115, pMcTs116, pMcTs108 integrants. The integrity of the existing adh1202 locus and YMR226c locus was verified using primer sets 611245+612794 and 611815+612795 for adh1202 locus, and primer set 613034+613241 for YMR226c locus. A transformant with the correct size bands for the PCRs was designed as show below in Table 6.

TABLE 6

| Plasmid | 3-HPDH gene | Resulting host strain |
| --- | --- | --- |
| pMcTs77 | *E. coli* ydfG (wt) | McTs263 |
| pMcTs78 | *E. coli* mut6 | McTs265 |
| pMcTs102 | *P. putida* mmsB | McTs276 |
| pMcTs115 | *E. coli* mut22 | ShTh100 |
| pMcTs116 | *I. orientalis* mut27 | ShTh101 |
| pMcTs108 | *I. orientalis* YMR226c (wt) | MBin556 |

Example 14

3-HP Production from Host Strains Containing an Active 3-HP Pathway and Expressing 3-HPDH at the *I. Orientalis* adh9091 Locus Strains McTs263, McTs265, McTs276, ShTh100, ShTh101, and MBin556 supra were grown in shake flasks and samples were analyzed for cofactor specificity (as described supra) and 3-HP production as described in WO2012/074818. Control strains MeJi412 (containing an active 3-HP pathway including the native *I. orientalis* YMR226c 3-HPDH gene) and McTs244 (containing an active 3-HP pathway but having a deletion to the native *I. orientalis* YMR226c 3-HPDH gene) described in WO2012/074818, were also analyzed for 3-HPDH activity and 3-HP production. The results in table 7 show that deletion of the *I. orientalis* YMR226c gene results in no detectable 3-HP production and that 3-HP production can be restored using one copy of a gene encoding a 3-HPDH that has increased specificity for NAD(H).

TABLE 7

| Strain | 3-HPDH gene | 3HP (g/L)/ OD600 | 3HPDH SA, pH 8.0 | | 3HPDH SA, pH 6.0 | |
|---|---|---|---|---|---|---|
| | | | NADH | NADPH | NADH | NADPH |
| McTs263 | *E. coli* ydfG (wt) | 0.08 | 12.10 | 18.56 | 47.32 | 113.91 |
| McTs265 | *E. coli* mut6 | 0.03 | 17.95 | 0.00 | 90.38 | 23.15 |
| McTs276 | *P. putida* mmsB | 0.06 | 101.10 | 0.00 | 1878.38 | 193.42 |
| ShTh100 | *E. coli* mut22 | 0.06 | 17.25 | 0.00 | 72.88 | 24.156 |
| ShTh101 | *I. orientalis* mut27 | 0.05 | 18.30 | 0.00 | 221.67 | 24.58 |
| MBin556 | *I. orientalis* YMR226c (wt) | 0.07 | 13.78 | 68.86 | 70.69 | 292.98 |
| MeJi412 | native | 0.14 | 18.86 | 47.10 | 96.33 | 139.91 |
| McTs244 | Deletion of native YMR226c | 0.00 | 12.86 | 0.00 | 57.45 | 19.78 |

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

In some aspects, the invention may be described by the following numbered paragraphs:

[1] A 3-HPDH variant, comprising a substitution at one or more (several) positions corresponding to positions 9, 31, 32, 33, 34, 35 and 36 of SEQ ID NO: 2;
wherein the variant has at least 60%, e.g., at least 65%, at least 70%, at least 75%, at least 80%, at least 85%, at least 90%, at least 95%, at least 96%, at least 97%, at least 98%, or at least 99% sequence identity to SEQ ID NO: 2, 4, or 6; and wherein the variant has 3-HPDH activity.

[2] The variant of paragraph [1], which is a variant of a parent 3-HPDH selected from:
a. a polypeptide having at least 60% sequence identity to SEQ ID NO: 2, 4, or 6;
b. a polypeptide encoded by a polynucleotide that hybridizes under low stringency conditions with a polynucleotide having SEQ ID NO: 1, 3, 5, or the full-length complement thereof; and
c. a polypeptide encoded by a polynucleotide having at least 60% sequence identity to SEQ ID NO: 1, 3, or 5.

[3] The variant of paragraph [2], wherein the parent 3-HPDH has at least 60%, e.g., at least 65%, at least 70%, at least 75%, at least 80%, at least 85%, at least 90%, at least 95%, at least 96%, at least 97%, at least 98%, at least 99% or 100% sequence identity to SEQ ID NO: 2, 4, or 6.

[4] The variant of paragraph [2] or [3], wherein the parent 3-HPDH is encoded by a polynucleotide that hybridizes under at least low stringency conditions, e.g., medium stringency conditions, medium-high stringency conditions, high stringency conditions, or very high stringency conditions with a polynucleotide having SEQ ID NO: 1, 3, 5, or the full-length complement thereof.

[5] The variant of any of paragraphs [2]-[4], wherein the parent 3-HPDH is encoded by a polynucleotide having at least 60%, e.g., at least 65%, at least 70%, at least 75%, at least 80%, at least 85%, at least 90%, at least 95%, at least 96%, at least 97%, at least 98%, at least 99%, or 100% sequence identity to SEQ ID NO: 1, 3, or 5

[6] The variant of any of paragraphs 2-5, wherein the parent 3-HPDH comprises or consists of SEQ ID NO: 2, 4, or 6.

[7] The variant of any of paragraphs [2]-[6], which has at least 60%, e.g., at least 65%, at least 70%, at least 75%, at least 80%, at least 85%, at least 90%, at least 95% identity, at least 96%, at least 97%, at least 98%, or at least 99% sequence identity to the amino acid sequence of the parent 3-HPDH.

[8] The variant of any of paragraphs [1]-[7], wherein the number of substitutions is 1-20, e.g., 1-10 or 1-5, such as 1, 2, 3, 4, 5, 6, 7, 8, 9 or 10 substitutions.

[9] The variant of any of paragraphs [1]-[8], comprising a substitution at a position corresponding to position 9 of SEQ ID NO: 2.

[10] The variant of any one of paragraphs [1]-[9], comprising a Gly at a position corresponding to position 9 of SEQ ID NO: 2.

[11] The variant of any of paragraphs [1]-[10], comprising a substitution at a position corresponding to position 31 of SEQ ID NO: 2.

[12] The variant of any one of paragraphs [1]-[11], comprising an Asp or Glu at a position corresponding to position 31 of SEQ ID NO: 2.

[13] The variant of any of paragraphs [1]-[12], comprising a substitution at a position corresponding to position 32 of SEQ ID NO: 2.

[14] The variant of any one of paragraphs [1]-[13], comprising a Leu at a position corresponding to position 32 of SEQ ID NO: 2.

[15] The variant of any of paragraphs [1]-[14], comprising a substitution at a position corresponding to position 33 of SEQ ID NO: 2.

[16] The variant of any one of paragraphs [1]-[15], comprising a Ser or Asn at a position corresponding to position 33 of SEQ ID NO: 2.

[17] The variant of any of paragraphs [1]-[16], comprising a substitution at a position corresponding to position 34 of SEQ ID NO: 2.

[18] The variant of any one of paragraphs [1]-[17], comprising an Ala or Pro at a position corresponding to position 34 of SEQ ID NO: 2.

[19] The variant of any of paragraphs [1]-[18], comprising a substitution at a position corresponding to position 35 of SEQ ID NO: 2.

[20] The variant of any one of paragraphs [1]-[19], comprising an Ala or Asp at a position corresponding to position 35 of SEQ ID NO: 2.

[21] The variant of any of paragraphs [1]-[20], comprising a substitution at a position corresponding to position 36 of SEQ ID NO: 2.

[22] The variant of any one of paragraphs [1]-[21], comprising an Ala at a position corresponding to position 36 of SEQ ID NO: 2.

[23] The variant of any of paragraphs [1]-[22], comprising at least two substitutions at positions corresponding to any of positions 9, 31, 32, 33, 34, 35, and 36 of SEQ ID NO: 2.

[24] The variant of any of paragraphs [1]-[22], comprising at least three substitutions at positions corresponding to any of positions 9, 31, 32, 33, 34, 35, and 36 of SEQ ID NO: 2.

[25] The variant of any of paragraphs [1]-[22], comprising at least four substitutions at positions corresponding to any of positions 9, 31, 32, 33, 34, 35, and 36 of SEQ ID NO: 2.

[26] The variant of any of paragraphs [1]-[22], comprising at least five substitutions at positions corresponding to any of positions 9, 31, 32, 33, 34, 35, and 36 of SEQ ID NO: 2.

[27] The variant of any of paragraphs [1]-[22], comprising at least six substitutions at positions corresponding to any of positions 9, 31, 32, 33, 34, 35, and 36 of SEQ ID NO: 2.

[28] The variant of any of paragraphs [1]-[22], comprising seven substitutions at positions corresponding to positions 9, 31, 32, 33, 34, 35, and 36 of SEQ ID NO: 2.

[29] The variant of any of paragraphs [1]-[24], comprising one or more substitutions selected from T/S9G, G/A31D/E, R32L, R33S/N, L/K/Q34A/P, E35D/A, and K/R36A corresponding to positions of SEQ ID NO: 2.

[30] The variant of any of paragraphs [1]-[29], further comprising a deletion at a position corresponding to position 10 of SEQ ID NO: 2.

[31] The variant of any one of paragraphs [1]-[30], wherein the variant comprises or consists of SEQ ID NO: 7, 8, 9, 10, 11, 12, 13, 14, 17, 18, 19, 20, 21, 22, 23, 24, 25, 26, 27, 28, 29, 30, 31, 32, 33, 80, or 81.

[32] The variant of any of paragraphs [1]-[31], wherein the variant has increased specificity for NAD(H) compared to NADP(H) (e.g., greater than 2-fold, 5-fold, 10-fold, 20-fold, 50-fold, 100-fold, 200-fold, 500-fold, or 1000-fold specificity for NAD(H) compared to NADP(H)).

[33] The variant of any one of paragraphs [1]-[32], wherein the variant is isolated.

[34] A polynucleotide (e.g., an isolated polynucleotide) encoding the variant of any of paragraphs [1]-[32].

[35] A nucleic acid construct comprising the polynucleotide of paragraph [34].

[36] An expression vector comprising the polynucleotide of paragraph [34].

[37] A host cell comprising the polynucleotide of paragraph [35].

[38] A method of producing a 3-HPDH variant, comprising:
 a. cultivating the host cell of paragraph [37] under conditions suitable for expression of the variant; and
 b. recovering the variant.

[39] A transgenic plant, plant part or plant cell transformed with the polynucleotide of paragraph [34].

[40] A method of producing a variant of any of paragraphs [1]-[34], comprising:
 a. cultivating a transgenic plant or a plant cell comprising a polynucleotide encoding the variant under conditions conducive for production of the variant; and
 b. recovering the variant.

[41] A method for obtaining the 3-HPDH variant of any one of paragraphs [1]-[34], comprising introducing into a parent 3-HPDH a substitution at one or more positions corresponding to positions 9, 31, 32, 33, 34, 35, and 36 of SEQ ID NO: 2; and recovering the variant.

[42] A polypeptide having 3-HPDH activity, wherein the polypeptide is:
 a. a polypeptide having at least 60%, e.g., at least 65%, at least 70%, at least 75%, at least 80%, at least 85%, at least 90%, at least 95%, at least 96%, at least 97%, at least 98%, or at least 99%, sequence identity to SEQ ID NO: 2, 4, or 6;
 b. a polypeptide encoded by a polynucleotide that hybridizes under low stringency conditions, e.g., medium stringency conditions, medium-high stringency conditions, high stringency conditions, or very high stringency conditions with a polynucleotide having SEQ ID NO: 1, 3, 5, or the full-length complement thereof; or
 c. a polypeptide encoded by a polynucleotide having at least 60% sequence identity to SEQ ID NO: 1, 3, or 5;
 and wherein the polypeptide has increased specificity for NAD(H) compared to NADP(H) (e.g., greater than 2-fold, 5-fold, 10-fold, 20-fold, 50-fold, 100-fold, 200-fold, 500-fold, or 1000-fold specificity for NAD(H) compared to NADP(H)).

[43] The polypeptide of paragraph [42], having at least 60%, e.g., at least 65%, at least 70%, at least 75%, at least 80%, at least 85%, at least 90%, at least 95%, at least 96%, at least 97%, at least 98%, at least 99% or 100% sequence identity to SEQ ID NO: 2.

[44] The polypeptide of paragraph [42] or [43], which is encoded by a polynucleotide that hybridizes under at least low stringency conditions, e.g., medium stringency conditions, medium-high stringency conditions, high stringency conditions, or very high stringency conditions with a polynucleotide having SEQ ID NO: 1 or the full-length complement thereof.

[45] The polypeptide of any of paragraphs [42]-[44], which is encoded by a polynucleotide having at least 60%, e.g., at least 65%, at least 70%, at least 75%, at least 80%, at least 85%, at least 90%, at least 95%, at least 96%, at least 97%, at least 98%, at least 99%, or 100% sequence identity to SEQ ID NO: 1.

[46] The polypeptide of any of paragraphs [42]-[45], wherein at least one of positions 9, 31, 32, 33, 34, 35 and 36 corresponding to SEQ ID NO: 2 differs from SEQ ID NO: 2.

[47] The polypeptide of any of paragraphs [42]-[45], wherein at least two of positions 9, 31, 32, 33, 34, 35 and 36 corresponding to SEQ ID NO: 2 differ from SEQ ID NO: 2.

[48] The polypeptide of any of paragraphs [42]-[45], wherein at least three of positions 9, 31, 32, 33, 34, 35 and 36 corresponding to SEQ ID NO: 2 differ from SEQ ID NO: 2.

[49] The polypeptide of any of paragraphs [42]-[45], wherein at least four of positions 9, 31, 32, 33, 34, 35 and 36 corresponding to SEQ ID NO: 2 differ from SEQ ID NO: 2.

[50] The polypeptide of any of paragraphs [42]-[45], wherein at least five of positions 9, 31, 32, 33, 34, 35 and 36 corresponding to SEQ ID NO: 2 differ from SEQ ID NO: 2.

[51] The polypeptide of any of paragraphs [42]-[45], wherein at least six of positions 9, 31, 32, 33, 34, 35 and 36 corresponding to SEQ ID NO: 2 differ from SEQ ID NO: 2.

[52] The polypeptide of any of paragraphs [42]-[45], wherein all of positions 9, 31, 32, 33, 34, 35 and 36 corresponding to SEQ ID NO: 2 differ from SEQ ID NO: 2.

[53] The polypeptide of any of paragraphs [42]-[52], having at least 60%, e.g., at least 65%, at least 70%, at least 75%, at least 80%, at least 85%, at least 90%, at least 95%, at least 96%, at least 97%, at least 98%, at least 99% or 100% sequence identity to SEQ ID NO: 4.

[54] The polypeptide of any of paragraphs [42]-[53], which is encoded by a polynucleotide that hybridizes under at least low stringency conditions, e.g., medium stringency conditions, medium-high stringency conditions, high stringency conditions, or very high stringency conditions with a polynucleotide having SEQ ID NO: 3 or the full-length complement thereof.

[55] The polypeptide of any of paragraphs [42]-[54], which is encoded by a polynucleotide having at least 60%, e.g., at least 65%, at least 70%, at least 75%, at least 80%, at least 85%, at least 90%, at least 95%, at least 96%, at least 97%, at least 98%, at least 99%, or 100% sequence identity to SEQ ID NO: 3.

[56] The polypeptide of any of paragraphs [42]-[56], wherein at least one of positions 9, 31, 32, 33, 34, 35 and 36 corresponding to SEQ ID NO: 2 differs from SEQ ID NO: 4.

[57] The polypeptide of any of paragraphs [42]-[55], wherein at least two of positions 9, 31, 32, 33, 34, 35 and 36 corresponding to SEQ ID NO: 2 differ from SEQ ID NO: 4.

[58] The polypeptide of any of paragraphs [42]-[55], wherein at least three of positions 9, 31, 32, 33, 34, 35 and 36 corresponding to SEQ ID NO: 2 differ from SEQ ID NO: 4.

[59] The polypeptide of any of paragraphs [42]-[55], wherein at least four of positions 9, 31, 32, 33, 34, 35 and 36 corresponding to SEQ ID NO: 2 differ from SEQ ID NO: 4.

[60] The polypeptide of any of paragraphs [42]-[55], wherein at least five of positions 9, 31, 32, 33, 34, 35 and 36 corresponding to SEQ ID NO: 2 differ from SEQ ID NO: 4.

[61] The polypeptide of any of paragraphs [42]-[55], wherein at least six of positions 9, 31, 32, 33, 34, 35 and 36 corresponding to SEQ ID NO: 2 differ from SEQ ID NO: 4.

[62] The polypeptide of any of paragraphs [42]-[55], wherein all of positions 9, 31, 32, 33, 34, 35 and 36 corresponding to SEQ ID NO: 2 differ from SEQ ID NO: 4.

[63] The polypeptide of any of paragraphs [42]-[62], having at least 60%, e.g., at least 65%, at least 70%, at least 75%, at least 80%, at least 85%, at least 90%, at least 95%, at least 96%, at least 97%, at least 98%, at least 99% or 100% sequence identity to SEQ ID NO: 6.

[64] The polypeptide of any of paragraphs [42]-[63], which is encoded by a polynucleotide that hybridizes under at least low stringency conditions, e.g., medium stringency conditions, medium-high stringency conditions, high stringency conditions, or very high stringency conditions with a polynucleotide having SEQ ID NO: 5 or the full-length complement thereof.

[65] The polypeptide of any of paragraphs [42]-[64], which is encoded by a polynucleotide having at least 60%, e.g., at least 65%, at least 70%, at least 75%, at least 80%, at least 85%, at least 90%, at least 95%, at least 96%, at least 97%, at least 98%, at least 99%, or 100% sequence identity to SEQ ID NO: 5.

[66] The polypeptide of any of paragraphs [42]-[65], wherein at least one of positions 9, 31, 32, 33, 34, 35 and 36 corresponding to SEQ ID NO: 2 differs from SEQ ID NO: 6.

[67] The polypeptide of any of paragraphs [42]-[65], wherein at least two of positions 9, 31, 32, 33, 34, 35 and 36 corresponding to SEQ ID NO: 2 differ from SEQ ID NO: 6.

[68] The polypeptide of any of paragraphs [42]-[65], wherein at least three of positions 9, 31, 32, 33, 34, 35 and 36 corresponding to SEQ ID NO: 2 differ from SEQ ID NO: 6.

[69] The polypeptide of any of paragraphs [42]-[65], wherein at least four of positions 9, 31, 32, 33, 34, 35 and 36 corresponding to SEQ ID NO: 2 differ from SEQ ID NO: 6.

[70] The polypeptide of any of paragraphs [42]-[65], wherein at least five of positions 9, 31, 32, 33, 34, 35 and 36 corresponding to SEQ ID NO: 2 differ from SEQ ID NO: 6.

[71] The polypeptide of any of paragraphs [42]-[65], wherein at least six of positions 9, 31, 32, 33, 34, 35 and 36 corresponding to SEQ ID NO: 2 differ from SEQ ID NO: 6.

[72] The polypeptide of any of paragraphs [42]-[65], wherein all of positions 9, 31, 32, 33, 34, 35 and 36 corresponding to SEQ ID NO: 2 differ from SEQ ID NO: 6.

[73] The polypeptide of any one of paragraphs [42]-[72], comprising a Gly at a position corresponding to position 9 of SEQ ID NO: 2.

[74] The polypeptide of any one of paragraphs [42]-[73], comprising an Asp or Glu at a position corresponding to position 31 of SEQ ID NO: 2.

[75] The polypeptide of any one of paragraphs [42]-[74], comprising a Leu at a position corresponding to position 32 of SEQ ID NO: 2.

[76] The polypeptide of any one of paragraphs [42]-[75], comprising a Ser or Asn at a position corresponding to position 33 of SEQ ID NO: 2.

[77] The polypeptide of any one of paragraphs [42]-[76], comprising an Ala or Pro at a position corresponding to position 34 of SEQ ID NO: 2.

[78] The polypeptide of any one of paragraphs [42]-[77], comprising an Ala or Asp at a position corresponding to position 35 of SEQ ID NO: 2.

[79] The polypeptide of any one of paragraphs [42]-[78], comprising an Ala at a position corresponding to position 36 of SEQ ID NO: 2.

[80] The polypeptide of any one of paragraphs [42]-[79], further comprising a deletion at a position corresponding to position 10 of SEQ ID NO: 2.

[81] The polypeptide of any one of paragraphs [42]-[80], wherein the polypeptide comprises or consists of SEQ ID NO: 7, 8, 9, 10, 11, 12, 13, 14, 17, 18, 19, 20, 21, 22, 23, 24, 25, 26, 27, 28, 29, 30, 31, 32, 33, 80, or 81.

[82] The polypeptide of any one of paragraphs [42]-[82], wherein the polypeptide is isolated.

[83] A polynucleotide (e.g., an isolated polynucleotide) encoding the polypeptide of any of paragraphs [42]-[82].

[84] A nucleic acid construct comprising the polynucleotide of paragraph [83].

[85] An expression vector comprising the polynucleotide of paragraph [83].

[86] A host cell comprising the polynucleotide of paragraph [83].

[87] A method of producing the polypeptide of any of paragraphs [42]-[82], comprising:
 a. cultivating a host cell comprising a polynucleotide encoding the polypeptide under conditions suitable for expression of the polypeptide; and
 b. recovering the polypeptide.

[88] A transgenic plant, plant part or plant cell transformed with the polynucleotide of paragraph [83].

[89] A method of producing the polypeptide of any of paragraphs [42]-[82], comprising:
 a. cultivating a transgenic plant or a plant cell comprising a polynucleotide encoding the polypeptide under conditions conducive for production of the polypeptide; and
 b. recovering the variant.

[90] A method for obtaining the polypeptide of any of paragraphs [42]-[82], comprising introducing into a parent 3-HPDH a substitution at one or more positions corresponding to positions 9, 31, 32, 33, 34, 35, and 36 of SEQ ID NO: 2; and recovering the polypeptide.

[91] The host cell of paragraph [37] or [86], wherein cell is prokaryotic.

[92] The host cell of paragraph [37] or [86], wherein the cell is eukaryotic.

[93] The host cell of paragraph [92], wherein the cell is a yeast cell.

[94] The host cell of paragraph [93], wherein the cell belongs to a genus selected from *Issatchenkia, Candida, Kluyveromyces, Pichia, Schizosaccharomyces, Torulaspora, Zygosaccharomyces*, and *Saccharomyces*.

[95] The host cell of paragraph [94], wherein the cell is selected from *I. orientalis, C. lambica*, and *S. bulderi*.

[96] The host cell of any of paragraphs [37], [86], or [91]-[95], wherein the cell comprises an active 3-HP pathway.

[97] The host cell of any of paragraphs [37], [86], or [91]-[96], wherein the cell comprises:
  PEP carboxylase activity or pyruvate carboxylase activity;
  aspartate aminotransferase activity;
  aspartate decarboxylase activity; and
  beta-alanine/alpha-ketoglutarate aminotransferase (BAAT) acitivity.

[98] The host cell of paragraph [37], [86], or [91]-[97], wherein the cell comprises one or more heterologous polynucleotides selected from:
  a heterologous polynucleotide that encodes a PEP carboxylase,
  a heterologous polynucleotide that encodes a pyruvate carboxylase,
  a heterologous polynucleotide that encodes a aspartate aminotransferase,
  a heterologous polynucleotide that encodes a aspartate decarboxylase, and
  a heterologous polynucleotide that encodes a BAAT.

[99] A method of producing 3-HP, comprising:
  a. cultivating the host cell of any of paragraphs [37], [86], and [91]-[98] under conditions conducive for production of 3-HP; and
  b. recovering the 3-HP.

[100] A host cell comprising an active 3-HP pathway and a heterologous polynucleotide encoding a 3-HPDH having at least 60%, e.g., at least 65%, at least 70%, at least 75%, at least 80%, at least 85%, at least 90%, at least 95%, at least 96%, at least 97%, at least 98%, at least 99% or 100% sequence identity to SEQ ID NO: 82.

[101] The host cell of paragraph [100], wherein cell is prokaryotic.

[102] The host cell of paragraph [100], wherein the cell is eukaryotic.

[103] The host cell of paragraph [102], wherein the cell is a yeast cell.

[104] The host cell of paragraph [103], wherein the cell belongs to a genus selected from *Issatchenkia, Candida, Kluyveromyces, Pichia, Schizosaccharomyces, Torulaspora, Zygosaccharomyces*, and *Saccharomyces*.

[105] The host cell of paragraph [104], wherein the cell is selected from *I. orientalis, C. lambica*, and *S. bulderi*.

[106] The host cell of any of paragraphs [100]-[105], wherein the cell comprises:
  PEP carboxylase activity or pyruvate carboxylase activity;
  aspartate aminotransferase activity;
  aspartate decarboxylase activity; and
  beta-alanine/alpha-ketoglutarate aminotransferase (BAAT) activity.

[107] The host cell of paragraph [100]-[106], wherein the cell comprises one or more heterologous polynucleotides selected from:
  a heterologous polynucleotide that encodes a PEP carboxylase,
  a heterologous polynucleotide that encodes a pyruvate carboxylase,
  a heterologous polynucleotide that encodes a aspartate aminotransferase,
  a heterologous polynucleotide that encodes a aspartate decarboxylase, and
  a heterologous polynucleotide that encodes a BAAT.

[108] A method of producing 3-HP, comprising:
  a. cultivating the host cell of any of paragraphs [100]-[107] under conditions conducive for production of 3-HP; and
  b. recovering the 3-HP.

What is claimed is:

1. A 3-HPDH variant, comprising a substitution at one or more positions corresponding to positions 9, 31, 32, 33, 34, 35 and 36 of SEQ ID NO: 2;
   wherein the variant has at least 80% sequence identity to SEQ ID NO: 2, 4, or 6; and
   wherein the variant has 3-HPDH activity.

2. The variant of claim 1, comprising a substitution at a position corresponding to position 9 of SEQ ID NO: 2.

3. The variant of claim 1, comprising a Gly at a position corresponding to position 9 of SEQ ID NO: 2.

4. The variant of claim 1, comprising a substitution at a position corresponding to position 31 of SEQ ID NO: 2.

5. The variant of claim 1, comprising an Asp or Glu at a position corresponding to position 31 of SEQ ID NO: 2.

6. The variant of claim 1, comprising a substitution at a position corresponding to position 32 of SEQ ID NO: 2.

7. The variant of claim 1, comprising a Leu at a position corresponding to position 32 of SEQ ID NO: 2.

8. The variant of claim 1, wherein the variant comprises or consists of SEQ ID NO: 7, 8, 9, 10, 11, 12, 13, 14, 17, 18, 19, 20, 21, 22, 23, 24, 25, 26, 27, 28, 29, 30, 31, 32, 33, 80, or 81.

9. The variant of claim 1, wherein the variant has increased specificity for NAD(H) compared to NADP(H).

10. A polypeptide having 3-HPDH activity, wherein the polypeptide has sequence identity to SEQ ID NO: 2, 4, or 6; and wherein the polypeptide has increased specificity for NAD(H) compared to NADP(H).

11. The polypeptide of claim 10, wherein the polypeptide has at least 90% sequence identity to SEQ ID NO: 2, 4, or 6.

12. The polypeptide of claim 10, wherein the polypeptide has at least 95% sequence identity to SEQ ID NO: 2, 4, or 6.

13. The polypeptide of claim 10, wherein the polypeptide has at least 98% sequence identity to SEQ ID NO: 2, 4, or 6.

14. The polypeptide of claim 10, wherein the polypeptide has greater than 10-fold specificity for NAD(H) compared to NADP(H).

15. The 3-HPDH variant of claim 1, wherein the variant has at least 90% sequence identity to SEQ ID NO: 2, 4, or 6.

16. The 3-HPDH variant of claim 1, wherein the variant has at least 95% sequence identity to SEQ ID NO: 2, 4, or 6.

17. The 3-HPDH variant of claim 1, wherein the variant has at least 98% sequence identity to SEQ ID NO: 2, 4, or 6.

18. The 3-HPDH variant of claim 9, wherein the variant has greater than 10-fold specificity for NAD(H) compared to NADP(H).

19. The 3-HPDH variant of claim 1, wherein the variant comprises substitutions at positions corresponding to positions 9, 31, and 32 of SEQ ID NO: 2.

20. The 3-HPDH variant of claim 1, wherein the variant comprising a Gly at a position corresponding to position 9 of SEQ ID NO: 2; an Asp or Glu at a position corresponding to position 31 of SEQ ID NO: 2; and a Leu at a position corresponding to position 32 of SEQ ID NO: 2.

* * * * *

SEQUENCE LISTING

```
<160> NUMBER OF SEQ ID NOS: 82

<210> SEQ ID NO 1
<211> LENGTH: 747
<212> TYPE: DNA
<213> ORGANISM: Escherichia coli

<400> SEQUENCE: 1
atgatcgttt tggtcaccgg tgcaaccgca ggtttcggcg aatgtatcac cagaagattc    60
atccagcagg gtcacaaggt tatcgctacc ggtagaagac aagagagatt gcaagaattg   120
aaggacgagt tgggtgacaa cttgtacatc gctcaattgg acgttagaaa cagagcagct   180
atcgaagaaa tgttggcatc cttgccagct gaatggtgca acatcgacat cttggtcaac   240
aacgctggtt tggcattggg tatggaacca gctcacaagg ctagtgttga ggactgggag   300
accatgatcg acaccaacaa caagggtttg gtctacatga ccagagcagt tttgcctggt   360
atggttgaaa gaaccacgg tcacatcatc aacatcggtt ccaccgctgg ttcctggcca   420
tacgctggcg gtaacgtcta cggtgctacc aaggctttcg ttagacagtt ctccttgaac   480
ttgagaaccg acttgcacgg caccgctgtt agagttaccg acatcgaacc aggtttggtt   540
ggtggcaccg aattctccaa cgtcagattc aagggcgacg acgtaaggc tgaaaagacc   600 taccaaaaca ccgtcgcttt gaccccagaa gacgtttcag aggctgtttg gtgggtcagt   660
```

```
accttgccag cacacgtcaa catcaacacc ttggaaatga tgccagtcac ccaatcctac    720
gcaggtttga acgttcacag acaataa                                        747
```

<210> SEQ ID NO 2
<211> LENGTH: 248
<212> TYPE: PRT
<213> ORGANISM: Escherichia coli

<400> SEQUENCE: 2

| Met | Ile | Val | Leu | Val | Thr | Gly | Ala | Thr | Ala | Gly | Phe | Gly | Glu | Cys | Ile |
|---|---|---|---|---|---|---|---|---|---|---|---|---|---|---|---|
| 1 | | | | 5 | | | | | 10 | | | | | 15 | |

| Thr | Arg | Arg | Phe | Ile | Gln | Gln | Gly | His | Lys | Val | Ile | Ala | Thr | Gly | Arg |
| | | | 20 | | | | | 25 | | | | | 30 | | |

Arg Gln Glu Arg Leu Gln Glu Leu Lys Asp Glu Leu Gly Asp Asn Leu
          35                  40                  45

Tyr Ile Ala Gln Leu Asp Val Arg Asn Arg Ala Ala Ile Glu Glu Met
     50                  55                  60

Leu Ala Ser Leu Pro Ala Glu Trp Cys Asn Ile Asp Ile Leu Val Asn
65                  70                  75                  80

Asn Ala Gly Leu Ala Leu Gly Met Glu Pro Ala His Lys Ala Ser Val
                85                  90                  95

Glu Asp Trp Glu Thr Met Ile Asp Thr Asn Asn Lys Gly Leu Val Tyr
            100                 105                 110

Met Thr Arg Ala Val Leu Pro Gly Met Val Glu Arg Asn His Gly His
        115                 120                 125

Ile Ile Asn Ile Gly Ser Thr Ala Gly Ser Trp Pro Tyr Ala Gly Gly
    130                 135                 140

Asn Val Tyr Gly Ala Thr Lys Ala Phe Val Arg Gln Phe Ser Leu Asn
145                 150                 155                 160

Leu Arg Thr Asp Leu His Gly Thr Ala Val Arg Val Thr Asp Ile Glu
                165                 170                 175

Pro Gly Leu Val Gly Gly Thr Glu Phe Ser Asn Val Arg Phe Lys Gly
            180                 185                 190

Asp Asp Gly Lys Ala Glu Lys Thr Tyr Gln Asn Thr Val Ala Leu Thr
        195                 200                 205

Pro Glu Asp Val Ser Glu Ala Val Trp Trp Val Ser Thr Leu Pro Ala
    210                 215                 220

His Val Asn Ile Asn Thr Leu Glu Met Met Pro Val Thr Gln Ser Tyr
225                 230                 235                 240

Ala Gly Leu Asn Val His Arg Gln
                245

<210> SEQ ID NO 3
<211> LENGTH: 813
<212> TYPE: DNA
<213> ORGANISM: Issatchenkia orientalis

<400> SEQUENCE: 3

```
atgtttggta atatttccca aagacttgca ggcaagaaca tcctaattac aggtgcgtcc    60
actggtatcg ataccatac agcaaagtat tttgcagaag ctgcaaatgg agacttgaag   120
ttggttttgg ctgcaagaag aaaggagaag ctggaggcac taaaggcaga cttgcttgcc   180
aagtatccat ccatcaaagt ccatattgag agtttggatg tctccaaaac ggaaaccatt   240
gcacctttct taaaggtttt acctgaggaa ttttcaattg tcgacgtgtt ggtcaacaat   300
gcaggtaagg cgcttggttt ggatccaatt ggctctgtcg atccaaagga cgtggatgaa   360
```

-continued

```
atgttccaga ccaatgtttt gggtatgatt caattgaccc agttggttgt acagcaaatg    420
aaggagagaa actccgggga cattgtccaa ctaggttcag tggctggtag aaacccatac    480
ccaggtggtg gtatctactg tgcctccaag gccgcattga gatctttac acatgtattg    540 agagaggaat tgattaatac caagattaga gtgattgaaa tcgagcctgg aaatgttgca    600
actgaggaat tttcttttga cagattcaaa ggtgataagt ccaaggccga aaaggtctat    660
gagggaaccg agccattgta tggtaccgat attgcagaat tgattctatt tgcagtttct    720
agacctcaaa acactgttat tgcagaaaca cttgttttg ctagtaacca agcttctgct    780
taccatattt tcagaggatc attagataaa tag                                813
```

<210> SEQ ID NO 4
<211> LENGTH: 270
<212> TYPE: PRT
<213> ORGANISM: Issatchenkia orientalis

<400> SEQUENCE: 4

```
Met Phe Gly Asn Ile Ser Gln Arg Leu Ala Gly Lys Asn Ile Leu Ile
 1               5                  10                  15

Thr Gly Ala Ser Thr Gly Ile Gly Tyr His Thr Ala Lys Tyr Phe Ala
            20                  25                  30

Glu Ala Ala Asn Gly Asp Leu Lys Leu Val Leu Ala Ala Arg Arg Lys
        35                  40                  45

Glu Lys Leu Glu Ala Leu Lys Ala Asp Leu Leu Ala Lys Tyr Pro Ser
    50                  55                  60

Ile Lys Val His Ile Glu Ser Leu Asp Val Ser Lys Thr Glu Thr Ile
65                  70                  75                  80

Ala Pro Phe Leu Lys Gly Leu Pro Glu Glu Phe Ser Ile Val Asp Val
                85                  90                  95

Leu Val Asn Asn Ala Gly Lys Ala Leu Gly Leu Asp Pro Ile Gly Ser
            100                 105                 110

Val Asp Pro Lys Asp Val Asp Glu Met Phe Gln Thr Asn Val Leu Gly
        115                 120                 125

Met Ile Gln Leu Thr Gln Leu Val Gln Gln Met Lys Glu Arg Asn
    130                 135                 140

Ser Gly Asp Ile Val Gln Leu Gly Ser Val Ala Gly Arg Asn Pro Tyr
145                 150                 155                 160

Pro Gly Gly Gly Ile Tyr Cys Ala Ser Lys Ala Ala Leu Arg Ser Phe
                165                 170                 175

Thr His Val Leu Arg Glu Glu Leu Ile Asn Thr Lys Ile Arg Val Ile
            180                 185                 190

Glu Ile Glu Pro Gly Asn Val Ala Thr Glu Glu Phe Ser Leu Thr Arg
        195                 200                 205

Phe Lys Gly Asp Lys Ser Lys Ala Glu Lys Val Tyr Glu Gly Thr Glu
    210                 215                 220

Pro Leu Tyr Gly Thr Asp Ile Ala Glu Leu Ile Leu Phe Ala Val Ser
225                 230                 235                 240

Arg Pro Gln Asn Thr Val Ile Ala Glu Thr Leu Val Phe Ala Ser Asn
                245                 250                 255

Gln Ala Ser Ala Tyr His Ile Phe Arg Gly Ser Leu Asp Lys
            260                 265                 270
```

<210> SEQ ID NO 5
<211> LENGTH: 804
<212> TYPE: DNA
<213> ORGANISM: Saccharomyces cerevisiae

<400> SEQUENCE: 5

```
atgtcccaag gtagaaaggc agcagaaaga ttggcaaaga agaccgtctt gatcaccggt    60
gcgtccgctg gtatcggtaa ggctaccgcg ttggagtact tggaagcatc aacggtgac   120
atgaagttga tcttggcagc aagaagattg gagaagttgg aagaattgaa gaagaccatc   180
gaccaagaat tcccaaacgc taaggtccac gttgcacaat ggacatcac ccaagcagag    240
aagatcaagc cattcatcga aaacttgcca caagaattca aggacatcga catcttggtc   300
aacaacgctg gtaaggcgtt gggttccgac agagttggtc aaatcgcaac cgaagacatc   360
caagacgtct tcgacaccaa cgtcaccgct ttgatcaaca tcacccaagc tgttttgcca   420
atcttccaag cgaagaactc cggtgacatc gtcaacttgg gttccatcgc tggtagagac   480
gcatacccaa ccggctccat ctactgcgcc tccaagttcg ctgtcggtgc tttcaccgac   540
tccttgagaa aggaattgat caacaccaag atcagagtca tcttgattgc ccctggtttg   600
gtcgaaaccg aattctcctt ggttagatac agaggtaacg aagaacaagc aaagaacgtt   660
tacaaggaca ctaccccatt gatggccgac gacgttgcag acttgatcgt ttacgctacc   720
tccagaaagc aaaacaccgt tatcgcagac accttgatct cccaaccaa ccaagcatcc    780
ccacaccaca tcttcagagg ttaa                                          804
```

<210> SEQ ID NO 6
<211> LENGTH: 267
<212> TYPE: PRT
<213> ORGANISM: Saccharomyces cerevisiae

<400> SEQUENCE: 6

Met Ser Gln Gly Arg Lys Ala Ala Glu Arg Leu Ala Lys Lys Thr Val
1               5                   10                  15

Leu Ile Thr Gly Ala Ser Ala Gly Ile Gly Lys Ala Thr Ala Leu Glu
            20                  25                  30

Tyr Leu Glu Ala Ser Asn Gly Asp Met Lys Leu Ile Leu Ala Ala Arg
        35                  40                  45

Arg Leu Glu Lys Leu Glu Glu Leu Lys Lys Thr Ile Asp Gln Glu Phe
    50                  55                  60

Pro Asn Ala Lys Val His Val Ala Gln Leu Asp Ile Thr Gln Ala Glu
65                  70                  75                  80

Lys Ile Lys Pro Phe Ile Glu Asn Leu Pro Gln Glu Phe Lys Asp Ile
                85                  90                  95

Asp Ile Leu Val Asn Asn Ala Gly Lys Ala Leu Gly Ser Asp Arg Val
            100                 105                 110

Gly Gln Ile Ala Thr Glu Asp Ile Gln Asp Val Phe Asp Thr Asn Val
        115                 120                 125

Thr Ala Leu Ile Asn Ile Thr Gln Ala Val Leu Pro Ile Phe Gln Ala
    130                 135                 140

Lys Asn Ser Gly Asp Ile Val Asn Leu Gly Ser Ile Ala Gly Arg Asp
145                 150                 155                 160

Ala Tyr Pro Thr Gly Ser Ile Tyr Cys Ala Ser Lys Phe Ala Val Gly
                165                 170                 175

Ala Phe Thr Asp Ser Leu Arg Lys Glu Leu Ile Asn Thr Lys Ile Arg
            180                 185                 190

```
Val Ile Leu Ile Ala Pro Gly Leu Val Glu Thr Glu Phe Ser Leu Val
            195                 200                 205

Arg Tyr Arg Gly Asn Glu Glu Gln Ala Lys Asn Val Tyr Lys Asp Thr
210                 215                 220

Thr Pro Leu Met Ala Asp Asp Val Ala Asp Leu Ile Val Tyr Ala Thr
225                 230                 235                 240

Ser Arg Lys Gln Asn Thr Val Ile Ala Asp Thr Leu Ile Phe Pro Thr
                245                 250                 255

Asn Gln Ala Ser Pro His His Ile Phe Arg Gly
            260                 265

<210> SEQ ID NO 7
<211> LENGTH: 247
<212> TYPE: PRT
<213> ORGANISM: Escherichia coli

<400> SEQUENCE: 7

Met Ile Val Leu Val Thr Gly Ala Gly Gly Phe Gly Glu Cys Ile Thr
1               5                   10                  15

Arg Arg Phe Ile Gln Gln Gly His Lys Val Ile Ala Thr Asp Leu Asn
            20                  25                  30

Pro Ala Ala Leu Gln Glu Leu Lys Asp Glu Leu Gly Asp Asn Leu Tyr
        35                  40                  45

Ile Ala Gln Leu Asp Val Arg Asn Arg Ala Ala Ile Glu Glu Met Leu
    50                  55                  60

Ala Ser Leu Pro Ala Glu Trp Cys Asn Ile Asp Ile Leu Val Asn Asn
65                  70                  75                  80

Ala Gly Leu Ala Leu Gly Met Glu Pro Ala His Lys Ala Ser Val Glu
                85                  90                  95

Asp Trp Glu Thr Met Ile Asp Thr Asn Asn Lys Gly Leu Val Tyr Met
            100                 105                 110

Thr Arg Ala Val Leu Pro Gly Met Val Glu Arg Asn His Gly His Ile
        115                 120                 125

Ile Asn Ile Gly Ser Thr Ala Gly Ser Trp Pro Tyr Ala Gly Gly Asn
    130                 135                 140

Val Tyr Gly Ala Thr Lys Ala Phe Val Arg Gln Phe Ser Leu Asn Leu
145                 150                 155                 160

Arg Thr Asp Leu His Gly Thr Ala Val Arg Val Thr Asp Ile Glu Pro
                165                 170                 175

Gly Leu Val Gly Gly Thr Glu Phe Ser Asn Val Arg Phe Lys Gly Asp
            180                 185                 190

Asp Gly Lys Ala Glu Lys Thr Tyr Gln Asn Thr Val Ala Leu Thr Pro
        195                 200                 205

Glu Asp Val Ser Glu Ala Val Trp Trp Val Ser Thr Leu Pro Ala His
    210                 215                 220

Val Asn Ile Asn Thr Leu Glu Met Met Pro Val Thr Gln Ser Tyr Ala
225                 230                 235                 240

Gly Leu Asn Val His Arg Gln
                245

<210> SEQ ID NO 8
<211> LENGTH: 248
<212> TYPE: PRT
<213> ORGANISM: Escherichia coli
```

```
<400> SEQUENCE: 8

Met Ile Val Leu Val Thr Gly Ala Gly Ala Gly Phe Gly Glu Cys Ile
1               5                   10                  15

Thr Arg Arg Phe Ile Gln Gln Gly His Lys Val Ile Ala Thr Glu Leu
            20                  25                  30

Asn Pro Ala Ala Leu Gln Glu Leu Lys Asp Glu Leu Gly Asp Asn Leu
        35                  40                  45

Tyr Ile Ala Gln Leu Asp Val Arg Asn Arg Ala Ala Ile Glu Glu Met
    50                  55                  60

Leu Ala Ser Leu Pro Ala Glu Trp Cys Asn Ile Asp Ile Leu Val Asn
65                  70                  75                  80

Asn Ala Gly Leu Ala Leu Gly Met Glu Pro Ala His Lys Ala Ser Val
                85                  90                  95

Glu Asp Trp Glu Thr Met Ile Asp Thr Asn Asn Lys Gly Leu Val Tyr
            100                 105                 110

Met Thr Arg Ala Val Leu Pro Gly Met Val Glu Arg Asn His Gly His
        115                 120                 125

Ile Ile Asn Ile Gly Ser Thr Ala Gly Ser Trp Pro Tyr Ala Gly Gly
    130                 135                 140

Asn Val Tyr Gly Ala Thr Lys Ala Phe Val Arg Gln Phe Ser Leu Asn
145                 150                 155                 160

Leu Arg Thr Asp Leu His Gly Thr Ala Val Arg Val Thr Asp Ile Glu
                165                 170                 175

Pro Gly Leu Val Gly Gly Thr Glu Phe Ser Asn Val Arg Phe Lys Gly
            180                 185                 190

Asp Asp Gly Lys Ala Glu Lys Thr Tyr Gln Asn Thr Val Ala Leu Thr
        195                 200                 205

Pro Glu Asp Val Ser Glu Ala Val Trp Trp Val Ser Thr Leu Pro Ala
    210                 215                 220

His Val Asn Ile Asn Thr Leu Glu Met Met Pro Val Thr Gln Ser Tyr
225                 230                 235                 240

Ala Gly Leu Asn Val His Arg Gln
                245

<210> SEQ ID NO 9
<211> LENGTH: 247
<212> TYPE: PRT
<213> ORGANISM: Escherichia coli

<400> SEQUENCE: 9

Met Ile Val Leu Val Thr Gly Ala Gly Ala Gly Phe Gly Glu Cys Ile Thr
1               5                   10                  15

Arg Arg Phe Ile Gln Gln Gly His Lys Val Ile Ala Thr Glu Leu Asn
            20                  25                  30

Pro Ala Ala Leu Gln Glu Leu Lys Asp Glu Leu Gly Asp Asn Leu Tyr
        35                  40                  45

Ile Ala Gln Leu Asp Val Arg Asn Arg Ala Ala Ile Glu Glu Met Leu
    50                  55                  60

Ala Ser Leu Pro Ala Glu Trp Cys Asn Ile Asp Ile Leu Val Asn Asn
65                  70                  75                  80

Ala Gly Leu Ala Leu Gly Met Glu Pro Ala His Lys Ala Ser Val Glu
                85                  90                  95

Asp Trp Glu Thr Met Ile Asp Thr Asn Asn Lys Gly Leu Val Tyr Met
            100                 105                 110
```

-continued

```
Thr Arg Ala Val Leu Pro Gly Met Val Glu Arg Asn His Gly His Ile
        115                 120                 125
Ile Asn Ile Gly Ser Thr Ala Gly Ser Trp Pro Tyr Ala Gly Gly Asn
    130                 135                 140
Val Tyr Gly Ala Thr Lys Ala Phe Val Arg Gln Phe Ser Leu Asn Leu
145                 150                 155                 160
Arg Thr Asp Leu His Gly Thr Ala Val Arg Val Thr Asp Ile Glu Pro
                165                 170                 175
Gly Leu Val Gly Gly Thr Glu Phe Ser Asn Val Arg Phe Lys Gly Asp
            180                 185                 190
Asp Gly Lys Ala Glu Lys Thr Tyr Gln Asn Thr Val Ala Leu Thr Pro
        195                 200                 205
Glu Asp Val Ser Glu Ala Val Trp Trp Val Ser Thr Leu Pro Ala His
    210                 215                 220
Val Asn Ile Asn Thr Leu Glu Met Met Pro Val Thr Gln Ser Tyr Ala
225                 230                 235                 240
Gly Leu Asn Val His Arg Gln
                245
```

<210> SEQ ID NO 10
<211> LENGTH: 248
<212> TYPE: PRT
<213> ORGANISM: Escherichia coli

<400> SEQUENCE: 10

```
Met Ile Val Leu Val Thr Gly Ala Gly Ala Phe Gly Glu Cys Ile
1               5                   10                  15
Thr Arg Arg Phe Ile Gln Gln Gly His Lys Val Ile Ala Thr Asp Leu
                20                  25                  30
Ser Ala Asp Ala Leu Gln Glu Leu Lys Asp Glu Leu Gly Asp Asn Leu
            35                  40                  45
Tyr Ile Ala Gln Leu Asp Val Arg Asn Arg Ala Ala Ile Glu Glu Met
        50                  55                  60
Leu Ala Ser Leu Pro Ala Glu Trp Cys Asn Ile Asp Ile Leu Val Asn
65                  70                  75                  80
Asn Ala Gly Leu Ala Leu Gly Met Glu Pro Ala His Lys Ala Ser Val
                85                  90                  95
Glu Asp Trp Glu Thr Met Ile Asp Thr Asn Asn Lys Gly Leu Val Tyr
            100                 105                 110
Met Thr Arg Ala Val Leu Pro Gly Met Val Glu Arg Asn His Gly His
        115                 120                 125
Ile Ile Asn Ile Gly Ser Thr Ala Gly Ser Trp Pro Tyr Ala Gly Gly
    130                 135                 140
Asn Val Tyr Gly Ala Thr Lys Ala Phe Val Arg Gln Phe Ser Leu Asn
145                 150                 155                 160
Leu Arg Thr Asp Leu His Gly Thr Ala Val Arg Val Thr Asp Ile Glu
                165                 170                 175
Pro Gly Leu Val Gly Gly Thr Glu Phe Ser Asn Val Arg Phe Lys Gly
            180                 185                 190
Asp Asp Gly Lys Ala Glu Lys Thr Tyr Gln Asn Thr Val Ala Leu Thr
        195                 200                 205
Pro Glu Asp Val Ser Glu Ala Val Trp Trp Val Ser Thr Leu Pro Ala
    210                 215                 220
```

His Val Asn Ile Asn Thr Leu Glu Met Met Pro Val Thr Gln Ser Tyr
225                 230                 235                 240

Ala Gly Leu Asn Val His Arg Gln
            245

<210> SEQ ID NO 11
<211> LENGTH: 247
<212> TYPE: PRT
<213> ORGANISM: Escherichia coli

<400> SEQUENCE: 11

Met Ile Val Leu Val Thr Gly Ala Gly Gly Phe Gly Glu Cys Ile Thr
1               5                   10                  15

Arg Arg Phe Ile Gln Gln Gly His Lys Val Ile Ala Thr Asp Leu Ser
                20                  25                  30

Ala Asp Ala Leu Gln Glu Leu Lys Asp Glu Leu Gly Asp Asn Leu Tyr
            35                  40                  45

Ile Ala Gln Leu Asp Val Arg Asn Arg Ala Ala Ile Glu Glu Met Leu
        50                  55                  60

Ala Ser Leu Pro Ala Glu Trp Cys Asn Ile Asp Ile Leu Val Asn Asn
65                  70                  75                  80

Ala Gly Leu Ala Leu Gly Met Glu Pro Ala His Lys Ala Ser Val Glu
                85                  90                  95

Asp Trp Glu Thr Met Ile Asp Thr Asn Asn Lys Gly Leu Val Tyr Met
            100                 105                 110

Thr Arg Ala Val Leu Pro Gly Met Val Glu Arg Asn His Gly His Ile
        115                 120                 125

Ile Asn Ile Gly Ser Thr Ala Gly Ser Trp Pro Tyr Ala Gly Gly Asn
130                 135                 140

Val Tyr Gly Ala Thr Lys Ala Phe Val Arg Gln Phe Ser Leu Asn Leu
145                 150                 155                 160

Arg Thr Asp Leu His Gly Thr Ala Val Arg Val Thr Asp Ile Glu Pro
                165                 170                 175

Gly Leu Val Gly Gly Thr Glu Phe Ser Asn Val Arg Phe Lys Gly Asp
            180                 185                 190

Asp Gly Lys Ala Glu Lys Thr Tyr Gln Asn Thr Val Ala Leu Thr Pro
        195                 200                 205

Glu Asp Val Ser Glu Ala Val Trp Trp Val Ser Thr Leu Pro Ala His
210                 215                 220

Val Asn Ile Asn Thr Leu Glu Met Met Pro Val Thr Gln Ser Tyr Ala
225                 230                 235                 240

Gly Leu Asn Val His Arg Gln
            245

<210> SEQ ID NO 12
<211> LENGTH: 248
<212> TYPE: PRT
<213> ORGANISM: Escherichia coli

<400> SEQUENCE: 12

Met Ile Val Leu Val Thr Gly Ala Gly Ala Gly Phe Gly Glu Cys Ile
1               5                   10                  15

Thr Arg Arg Phe Ile Gln Gln Gly His Lys Val Ile Ala Thr Asp Leu
                20                  25                  30

Asn Pro Ala Ala Leu Gln Glu Leu Lys Asp Glu Leu Gly Asp Asn Leu
            35                  40                  45

Tyr Ile Ala Gln Leu Asp Val Arg Asn Arg Ala Ala Ile Glu Glu Met
                50                  55                  60

Leu Ala Ser Leu Pro Ala Glu Trp Cys Asn Ile Asp Ile Leu Val Asn
 65                  70                  75                  80

Asn Ala Gly Leu Ala Leu Gly Met Glu Pro Ala His Lys Ala Ser Val
                 85                  90                  95

Glu Asp Trp Glu Thr Met Ile Asp Thr Asn Asn Lys Gly Leu Val Tyr
            100                 105                 110

Met Thr Arg Ala Val Leu Pro Gly Met Val Glu Arg Asn His Gly His
        115                 120                 125

Ile Ile Asn Ile Gly Ser Thr Ala Gly Ser Trp Pro Tyr Ala Gly Gly
    130                 135                 140

Asn Val Tyr Gly Ala Thr Lys Ala Phe Val Arg Gln Phe Ser Leu Asn
145                 150                 155                 160

Leu Arg Thr Asp Leu His Gly Thr Ala Val Arg Val Thr Asp Ile Glu
                165                 170                 175

Pro Gly Leu Val Gly Gly Thr Glu Phe Ser Asn Val Arg Phe Lys Gly
            180                 185                 190

Asp Asp Gly Lys Ala Glu Lys Thr Tyr Gln Asn Thr Val Ala Leu Thr
        195                 200                 205

Pro Glu Asp Val Ser Glu Ala Val Trp Trp Val Ser Thr Leu Pro Ala
    210                 215                 220

His Val Asn Ile Asn Thr Leu Glu Met Met Pro Val Thr Gln Ser Tyr
225                 230                 235                 240

Ala Gly Leu Asn Val His Arg Gln
                245

<210> SEQ ID NO 13
<211> LENGTH: 247
<212> TYPE: PRT
<213> ORGANISM: Escherichia coli

<400> SEQUENCE: 13

Met Ile Val Leu Val Thr Gly Ala Gly Gly Phe Gly Glu Cys Ile Thr
 1               5                  10                  15

Arg Arg Phe Ile Gln Gln Gly His Lys Val Ile Ala Thr Glu Leu Ser
                20                  25                  30

Ala Asp Ala Leu Gln Glu Leu Lys Asp Glu Leu Gly Asp Asn Leu Tyr
             35                  40                  45

Ile Ala Gln Leu Asp Val Arg Asn Arg Ala Ala Ile Glu Glu Met Leu
    50                  55                  60

Ala Ser Leu Pro Ala Glu Trp Cys Asn Ile Asp Ile Leu Val Asn Asn
 65                  70                  75                  80

Ala Gly Leu Ala Leu Gly Met Glu Pro Ala His Lys Ala Ser Val Glu
                 85                  90                  95

Asp Trp Glu Thr Met Ile Asp Thr Asn Asn Lys Gly Leu Val Tyr Met
            100                 105                 110

Thr Arg Ala Val Leu Pro Gly Met Val Glu Arg Asn His Gly His Ile
        115                 120                 125

Ile Asn Ile Gly Ser Thr Ala Gly Ser Trp Pro Tyr Ala Gly Gly Asn
    130                 135                 140

Val Tyr Gly Ala Thr Lys Ala Phe Val Arg Gln Phe Ser Leu Asn Leu
145                 150                 155                 160

Arg Thr Asp Leu His Gly Thr Ala Val Arg Val Thr Asp Ile Glu Pro
                165                 170                 175

Gly Leu Val Gly Gly Thr Glu Phe Ser Asn Val Arg Phe Lys Gly Asp
            180                 185                 190

Asp Gly Lys Ala Glu Lys Thr Tyr Gln Asn Thr Val Ala Leu Thr Pro
        195                 200                 205

Glu Asp Val Ser Glu Ala Val Trp Trp Val Ser Thr Leu Pro Ala His
    210                 215                 220

Val Asn Ile Asn Thr Leu Glu Met Met Pro Val Thr Gln Ser Tyr Ala
225                 230                 235                 240

Gly Leu Asn Val His Arg Gln
            245

<210> SEQ ID NO 14
<211> LENGTH: 248
<212> TYPE: PRT
<213> ORGANISM: Escherichia coli

<400> SEQUENCE: 14

Met Ile Val Leu Val Thr Gly Ala Gly Gly Phe Gly Glu Cys Ile
1               5                   10                  15

Thr Arg Arg Phe Ile Gln Gln Gly His Lys Val Ile Ala Thr Glu Leu
            20                  25                  30

Ser Ala Asp Ala Leu Gln Glu Leu Lys Asp Glu Leu Gly Asp Asn Leu
        35                  40                  45

Tyr Ile Ala Gln Leu Asp Val Arg Asn Arg Ala Ala Ile Glu Glu Met
    50                  55                  60

Leu Ala Ser Leu Pro Ala Glu Trp Cys Asn Ile Asp Ile Leu Val Asn
65                  70                  75                  80

Asn Ala Gly Leu Ala Leu Gly Met Glu Pro Ala His Lys Ala Ser Val
            85                  90                  95

Glu Asp Trp Glu Thr Met Ile Asp Thr Asn Asn Lys Gly Leu Val Tyr
        100                 105                 110

Met Thr Arg Ala Val Leu Pro Gly Met Val Glu Arg Asn His Gly His
    115                 120                 125

Ile Ile Asn Ile Gly Ser Thr Ala Gly Ser Trp Pro Tyr Ala Gly Gly
130                 135                 140

Asn Val Tyr Gly Ala Thr Lys Ala Phe Val Arg Gln Phe Ser Leu Asn
145                 150                 155                 160

Leu Arg Thr Asp Leu His Gly Thr Ala Val Arg Val Thr Asp Ile Glu
            165                 170                 175

Pro Gly Leu Val Gly Gly Thr Glu Phe Ser Asn Val Arg Phe Lys Gly
        180                 185                 190

Asp Asp Gly Lys Ala Glu Lys Thr Tyr Gln Asn Thr Val Ala Leu Thr
    195                 200                 205

Pro Glu Asp Val Ser Glu Ala Val Trp Trp Val Ser Thr Leu Pro Ala
210                 215                 220

His Val Asn Ile Asn Thr Leu Glu Met Met Pro Val Thr Gln Ser Tyr
225                 230                 235                 240

Ala Gly Leu Asn Val His Arg Gln
            245

<210> SEQ ID NO 15
<211> LENGTH: 31
<212> TYPE: DNA
<213> ORGANISM: Escherichia coli

<400> SEQUENCE: 15
cggaattcat gatcgtttta gtaactggag c                                    31

<210> SEQ ID NO 16
<211> LENGTH: 29
<212> TYPE: DNA
<213> ORGANISM: Escherichia coli

<400> SEQUENCE: 16
cgggatcctt actgacggtg gacattcag                                       29

<210> SEQ ID NO 17
<211> LENGTH: 248
<212> TYPE: PRT
<213> ORGANISM: Escherichia coli

<400> SEQUENCE: 17

Met Ile Val Leu Val Thr Gly Ala Thr Ala Gly Phe Gly Glu Cys Ile
1               5                   10                  15

Thr Arg Arg Phe Ile Gln Gln Gly His Lys Val Ile Ala Thr Asp Leu
            20                  25                  30

Asn Pro Ala Ala Leu Gln Glu Leu Lys Asp Glu Leu Gly Asp Asn Leu
        35                  40                  45

Tyr Ile Ala Gln Leu Asp Val Arg Asn Arg Ala Ala Ile Glu Glu Met
    50                  55                  60

Leu Ala Ser Leu Pro Ala Glu Trp Cys Asn Ile Asp Ile Leu Val Asn
65                  70                  75                  80

Asn Ala Gly Leu Ala Leu Gly Met Glu Pro Ala His Lys Ala Ser Val
                85                  90                  95

Glu Asp Trp Glu Thr Met Ile Asp Thr Asn Asn Lys Gly Leu Val Tyr
            100                 105                 110

Met Thr Arg Ala Val Leu Pro Gly Met Val Glu Arg Asn His Gly His
        115                 120                 125

Ile Ile Asn Ile Gly Ser Thr Ala Gly Ser Trp Pro Tyr Ala Gly Gly
    130                 135                 140

Asn Val Tyr Gly Ala Thr Lys Ala Phe Val Arg Gln Phe Ser Leu Asn
145                 150                 155                 160

Leu Arg Thr Asp Leu His Gly Thr Ala Val Arg Val Thr Asp Ile Glu
                165                 170                 175

Pro Gly Leu Val Gly Gly Thr Glu Phe Ser Asn Val Arg Phe Lys Gly
            180                 185                 190

Asp Asp Gly Lys Ala Glu Lys Thr Tyr Gln Asn Thr Val Ala Leu Thr
        195                 200                 205

Pro Glu Asp Val Ser Glu Ala Val Trp Trp Val Ser Thr Leu Pro Ala
    210                 215                 220

His Val Asn Ile Asn Thr Leu Glu Met Met Pro Val Thr Gln Ser Tyr
225                 230                 235                 240

Ala Gly Leu Asn Val His Arg Gln
                245

<210> SEQ ID NO 18
<211> LENGTH: 248
<212> TYPE: PRT
<213> ORGANISM: Escherichia coli -continued

```
<400> SEQUENCE: 18

Met Ile Val Leu Val Thr Gly Ala Gly Ala Gly Phe Gly Glu Cys Ile
1               5                   10                  15

Thr Arg Arg Phe Ile Gln Gln Gly His Lys Val Ile Ala Thr Gly Leu
            20                  25                  30

Asn Pro Ala Ala Leu Gln Glu Leu Lys Asp Glu Leu Gly Asp Asn Leu
        35                  40                  45

Tyr Ile Ala Gln Leu Asp Val Arg Asn Arg Ala Ala Ile Glu Glu Met
    50                  55                  60

Leu Ala Ser Leu Pro Ala Glu Trp Cys Asn Ile Asp Ile Leu Val Asn
65                  70                  75                  80

Asn Ala Gly Leu Ala Leu Gly Met Glu Pro Ala His Lys Ala Ser Val
                85                  90                  95

Glu Asp Trp Glu Thr Met Ile Asp Thr Asn Asn Lys Gly Leu Val Tyr
            100                 105                 110

Met Thr Arg Ala Val Leu Pro Gly Met Val Glu Arg Asn His Gly His
        115                 120                 125

Ile Ile Asn Ile Gly Ser Thr Ala Gly Ser Trp Pro Tyr Ala Gly Gly
    130                 135                 140

Asn Val Tyr Gly Ala Thr Lys Ala Phe Val Arg Gln Phe Ser Leu Asn
145                 150                 155                 160

Leu Arg Thr Asp Leu His Gly Thr Ala Val Arg Val Thr Asp Ile Glu
                165                 170                 175

Pro Gly Leu Val Gly Gly Thr Glu Phe Ser Asn Val Arg Phe Lys Gly
            180                 185                 190

Asp Asp Gly Lys Ala Glu Lys Thr Tyr Gln Asn Thr Val Ala Leu Thr
        195                 200                 205

Pro Glu Asp Val Ser Glu Ala Val Trp Trp Val Ser Thr Leu Pro Ala
    210                 215                 220

His Val Asn Ile Asn Thr Leu Glu Met Met Pro Val Thr Gln Ser Tyr
225                 230                 235                 240

Ala Gly Leu Asn Val His Arg Gln
                245

<210> SEQ ID NO 19
<211> LENGTH: 248
<212> TYPE: PRT
<213> ORGANISM: Escherichia coli

<400> SEQUENCE: 19

Met Ile Val Leu Val Thr Gly Ala Gly Ala Gly Phe Gly Glu Cys Ile
1               5                   10                  15

Thr Arg Arg Phe Ile Gln Gln Gly His Lys Val Ile Ala Thr Asp Arg
            20                  25                  30

Asn Pro Ala Ala Leu Gln Glu Leu Lys Asp Glu Leu Gly Asp Asn Leu
        35                  40                  45

Tyr Ile Ala Gln Leu Asp Val Arg Asn Arg Ala Ala Ile Glu Glu Met
    50                  55                  60

Leu Ala Ser Leu Pro Ala Glu Trp Cys Asn Ile Asp Ile Leu Val Asn
65                  70                  75                  80

Asn Ala Gly Leu Ala Leu Gly Met Glu Pro Ala His Lys Ala Ser Val
                85                  90                  95

Glu Asp Trp Glu Thr Met Ile Asp Thr Asn Asn Lys Gly Leu Val Tyr
            100                 105                 110
```

Met Thr Arg Ala Val Leu Pro Gly Met Val Glu Arg Asn His Gly His
              115                 120                 125

Ile Ile Asn Ile Gly Ser Thr Ala Gly Ser Trp Pro Tyr Ala Gly Gly
        130                 135                 140

Asn Val Tyr Gly Ala Thr Lys Ala Phe Val Arg Gln Phe Ser Leu Asn
145                 150                 155                 160

Leu Arg Thr Asp Leu His Gly Thr Ala Val Arg Val Thr Asp Ile Glu
                165                 170                 175

Pro Gly Leu Val Gly Gly Thr Glu Phe Ser Asn Val Arg Phe Lys Gly
                180                 185                 190

Asp Asp Gly Lys Ala Glu Lys Thr Tyr Gln Asn Thr Val Ala Leu Thr
            195                 200                 205

Pro Glu Asp Val Ser Glu Ala Val Trp Trp Val Ser Thr Leu Pro Ala
        210                 215                 220

His Val Asn Ile Asn Thr Leu Glu Met Met Pro Val Thr Gln Ser Tyr
225                 230                 235                 240

Ala Gly Leu Asn Val His Arg Gln
                245

<210> SEQ ID NO 20
<211> LENGTH: 248
<212> TYPE: PRT
<213> ORGANISM: Escherichia coli

<400> SEQUENCE: 20

Met Ile Val Leu Val Thr Gly Ala Gly Ala Gly Phe Gly Glu Cys Ile
1               5                   10                  15

Thr Arg Arg Phe Ile Gln Gln Gly His Lys Val Ile Ala Thr Asp Leu
                20                  25                  30

Arg Pro Ala Ala Leu Gln Glu Leu Lys Asp Glu Leu Gly Asp Asn Leu
            35                  40                  45

Tyr Ile Ala Gln Leu Asp Val Arg Asn Arg Ala Ala Ile Glu Glu Met
        50                  55                  60

Leu Ala Ser Leu Pro Ala Glu Trp Cys Asn Ile Asp Ile Leu Val Asn
65                  70                  75                  80

Asn Ala Gly Leu Ala Leu Gly Met Glu Pro Ala His Lys Ala Ser Val
                85                  90                  95

Glu Asp Trp Glu Thr Met Ile Asp Thr Asn Asn Lys Gly Leu Val Tyr
                100                 105                 110

Met Thr Arg Ala Val Leu Pro Gly Met Val Glu Arg Asn His Gly His
              115                 120                 125

Ile Ile Asn Ile Gly Ser Thr Ala Gly Ser Trp Pro Tyr Ala Gly Gly
        130                 135                 140

Asn Val Tyr Gly Ala Thr Lys Ala Phe Val Arg Gln Phe Ser Leu Asn
145                 150                 155                 160

Leu Arg Thr Asp Leu His Gly Thr Ala Val Arg Val Thr Asp Ile Glu
                165                 170                 175

Pro Gly Leu Val Gly Gly Thr Glu Phe Ser Asn Val Arg Phe Lys Gly
                180                 185                 190

Asp Asp Gly Lys Ala Glu Lys Thr Tyr Gln Asn Thr Val Ala Leu Thr
            195                 200                 205

Pro Glu Asp Val Ser Glu Ala Val Trp Trp Val Ser Thr Leu Pro Ala
        210                 215                 220

```
His Val Asn Ile Asn Thr Leu Glu Met Met Pro Val Thr Gln Ser Tyr
225                 230                 235                 240

Ala Gly Leu Asn Val His Arg Gln
                245

<210> SEQ ID NO 21
<211> LENGTH: 248
<212> TYPE: PRT
<213> ORGANISM: Escherichia coli

<400> SEQUENCE: 21

Met Ile Val Leu Val Thr Gly Ala Gly Ala Gly Phe Gly Glu Cys Ile
1               5                   10                  15

Thr Arg Arg Phe Ile Gln Gln Gly His Lys Val Ile Ala Thr Asp Leu
            20                  25                  30

Asn Gln Ala Ala Leu Gln Glu Leu Lys Asp Glu Leu Gly Asp Asn Leu
        35                  40                  45

Tyr Ile Ala Gln Leu Asp Val Arg Asn Arg Ala Ala Ile Glu Glu Met
50                  55                  60

Leu Ala Ser Leu Pro Ala Glu Trp Cys Asn Ile Asp Ile Leu Val Asn
65                  70                  75                  80

Asn Ala Gly Leu Ala Leu Gly Met Glu Pro Ala His Lys Ala Ser Val
                85                  90                  95

Glu Asp Trp Glu Thr Met Ile Asp Thr Asn Asn Lys Gly Leu Val Tyr
            100                 105                 110

Met Thr Arg Ala Val Leu Pro Gly Met Val Glu Arg Asn His Gly His
        115                 120                 125

Ile Ile Asn Ile Gly Ser Thr Ala Gly Ser Trp Pro Tyr Ala Gly Gly
130                 135                 140

Asn Val Tyr Gly Ala Thr Lys Ala Phe Val Arg Gln Phe Ser Leu Asn
145                 150                 155                 160

Leu Arg Thr Asp Leu His Gly Thr Ala Val Arg Val Thr Asp Ile Glu
                165                 170                 175

Pro Gly Leu Val Gly Gly Thr Glu Phe Ser Asn Val Arg Phe Lys Gly
            180                 185                 190

Asp Asp Gly Lys Ala Glu Lys Thr Tyr Gln Asn Thr Val Ala Leu Thr
        195                 200                 205

Pro Glu Asp Val Ser Glu Ala Val Trp Trp Val Ser Thr Leu Pro Ala
210                 215                 220

His Val Asn Ile Asn Thr Leu Glu Met Met Pro Val Thr Gln Ser Tyr
225                 230                 235                 240

Ala Gly Leu Asn Val His Arg Gln
                245

<210> SEQ ID NO 22
<211> LENGTH: 248
<212> TYPE: PRT
<213> ORGANISM: Escherichia coli

<400> SEQUENCE: 22

Met Ile Val Leu Val Thr Gly Ala Gly Ala Gly Phe Gly Glu Cys Ile
1               5                   10                  15

Thr Arg Arg Phe Ile Gln Gln Gly His Lys Val Ile Ala Thr Asp Leu
            20                  25                  30

Asn Pro Glu Ala Leu Gln Glu Leu Lys Asp Glu Leu Gly Asp Asn Leu
        35                  40                  45
```

Tyr Ile Ala Gln Leu Asp Val Arg Asn Arg Ala Ala Ile Glu Glu Met
 50                  55                  60

Leu Ala Ser Leu Pro Ala Glu Trp Cys Asn Ile Asp Ile Leu Val Asn
 65                  70                  75                  80

Asn Ala Gly Leu Ala Leu Gly Met Glu Pro Ala His Lys Ala Ser Val
                 85                  90                  95

Glu Asp Trp Glu Thr Met Ile Asp Thr Asn Asn Lys Gly Leu Val Tyr
            100                 105                 110

Met Thr Arg Ala Val Leu Pro Gly Met Val Glu Arg Asn His Gly His
        115                 120                 125

Ile Ile Asn Ile Gly Ser Thr Ala Gly Ser Trp Pro Tyr Ala Gly Gly
    130                 135                 140

Asn Val Tyr Gly Ala Thr Lys Ala Phe Val Arg Gln Phe Ser Leu Asn
145                 150                 155                 160

Leu Arg Thr Asp Leu His Gly Thr Ala Val Arg Val Thr Asp Ile Glu
                165                 170                 175

Pro Gly Leu Val Gly Gly Thr Glu Phe Ser Asn Val Arg Phe Lys Gly
            180                 185                 190

Asp Asp Gly Lys Ala Glu Lys Thr Tyr Gln Asn Thr Val Ala Leu Thr
        195                 200                 205

Pro Glu Asp Val Ser Glu Ala Val Trp Trp Val Ser Thr Leu Pro Ala
    210                 215                 220

His Val Asn Ile Asn Thr Leu Glu Met Met Pro Val Thr Gln Ser Tyr
225                 230                 235                 240

Ala Gly Leu Asn Val His Arg Gln
                245

<210> SEQ ID NO 23
<211> LENGTH: 248
<212> TYPE: PRT
<213> ORGANISM: Escherichia coli

<400> SEQUENCE: 23

Met Ile Val Leu Val Thr Gly Ala Gly Ala Gly Phe Gly Glu Cys Ile
1               5                   10                  15

Thr Arg Arg Phe Ile Gln Gln Gly His Lys Val Ile Ala Thr Asp Leu
                20                  25                  30

Asn Pro Ala Arg Leu Gln Glu Leu Lys Asp Glu Leu Gly Asp Asn Leu
            35                  40                  45

Tyr Ile Ala Gln Leu Asp Val Arg Asn Arg Ala Ala Ile Glu Glu Met
 50                  55                  60

Leu Ala Ser Leu Pro Ala Glu Trp Cys Asn Ile Asp Ile Leu Val Asn
 65                  70                  75                  80

Asn Ala Gly Leu Ala Leu Gly Met Glu Pro Ala His Lys Ala Ser Val
                 85                  90                  95

Glu Asp Trp Glu Thr Met Ile Asp Thr Asn Asn Lys Gly Leu Val Tyr
            100                 105                 110

Met Thr Arg Ala Val Leu Pro Gly Met Val Glu Arg Asn His Gly His
        115                 120                 125

Ile Ile Asn Ile Gly Ser Thr Ala Gly Ser Trp Pro Tyr Ala Gly Gly
    130                 135                 140

Asn Val Tyr Gly Ala Thr Lys Ala Phe Val Arg Gln Phe Ser Leu Asn
145                 150                 155                 160

Leu Arg Thr Asp Leu His Gly Thr Ala Val Arg Val Thr Asp Ile Glu
                165                 170                 175

```
Pro Gly Leu Val Gly Gly Thr Glu Phe Ser Asn Val Arg Phe Lys Gly
            180                 185                 190

Asp Asp Gly Lys Ala Glu Lys Thr Tyr Gln Asn Thr Val Ala Leu Thr
            195                 200                 205

Pro Glu Asp Val Ser Glu Ala Val Trp Trp Val Ser Thr Leu Pro Ala
            210                 215                 220

His Val Asn Ile Asn Thr Leu Glu Met Met Pro Val Thr Gln Ser Tyr
225                 230                 235                 240

Ala Gly Leu Asn Val His Arg Gln
            245

<210> SEQ ID NO 24
<211> LENGTH: 248
<212> TYPE: PRT
<213> ORGANISM: Escherichia coli

<400> SEQUENCE: 24

Met Ile Val Leu Val Thr Gly Ala Gly Ala Gly Phe Gly Glu Cys Ile
1               5                   10                  15

Thr Arg Arg Phe Ile Gln Gln Gly His Lys Val Ile Ala Thr Asp Leu
            20                  25                  30

Arg Gln Glu Ala Leu Gln Glu Leu Lys Asp Glu Leu Gly Asp Asn Leu
        35                  40                  45

Tyr Ile Ala Gln Leu Asp Val Arg Asn Arg Ala Ala Ile Glu Glu Met
    50                  55                  60

Leu Ala Ser Leu Pro Ala Glu Trp Cys Asn Ile Asp Ile Leu Val Asn
65                  70                  75                  80

Asn Ala Gly Leu Ala Leu Gly Met Glu Pro Ala His Lys Ala Ser Val
                85                  90                  95

Glu Asp Trp Glu Thr Met Ile Asp Thr Asn Asn Lys Gly Leu Val Tyr
            100                 105                 110

Met Thr Arg Ala Val Leu Pro Gly Met Val Glu Arg Asn His Gly His
        115                 120                 125

Ile Ile Asn Ile Gly Ser Thr Ala Gly Ser Trp Pro Tyr Ala Gly Gly
    130                 135                 140

Asn Val Tyr Gly Ala Thr Lys Ala Phe Val Arg Gln Phe Ser Leu Asn
145                 150                 155                 160

Leu Arg Thr Asp Leu His Gly Thr Ala Val Arg Val Thr Asp Ile Glu
                165                 170                 175

Pro Gly Leu Val Gly Gly Thr Glu Phe Ser Asn Val Arg Phe Lys Gly
            180                 185                 190

Asp Asp Gly Lys Ala Glu Lys Thr Tyr Gln Asn Thr Val Ala Leu Thr
            195                 200                 205

Pro Glu Asp Val Ser Glu Ala Val Trp Trp Val Ser Thr Leu Pro Ala
            210                 215                 220

His Val Asn Ile Asn Thr Leu Glu Met Met Pro Val Thr Gln Ser Tyr
225                 230                 235                 240

Ala Gly Leu Asn Val His Arg Gln
            245

<210> SEQ ID NO 25
<211> LENGTH: 248
<212> TYPE: PRT
<213> ORGANISM: Escherichia coli
```

<400> SEQUENCE: 25

```
Met Ile Val Leu Val Thr Gly Ala Gly Ala Gly Phe Gly Glu Cys Ile
1               5                   10                  15

Thr Arg Arg Phe Ile Gln Gln Gly His Lys Val Ile Ala Thr Asp Leu
            20                  25                  30

Arg Gln Ala Ala Leu Gln Glu Leu Lys Asp Glu Leu Gly Asp Asn Leu
        35                  40                  45

Tyr Ile Ala Gln Leu Asp Val Arg Asn Arg Ala Ala Ile Glu Glu Met
    50                  55                  60

Leu Ala Ser Leu Pro Ala Glu Trp Cys Asn Ile Asp Ile Leu Val Asn
65                  70                  75                  80

Asn Ala Gly Leu Ala Leu Gly Met Glu Pro Ala His Lys Ala Ser Val
                85                  90                  95

Glu Asp Trp Glu Thr Met Ile Asp Thr Asn Asn Lys Gly Leu Val Tyr
            100                 105                 110

Met Thr Arg Ala Val Leu Pro Gly Met Val Glu Arg Asn His Gly His
        115                 120                 125

Ile Ile Asn Ile Gly Ser Thr Ala Gly Ser Trp Pro Tyr Ala Gly Gly
    130                 135                 140

Asn Val Tyr Gly Ala Thr Lys Ala Phe Val Arg Gln Phe Ser Leu Asn
145                 150                 155                 160

Leu Arg Thr Asp Leu His Gly Thr Ala Val Arg Val Thr Asp Ile Glu
                165                 170                 175

Pro Gly Leu Val Gly Gly Thr Glu Phe Ser Asn Val Arg Phe Lys Gly
            180                 185                 190

Asp Asp Gly Lys Ala Glu Lys Thr Tyr Gln Asn Thr Val Ala Leu Thr
        195                 200                 205

Pro Glu Asp Val Ser Glu Ala Val Trp Trp Val Ser Thr Leu Pro Ala
    210                 215                 220

His Val Asn Ile Asn Thr Leu Glu Met Met Pro Val Thr Gln Ser Tyr
225                 230                 235                 240

Ala Gly Leu Asn Val His Arg Gln
                245
```

<210> SEQ ID NO 26
<211> LENGTH: 248
<212> TYPE: PRT
<213> ORGANISM: Escherichia coli

<400> SEQUENCE: 26

```
Met Ile Val Leu Val Thr Gly Ala Gly Ala Gly Phe Gly Glu Cys Ile
1               5                   10                  15

Thr Arg Arg Phe Ile Gln Gln Gly His Lys Val Ile Ala Thr Asp Leu
            20                  25                  30

Arg Pro Glu Ala Leu Gln Glu Leu Lys Asp Glu Leu Gly Asp Asn Leu
        35                  40                  45

Tyr Ile Ala Gln Leu Asp Val Arg Asn Arg Ala Ala Ile Glu Glu Met
    50                  55                  60

Leu Ala Ser Leu Pro Ala Glu Trp Cys Asn Ile Asp Ile Leu Val Asn
65                  70                  75                  80

Asn Ala Gly Leu Ala Leu Gly Met Glu Pro Ala His Lys Ala Ser Val
                85                  90                  95

Glu Asp Trp Glu Thr Met Ile Asp Thr Asn Asn Lys Gly Leu Val Tyr
            100                 105                 110
```

Met Thr Arg Ala Val Leu Pro Gly Met Val Glu Arg Asn His Gly His
            115                 120                 125

Ile Ile Asn Ile Gly Ser Thr Ala Gly Ser Trp Pro Tyr Ala Gly Gly
        130                 135                 140

Asn Val Tyr Gly Ala Thr Lys Ala Phe Val Arg Gln Phe Ser Leu Asn
145                 150                 155                 160

Leu Arg Thr Asp Leu His Gly Thr Ala Val Arg Val Thr Asp Ile Glu
                165                 170                 175

Pro Gly Leu Val Gly Gly Thr Glu Phe Ser Asn Val Arg Phe Lys Gly
            180                 185                 190

Asp Asp Gly Lys Ala Glu Lys Thr Tyr Gln Asn Thr Val Ala Leu Thr
        195                 200                 205

Pro Glu Asp Val Ser Glu Ala Val Trp Trp Val Ser Thr Leu Pro Ala
210                 215                 220

His Val Asn Ile Asn Thr Leu Glu Met Met Pro Val Thr Gln Ser Tyr
225                 230                 235                 240

Ala Gly Leu Asn Val His Arg Gln
                245

<210> SEQ ID NO 27
<211> LENGTH: 248
<212> TYPE: PRT
<213> ORGANISM: Escherichia coli

<400> SEQUENCE: 27

Met Ile Val Leu Val Thr Gly Ala Gly Ala Gly Phe Gly Glu Cys Ile
1               5                   10                  15

Thr Arg Arg Phe Ile Gln Gln Gly His Lys Val Ile Ala Thr Asp Leu
            20                  25                  30

Asn Gln Glu Ala Leu Gln Glu Leu Lys Asp Glu Leu Gly Asp Asn Leu
        35                  40                  45

Tyr Ile Ala Gln Leu Asp Val Arg Asn Arg Ala Ala Ile Glu Glu Met
    50                  55                  60

Leu Ala Ser Leu Pro Ala Glu Trp Cys Asn Ile Asp Ile Leu Val Asn
65                  70                  75                  80

Asn Ala Gly Leu Ala Leu Gly Met Glu Pro Ala His Lys Ala Ser Val
                85                  90                  95

Glu Asp Trp Glu Thr Met Ile Asp Thr Asn Asn Lys Gly Leu Val Tyr
            100                 105                 110

Met Thr Arg Ala Val Leu Pro Gly Met Val Glu Arg Asn His Gly His
            115                 120                 125

Ile Ile Asn Ile Gly Ser Thr Ala Gly Ser Trp Pro Tyr Ala Gly Gly
        130                 135                 140

Asn Val Tyr Gly Ala Thr Lys Ala Phe Val Arg Gln Phe Ser Leu Asn
145                 150                 155                 160

Leu Arg Thr Asp Leu His Gly Thr Ala Val Arg Val Thr Asp Ile Glu
                165                 170                 175

Pro Gly Leu Val Gly Gly Thr Glu Phe Ser Asn Val Arg Phe Lys Gly
            180                 185                 190

Asp Asp Gly Lys Ala Glu Lys Thr Tyr Gln Asn Thr Val Ala Leu Thr
        195                 200                 205

Pro Glu Asp Val Ser Glu Ala Val Trp Trp Val Ser Thr Leu Pro Ala
210                 215                 220

```
His Val Asn Ile Asn Thr Leu Glu Met Met Pro Val Thr Gln Ser Tyr
225                 230                 235                 240

Ala Gly Leu Asn Val His Arg Gln
            245

<210> SEQ ID NO 28
<211> LENGTH: 248
<212> TYPE: PRT
<213> ORGANISM: Escherichia coli

<400> SEQUENCE: 28

Met Ile Val Leu Val Thr Gly Ala Thr Ala Gly Phe Gly Glu Cys Ile
1               5                   10                  15

Thr Arg Arg Phe Ile Gln Gln Gly His Lys Val Ile Ala Thr Asp Arg
            20                  25                  30

Arg Gln Glu Arg Leu Gln Glu Leu Lys Asp Glu Leu Gly Asp Asn Leu
        35                  40                  45

Tyr Ile Ala Gln Leu Asp Val Arg Asn Arg Ala Ala Ile Glu Glu Met
50                  55                  60

Leu Ala Ser Leu Pro Ala Glu Trp Cys Asn Ile Asp Ile Leu Val Asn
65                  70                  75                  80

Asn Ala Gly Leu Ala Leu Gly Met Glu Pro Ala His Lys Ala Ser Val
                85                  90                  95

Glu Asp Trp Glu Thr Met Ile Asp Thr Asn Asn Lys Gly Leu Val Tyr
            100                 105                 110

Met Thr Arg Ala Val Leu Pro Gly Met Val Glu Arg Asn His Gly His
        115                 120                 125

Ile Ile Asn Ile Gly Ser Thr Ala Gly Ser Trp Pro Tyr Ala Gly Gly
130                 135                 140

Asn Val Tyr Gly Ala Thr Lys Ala Phe Val Arg Gln Phe Ser Leu Asn
145                 150                 155                 160

Leu Arg Thr Asp Leu His Gly Thr Ala Val Arg Val Thr Asp Ile Glu
                165                 170                 175

Pro Gly Leu Val Gly Gly Thr Glu Phe Ser Asn Val Arg Phe Lys Gly
            180                 185                 190

Asp Asp Gly Lys Ala Glu Lys Thr Tyr Gln Asn Thr Val Ala Leu Thr
        195                 200                 205

Pro Glu Asp Val Ser Glu Ala Val Trp Trp Val Ser Thr Leu Pro Ala
210                 215                 220

His Val Asn Ile Asn Thr Leu Glu Met Met Pro Val Thr Gln Ser Tyr
225                 230                 235                 240

Ala Gly Leu Asn Val His Arg Gln
            245

<210> SEQ ID NO 29
<211> LENGTH: 248
<212> TYPE: PRT
<213> ORGANISM: Escherichia coli

<400> SEQUENCE: 29

Met Ile Val Leu Val Thr Gly Ala Gly Ala Gly Phe Gly Glu Cys Ile
1               5                   10                  15

Thr Arg Arg Phe Ile Gln Gln Gly His Lys Val Ile Ala Thr Asp Arg
            20                  25                  30

Arg Gln Glu Ala Leu Gln Glu Leu Lys Asp Glu Leu Gly Asp Asn Leu
        35                  40                  45
```

Tyr Ile Ala Gln Leu Asp Val Arg Asn Arg Ala Ala Ile Glu Glu Met
    50                  55                  60

Leu Ala Ser Leu Pro Ala Glu Trp Cys Asn Ile Asp Ile Leu Val Asn
65                  70                  75                  80

Asn Ala Gly Leu Ala Leu Gly Met Glu Pro Ala His Lys Ala Ser Val
                85                  90                  95

Glu Asp Trp Glu Thr Met Ile Asp Thr Asn Asn Lys Gly Leu Val Tyr
            100                 105                 110

Met Thr Arg Ala Val Leu Pro Gly Met Val Glu Arg Asn His Gly His
            115                 120                 125

Ile Ile Asn Ile Gly Ser Thr Ala Gly Ser Trp Pro Tyr Ala Gly Gly
130                 135                 140

Asn Val Tyr Gly Ala Thr Lys Ala Phe Val Arg Gln Phe Ser Leu Asn
145                 150                 155                 160

Leu Arg Thr Asp Leu His Gly Thr Ala Val Arg Val Thr Asp Ile Glu
                165                 170                 175

Pro Gly Leu Val Gly Gly Thr Glu Phe Ser Asn Val Arg Phe Lys Gly
            180                 185                 190

Asp Asp Gly Lys Ala Glu Lys Thr Tyr Gln Asn Thr Val Ala Leu Thr
            195                 200                 205

Pro Glu Asp Val Ser Glu Ala Val Trp Trp Val Ser Thr Leu Pro Ala
210                 215                 220

His Val Asn Ile Asn Thr Leu Glu Met Met Pro Val Thr Gln Ser Tyr
225                 230                 235                 240

Ala Gly Leu Asn Val His Arg Gln
                245

<210> SEQ ID NO 30
<211> LENGTH: 248
<212> TYPE: PRT
<213> ORGANISM: Escherichia coli

<400> SEQUENCE: 30

Met Ile Val Leu Val Thr Gly Ala Gly Ala Gly Phe Gly Glu Cys Ile
1               5                   10                  15

Thr Arg Arg Phe Ile Gln Gln Gly His Lys Val Ile Ala Thr Asp Leu
                20                  25                  30

Arg Gln Glu Arg Leu Gln Glu Leu Lys Asp Glu Leu Gly Asp Asn Leu
            35                  40                  45

Tyr Ile Ala Gln Leu Asp Val Arg Asn Arg Ala Ala Ile Glu Glu Met
    50                  55                  60

Leu Ala Ser Leu Pro Ala Glu Trp Cys Asn Ile Asp Ile Leu Val Asn
65                  70                  75                  80

Asn Ala Gly Leu Ala Leu Gly Met Glu Pro Ala His Lys Ala Ser Val
                85                  90                  95

Glu Asp Trp Glu Thr Met Ile Asp Thr Asn Asn Lys Gly Leu Val Tyr
            100                 105                 110

Met Thr Arg Ala Val Leu Pro Gly Met Val Glu Arg Asn His Gly His
            115                 120                 125

Ile Ile Asn Ile Gly Ser Thr Ala Gly Ser Trp Pro Tyr Ala Gly Gly
130                 135                 140

Asn Val Tyr Gly Ala Thr Lys Ala Phe Val Arg Gln Phe Ser Leu Asn
145                 150                 155                 160

Leu Arg Thr Asp Leu His Gly Thr Ala Val Arg Val Thr Asp Ile Glu
                165                 170                 175

```
Pro Gly Leu Val Gly Gly Thr Glu Phe Ser Asn Val Arg Phe Lys Gly
            180                 185                 190

Asp Asp Gly Lys Ala Glu Lys Thr Tyr Gln Asn Thr Val Ala Leu Thr
            195                 200                 205

Pro Glu Asp Val Ser Glu Ala Val Trp Trp Val Ser Thr Leu Pro Ala
            210                 215                 220

His Val Asn Ile Asn Thr Leu Glu Met Met Pro Val Thr Gln Ser Tyr
225                 230                 235                 240

Ala Gly Leu Asn Val His Arg Gln
            245

<210> SEQ ID NO 31
<211> LENGTH: 248
<212> TYPE: PRT
<213> ORGANISM: Escherichia coli

<400> SEQUENCE: 31

Met Ile Val Leu Val Thr Gly Ala Gly Ala Gly Phe Gly Glu Cys Ile
1               5                   10                  15

Thr Arg Arg Phe Ile Gln Gln Gly His Lys Val Ile Ala Thr Gly Arg
            20                  25                  30

Arg Gln Glu Arg Leu Gln Glu Leu Lys Asp Glu Leu Gly Asp Asn Leu
        35                  40                  45

Tyr Ile Ala Gln Leu Asp Val Arg Asn Arg Ala Ala Ile Glu Glu Met
    50                  55                  60

Leu Ala Ser Leu Pro Ala Glu Trp Cys Asn Ile Asp Ile Leu Val Asn
65                  70                  75                  80

Asn Ala Gly Leu Ala Leu Gly Met Glu Pro Ala His Lys Ala Ser Val
            85                  90                  95

Glu Asp Trp Glu Thr Met Ile Asp Thr Asn Asn Lys Gly Leu Val Tyr
        100                 105                 110

Met Thr Arg Ala Val Leu Pro Gly Met Val Glu Arg Asn His Gly His
    115                 120                 125

Ile Ile Asn Ile Gly Ser Thr Ala Gly Ser Trp Pro Tyr Ala Gly Gly
130                 135                 140

Asn Val Tyr Gly Ala Thr Lys Ala Phe Val Arg Gln Phe Ser Leu Asn
145                 150                 155                 160

Leu Arg Thr Asp Leu His Gly Thr Ala Val Arg Val Thr Asp Ile Glu
            165                 170                 175

Pro Gly Leu Val Gly Gly Thr Glu Phe Ser Asn Val Arg Phe Lys Gly
            180                 185                 190

Asp Asp Gly Lys Ala Glu Lys Thr Tyr Gln Asn Thr Val Ala Leu Thr
            195                 200                 205

Pro Glu Asp Val Ser Glu Ala Val Trp Trp Val Ser Thr Leu Pro Ala
            210                 215                 220

His Val Asn Ile Asn Thr Leu Glu Met Met Pro Val Thr Gln Ser Tyr
225                 230                 235                 240

Ala Gly Leu Asn Val His Arg Gln
            245

<210> SEQ ID NO 32
<211> LENGTH: 248
<212> TYPE: PRT
<213> ORGANISM: Escherichia coli
```

-continued

```
<400> SEQUENCE: 32

Met Ile Val Leu Val Thr Gly Ala Gly Ala Gly Phe Gly Glu Cys Ile
1               5                   10                  15

Thr Arg Arg Phe Ile Gln Gln Gly His Lys Val Ile Ala Thr Asp Arg
            20                  25                  30

Arg Gln Glu Arg Leu Gln Glu Leu Lys Asp Glu Leu Gly Asp Asn Leu
        35                  40                  45

Tyr Ile Ala Gln Leu Asp Val Arg Asn Arg Ala Ala Ile Glu Glu Met
    50                  55                  60

Leu Ala Ser Leu Pro Ala Glu Trp Cys Asn Ile Asp Ile Leu Val Asn
65                  70                  75                  80

Asn Ala Gly Leu Ala Leu Gly Met Glu Pro Ala His Lys Ala Ser Val
                85                  90                  95

Glu Asp Trp Glu Thr Met Ile Asp Thr Asn Asn Lys Gly Leu Val Tyr
            100                 105                 110

Met Thr Arg Ala Val Leu Pro Gly Met Val Glu Arg Asn His Gly His
        115                 120                 125

Ile Ile Asn Ile Gly Ser Thr Ala Gly Ser Trp Pro Tyr Ala Gly Gly
    130                 135                 140

Asn Val Tyr Gly Ala Thr Lys Ala Phe Val Arg Gln Phe Ser Leu Asn
145                 150                 155                 160

Leu Arg Thr Asp Leu His Gly Thr Ala Val Arg Val Thr Asp Ile Glu
                165                 170                 175

Pro Gly Leu Val Gly Gly Thr Glu Phe Ser Asn Val Arg Phe Lys Gly
            180                 185                 190

Asp Asp Gly Lys Ala Glu Lys Thr Tyr Gln Asn Thr Val Ala Leu Thr
        195                 200                 205

Pro Glu Asp Val Ser Glu Ala Val Trp Trp Val Ser Thr Leu Pro Ala
    210                 215                 220

His Val Asn Ile Asn Thr Leu Glu Met Met Pro Val Thr Gln Ser Tyr
225                 230                 235                 240

Ala Gly Leu Asn Val His Arg Gln
                245

<210> SEQ ID NO 33
<211> LENGTH: 248
<212> TYPE: PRT
<213> ORGANISM: Escherichia coli

<400> SEQUENCE: 33

Met Ile Val Leu Val Thr Gly Ala Thr Ala Gly Phe Gly Glu Cys Ile
1               5                   10                  15

Thr Arg Arg Phe Ile Gln Gln Gly His Lys Val Ile Ala Thr Asp Leu
            20                  25                  30

Arg Gln Glu Arg Leu Gln Glu Leu Lys Asp Glu Leu Gly Asp Asn Leu
        35                  40                  45

Tyr Ile Ala Gln Leu Asp Val Arg Asn Arg Ala Ala Ile Glu Glu Met
    50                  55                  60

Leu Ala Ser Leu Pro Ala Glu Trp Cys Asn Ile Asp Ile Leu Val Asn
65                  70                  75                  80

Asn Ala Gly Leu Ala Leu Gly Met Glu Pro Ala His Lys Ala Ser Val
                85                  90                  95

Glu Asp Trp Glu Thr Met Ile Asp Thr Asn Asn Lys Gly Leu Val Tyr
            100                 105                 110
```

```
Met Thr Arg Ala Val Leu Pro Gly Met Val Glu Arg Asn His Gly His
        115                 120                 125
Ile Ile Asn Ile Gly Ser Thr Ala Gly Ser Trp Pro Tyr Ala Gly Gly
    130                 135                 140
Asn Val Tyr Gly Ala Thr Lys Ala Phe Val Arg Gln Phe Ser Leu Asn
145                 150                 155                 160
Leu Arg Thr Asp Leu His Gly Thr Ala Val Arg Val Thr Asp Ile Glu
                165                 170                 175
Pro Gly Leu Val Gly Gly Thr Glu Phe Ser Asn Val Arg Phe Lys Gly
            180                 185                 190
Asp Asp Gly Lys Ala Glu Lys Thr Tyr Gln Asn Thr Val Ala Leu Thr
        195                 200                 205
Pro Glu Asp Val Ser Glu Ala Val Trp Trp Val Ser Thr Leu Pro Ala
    210                 215                 220
His Val Asn Ile Asn Thr Leu Glu Met Met Pro Val Thr Gln Ser Tyr
225                 230                 235                 240
Ala Gly Leu Asn Val His Arg Gln
                245
```

```
<210> SEQ ID NO 34
<211> LENGTH: 43
<212> TYPE: DNA
<213> ORGANISM: Escherichia coli

<400> SEQUENCE: 34
tcgccactga tctgaacccg gaagcgttgc aggagttaaa aga        43

<210> SEQ ID NO 35
<211> LENGTH: 43
<212> TYPE: DNA
<213> ORGANISM: Escherichia coli

<400> SEQUENCE: 35
tcttttaact cctgcaacgc ttccgggttc agatcagtgg cga        43

<210> SEQ ID NO 36
<211> LENGTH: 43
<212> TYPE: DNA
<213> ORGANISM: Escherichia coli

<400> SEQUENCE: 36
ccactgatct gaacccggcc cggttgcagg agttaaaaga cga        43

<210> SEQ ID NO 37
<211> LENGTH: 43
<212> TYPE: DNA
<213> ORGANISM: Escherichia coli

<400> SEQUENCE: 37
tcgtctttta actcctgcaa ccgggccggg ttcagatcag tgg        43

<210> SEQ ID NO 38
<211> LENGTH: 43
<212> TYPE: DNA
<213> ORGANISM: Escherichia coli

<400> SEQUENCE: 38
ggcataaagt tatcgccact ggcctgaacc cggccgcgtt gca        43
```

-continued

<210> SEQ ID NO 39
<211> LENGTH: 43
<212> TYPE: DNA
<213> ORGANISM: Escherichia coli

<400> SEQUENCE: 39
tgcaacgcgg ccgggttcag gccagtggcg ataactttat gcc       43

<210> SEQ ID NO 40
<211> LENGTH: 44
<212> TYPE: DNA
<213> ORGANISM: Escherichia coli

<400> SEQUENCE: 40
tcgttttagt aactggagca acggcaggtt ttggtgaatg catt      44

<210> SEQ ID NO 41
<211> LENGTH: 44
<212> TYPE: DNA
<213> ORGANISM: Escherichia coli

<400> SEQUENCE: 41
aatgcattca ccaaaacctg ccgttgctcc agttactaaa acga      44

<210> SEQ ID NO 42
<211> LENGTH: 43
<212> TYPE: DNA
<213> ORGANISM: Escherichia coli

<400> SEQUENCE: 42
ataaagttat cgccactgat cgtaacccgg ccgcgttgca gga       43

<210> SEQ ID NO 43
<211> LENGTH: 43
<212> TYPE: DNA
<213> ORGANISM: Escherichia coli

<400> SEQUENCE: 43
tcctgcaacg cggccgggtt acgatcagtg gcgataactt tat       43

<210> SEQ ID NO 44
<211> LENGTH: 43
<212> TYPE: DNA
<213> ORGANISM: Escherichia coli

<400> SEQUENCE: 44
aactcctgca acgcggccgg gcgcagatca gtggcgataa ctt       43

<210> SEQ ID NO 45
<211> LENGTH: 43
<212> TYPE: DNA
<213> ORGANISM: Escherichia coli

<400> SEQUENCE: 45
aagttatcgc cactgatctg cgcccggccg cgttgcagga gtt       43

<210> SEQ ID NO 46
<211> LENGTH: 43
<212> TYPE: DNA
<213> ORGANISM: Escherichia coli

<400> SEQUENCE: 46
ttatcgccac tgatctgaac caggccgcgt tgcaggagtt aaa       43

<210> SEQ ID NO 47
<211> LENGTH: 43
<212> TYPE: DNA
<213> ORGANISM: Escherichia coli

<400> SEQUENCE: 47
tttaactcct gcaacgcggc ctggttcaga tcagtggcga taa        43

<210> SEQ ID NO 48
<211> LENGTH: 53
<212> TYPE: DNA
<213> ORGANISM: Escherichia coli

<400> SEQUENCE: 48
taaagttatc gccactgatc tgcgcccgga agcgttgcag gagttaaaag acg        53

<210> SEQ ID NO 49
<211> LENGTH: 53
<212> TYPE: DNA
<213> ORGANISM: Escherichia coli

<400> SEQUENCE: 49
cgtcttttaa ctcctgcaac gcttccgggc gcagatcagt ggcgataact tta        53

<210> SEQ ID NO 50
<211> LENGTH: 53
<212> TYPE: DNA
<213> ORGANISM: Escherichia coli

<400> SEQUENCE: 50
agttatcgcc actgatctgc gccaggccgc gttgcaggag ttaaaagacg aac        53

<210> SEQ ID NO 51
<211> LENGTH: 53
<212> TYPE: DNA
<213> ORGANISM: Escherichia coli

<400> SEQUENCE: 51
gttcgtcttt taactcctgc aacgcggcct ggcgcagatc agtggcgata act        53

<210> SEQ ID NO 52
<211> LENGTH: 59
<212> TYPE: DNA
<213> ORGANISM: Escherichia coli

<400> SEQUENCE: 52
gcataaagtt atcgccactg atctgcgcca ggaagcgttg caggagttaa aagacgaac        59

<210> SEQ ID NO 53
<211> LENGTH: 59
<212> TYPE: DNA
<213> ORGANISM: Escherichia coli

<400> SEQUENCE: 53
gttcgtcttt taactcctgc aacgcttcct ggcgcagatc agtggcgata actttatgc        59

<210> SEQ ID NO 54
<211> LENGTH: 53
<212> TYPE: DNA
<213> ORGANISM: Escherichia coli

<400> SEQUENCE: 54
gcataaagtt atcgccactg atctgaacca ggaagcgttg caggagttaa aag        53

-continued

```
<210> SEQ ID NO 55
<211> LENGTH: 53
<212> TYPE: DNA
<213> ORGANISM: Escherichia coli

<400> SEQUENCE: 55
cttttaactc ctgcaacgct tcctggttca gatcagtggc gataacttta tgc          53

<210> SEQ ID NO 56
<211> LENGTH: 40
<212> TYPE: DNA
<213> ORGANISM: Escherichia coli

<400> SEQUENCE: 56
gtcatcgtag tctagataaa atgatcgttt tggtcaccgg                          40

<210> SEQ ID NO 57
<211> LENGTH: 28
<212> TYPE: DNA
<213> ORGANISM: Escherichia coli

<400> SEQUENCE: 57
gtgctccatt aattaattat tgtctgtg                                       28

<210> SEQ ID NO 58
<211> LENGTH: 30
<212> TYPE: DNA
<213> ORGANISM: Escherichia coli

<400> SEQUENCE: 58
gcggaattca tgtttggtaa tatttcccaa                                     30

<210> SEQ ID NO 59
<211> LENGTH: 29
<212> TYPE: DNA
<213> ORGANISM: Escherichia coli

<400> SEQUENCE: 59
gatcccgggc tatttatcta atgatcctc                                      29

<210> SEQ ID NO 60
<211> LENGTH: 39
<212> TYPE: DNA
<213> ORGANISM: Escherichia coli

<400> SEQUENCE: 60
gttttagtaa ctggagcagg cgcaggtttt ggtgaatgc                           39

<210> SEQ ID NO 61
<211> LENGTH: 39
<212> TYPE: DNA
<213> ORGANISM: Escherichia coli

<400> SEQUENCE: 61
gcattcacca aaacctgcgc ctgctccagt tactaaaac                           39

<210> SEQ ID NO 62
<211> LENGTH: 39
<212> TYPE: DNA
<213> ORGANISM: Escherichia coli

<400> SEQUENCE: 62
cataaagtta tcgccactga tcgtcgccag gaacggttg                           39
```

<210> SEQ ID NO 63
<211> LENGTH: 39
<212> TYPE: DNA
<213> ORGANISM: Escherichia coli

<400> SEQUENCE: 63
caaccgttcc tggcgacgat cagtggcgat aactttatg          39

<210> SEQ ID NO 64
<211> LENGTH: 40
<212> TYPE: DNA
<213> ORGANISM: Escherichia coli

<400> SEQUENCE: 64
taaagttatc gccactgatc gtcgccagga agcgttgcag          40

<210> SEQ ID NO 65
<211> LENGTH: 40
<212> TYPE: DNA
<213> ORGANISM: Escherichia coli

<400> SEQUENCE: 65
ctgcaacgct tcctggcgac gatcagtggc gataactttα          40

<210> SEQ ID NO 66
<211> LENGTH: 39
<212> TYPE: DNA
<213> ORGANISM: Escherichia coli

<400> SEQUENCE: 66
actgatctgc gccaggaacg gttgcaggag ttaaaagac          39

<210> SEQ ID NO 67
<211> LENGTH: 39
<212> TYPE: DNA
<213> ORGANISM: Escherichia coli

<400> SEQUENCE: 67
gtcttttaac tcctgcaacc gttcctggcg cagatcagt          39

<210> SEQ ID NO 68
<211> LENGTH: 39
<212> TYPE: DNA
<213> ORGANISM: Escherichia coli

<400> SEQUENCE: 68
atcctaatta caggtgcggg tactggtatc ggataccat          39

<210> SEQ ID NO 69
<211> LENGTH: 39
<212> TYPE: DNA
<213> ORGANISM: Escherichia coli

<400> SEQUENCE: 69
atggtatccg ataccagtac ccgcacctgt aattaggat          39

<210> SEQ ID NO 70
<211> LENGTH: 42
<212> TYPE: DNA
<213> ORGANISM: Escherichia coli

<400> SEQUENCE: 70
ttgaagttgg ttttggctga tttaagaaag gagaagctgg ag          42

<210> SEQ ID NO 71
<211> LENGTH: 42
<212> TYPE: DNA
<213> ORGANISM: Escherichia coli

<400> SEQUENCE: 71
ctccagcttc tcctttctta aatcagccaa aaccaacttc aa                              42

<210> SEQ ID NO 72
<211> LENGTH: 31
<212> TYPE: DNA
<213> ORGANISM: Escherichia coli

<400> SEQUENCE: 72
ttgcaggcaa gaacatccta attacaggtg c                                         31

<210> SEQ ID NO 73
<211> LENGTH: 31
<212> TYPE: DNA
<213> ORGANISM: Escherichia coli

<400> SEQUENCE: 73
gcacctgtaa ttaggatgtt cttgcctgca a                                         31

<210> SEQ ID NO 74
<211> LENGTH: 33
<212> TYPE: DNA
<213> ORGANISM: Escherichia coli

<400> SEQUENCE: 74
gtagctagct aaaatgtttg gtaatatttc cca                                       33

<210> SEQ ID NO 75
<211> LENGTH: 31
<212> TYPE: DNA
<213> ORGANISM: Escherichia coli

<400> SEQUENCE: 75
tgcttaatta actatttatc taatgatcct c                                         31

<210> SEQ ID NO 76
<211> LENGTH: 33
<212> TYPE: DNA
<213> ORGANISM: Escherichia coli

<400> SEQUENCE: 76
ttggtcaccg gtgcaggtgc aggtttcggc gaa                                       33

<210> SEQ ID NO 77
<211> LENGTH: 33
<212> TYPE: DNA
<213> ORGANISM: Escherichia coli

<400> SEQUENCE: 77
ttcgccgaaa cctgcacctg caccggtgac caa                                       33

<210> SEQ ID NO 78
<211> LENGTH: 40
<212> TYPE: DNA
<213> ORGANISM: Escherichia coli

<400> SEQUENCE: 78
acaaggttat cgctaccgac ttgagacaag agagattgca                                40

-continued

<210> SEQ ID NO 79
<211> LENGTH: 40
<212> TYPE: DNA
<213> ORGANISM: Escherichia coli

<400> SEQUENCE: 79
tgcaatctct cttgtctcaa gtcggtagcg ataaccttgt                                    40

<210> SEQ ID NO 80
<211> LENGTH: 270
<212> TYPE: PRT
<213> ORGANISM: Issatchenkia orientalis

<400> SEQUENCE: 80

```
Met Phe Gly Asn Ile Ser Gln Arg Leu Ala Gly Lys Asn Ile Leu Ile
1               5                   10                  15

Thr Gly Ala Ser Thr Gly Ile Gly Tyr His Thr Ala Lys Tyr Phe Ala
            20                  25                  30

Glu Ala Ala Asn Gly Asp Leu Lys Leu Val Leu Ala Asp Leu Arg Lys
        35                  40                  45

Glu Lys Leu Glu Ala Leu Lys Ala Asp Leu Leu Ala Lys Tyr Pro Ser
    50                  55                  60

Ile Lys Val His Ile Glu Ser Leu Asp Val Ser Lys Thr Glu Thr Ile
65                  70                  75                  80

Ala Pro Phe Leu Lys Gly Leu Pro Glu Glu Phe Ser Ile Val Asp Val
                85                  90                  95

Leu Val Asn Asn Ala Gly Lys Ala Leu Gly Leu Asp Pro Ile Gly Ser
            100                 105                 110

Val Asp Pro Lys Asp Val Asp Glu Met Phe Gln Thr Asn Val Leu Gly
        115                 120                 125

Met Ile Gln Leu Thr Gln Leu Val Val Gln Met Lys Glu Arg Asn
    130                 135                 140

Ser Gly Asp Ile Val Gln Leu Gly Ser Val Ala Gly Arg Asn Pro Tyr
145                 150                 155                 160

Pro Gly Gly Gly Ile Tyr Cys Ala Ser Lys Ala Ala Leu Arg Ser Phe
                165                 170                 175

Thr His Val Leu Arg Glu Glu Leu Ile Asn Thr Lys Ile Arg Val Ile
            180                 185                 190

Glu Ile Glu Pro Gly Asn Val Ala Thr Glu Glu Phe Ser Leu Thr Arg
        195                 200                 205

Phe Lys Gly Asp Lys Ser Lys Ala Glu Lys Val Tyr Glu Gly Thr Glu
    210                 215                 220

Pro Leu Tyr Gly Thr Asp Ile Ala Glu Leu Ile Leu Phe Ala Val Ser
225                 230                 235                 240

Arg Pro Gln Asn Thr Val Ile Ala Glu Thr Leu Val Phe Ala Ser Asn
                245                 250                 255

Gln Ala Ser Ala Tyr His Ile Phe Arg Gly Ser Leu Asp Lys
            260                 265                 270
```

<210> SEQ ID NO 81
<211> LENGTH: 270
<212> TYPE: PRT
<213> ORGANISM: Issatchenkia orientalis

<400> SEQUENCE: 81

Met Phe Gly Asn Ile Ser Gln Arg Leu Ala Gly Lys Asn Ile Leu Ile
1               5                   10                  15

Thr Gly Ala Gly Thr Gly Ile Gly Tyr His Thr Ala Lys Tyr Phe Ala
            20                  25                  30

Glu Ala Ala Asn Gly Asp Leu Lys Leu Val Leu Ala Asp Leu Arg Lys
        35                  40                  45

Glu Lys Leu Glu Ala Leu Lys Ala Asp Leu Leu Ala Lys Tyr Pro Ser
    50                  55                  60

Ile Lys Val His Ile Glu Ser Leu Asp Val Ser Lys Thr Glu Thr Ile
65                  70                  75                  80

Ala Pro Phe Leu Lys Gly Leu Pro Glu Glu Phe Ser Ile Val Asp Val
                85                  90                  95

Leu Val Asn Asn Ala Gly Lys Ala Leu Gly Leu Asp Pro Ile Gly Ser
            100                 105                 110

Val Asp Pro Lys Asp Val Asp Glu Met Phe Gln Thr Asn Val Leu Gly
        115                 120                 125

Met Ile Gln Leu Thr Gln Leu Val Val Gln Gln Met Lys Glu Arg Asn
    130                 135                 140

Ser Gly Asp Ile Val Gln Leu Gly Ser Val Ala Gly Arg Asn Pro Tyr
145                 150                 155                 160

Pro Gly Gly Gly Ile Tyr Cys Ala Ser Lys Ala Ala Leu Arg Ser Phe
                165                 170                 175

Thr His Val Leu Arg Glu Glu Leu Ile Asn Thr Lys Ile Arg Val Ile
            180                 185                 190

Glu Ile Glu Pro Gly Asn Val Ala Thr Glu Glu Phe Ser Leu Thr Arg
        195                 200                 205

Phe Lys Gly Asp Lys Ser Lys Ala Glu Lys Val Tyr Glu Gly Thr Glu
    210                 215                 220

Pro Leu Tyr Gly Thr Asp Ile Ala Glu Leu Ile Leu Phe Ala Val Ser
225                 230                 235                 240

Arg Pro Gln Asn Thr Val Ile Ala Glu Thr Leu Val Phe Ala Ser Asn
                245                 250                 255

Gln Ala Ser Ala Tyr His Ile Phe Arg Gly Ser Leu Asp Lys
            260                 265                 270

<210> SEQ ID NO 82
<211> LENGTH: 295
<212> TYPE: PRT
<213> ORGANISM: Issatchenkia orientalis

<400> SEQUENCE: 82

Met Arg Ile Ala Phe Ile Gly Leu Gly Asn Met Gly Ala Pro Met Ala
1               5                   10                  15

Arg Asn Leu Ile Lys Ala Gly His Gln Leu Asn Leu Phe Asp Leu Asn
            20                  25                  30

Lys Ala Val Leu Ala Glu Leu Ala Glu Leu Gly Gly Gln Ile Ser Pro
        35                  40                  45

Ser Pro Lys Asp Ala Ala Asn Ser Glu Leu Val Ile Thr Met Leu
    50                  55                  60

Pro Ala Ala Ala His Val Arg Ser Val Tyr Leu Asn Glu Asp Gly Val
65                  70                  75                  80

Leu Ala Gly Ile Arg Pro Gly Thr Pro Thr Val Asp Cys Ser Thr Ile
                85                  90                  95

-continued

```
Asp Pro Gln Thr Ala Arg Asp Val Ser Lys Ala Ala Ala Ala Lys Gly
            100             105             110

Val Asp Met Gly Asp Ala Pro Val Ser Gly Gly Thr Gly Gly Ala Ala
        115             120             125

Ala Gly Thr Leu Thr Phe Met Val Gly Ala Ser Thr Glu Leu Phe Ala
        130             135             140

Ser Leu Lys Pro Val Leu Glu Gln Met Gly Arg Asn Ile Val His Cys
145             150             155             160

Gly Glu Val Gly Thr Gly Gln Ile Ala Lys Ile Cys Asn Asn Leu Leu
                165             170             175

Leu Gly Ile Ser Met Ile Gly Val Ser Glu Ala Met Ala Leu Gly Asn
            180             185             190

Ala Leu Gly Ile Asp Thr Lys Val Leu Ala Gly Ile Ile Asn Ser Ser
        195             200             205

Thr Gly Arg Cys Trp Ser Ser Asp Thr Tyr Asn Pro Trp Pro Gly Ile
    210             215             220

Ile Glu Thr Ala Pro Ala Ser Arg Gly Tyr Thr Gly Gly Phe Gly Ala
225             230             235             240

Glu Leu Met Leu Lys Asp Leu Gly Leu Ala Thr Glu Ala Ala Arg Gln
                245             250             255

Ala His Gln Pro Val Ile Leu Gly Ala Val Ala Gln Gln Leu Tyr Gln
            260             265             270

Ala Met Ser Leu Arg Gly Glu Gly Gly Lys Asp Phe Ser Ala Ile Val
        275             280             285

Glu Gly Tyr Arg Lys Lys Asp
    290             295
```